US012612436B2

(12) United States Patent
Schwarz

(10) Patent No.: US 12,612,436 B2
(45) Date of Patent: Apr. 28, 2026

(54) VARIANTS OF HlyA AND USES THEREOF

(71) Applicant: NUMAFERM GmbH, Duesseldorf (DE)

(72) Inventor: Christian Schwarz, Duesseldorf (DE)

(73) Assignee: NUMAFERM GmbH, Duesseldorf (DE)

( * ) Notice: Subject to any disclaimer, the term of this patent is extended or adjusted under 35 U.S.C. 154(b) by 728 days.

(21) Appl. No.: 17/912,067

(22) PCT Filed: Mar. 18, 2021

(86) PCT No.: PCT/EP2021/056949
§ 371 (c)(1),
(2) Date: Sep. 16, 2022

(87) PCT Pub. No.: WO2021/185969
PCT Pub. Date: Sep. 23, 2021

(65) Prior Publication Data
US 2023/0142538 A1     May 11, 2023

(30) Foreign Application Priority Data

Mar. 18, 2020    (EP) ..................................... 20163961
Apr. 8, 2020    (EP) ..................................... 20168779

(51) Int. Cl.
| | |
|---|---|
| *C07K 14/245* | (2006.01) |
| *C07K 14/31* | (2006.01) |
| *C12N 15/62* | (2006.01) |
| *C12N 15/74* | (2006.01) |

(52) U.S. Cl.
CPC ............ *C07K 14/245* (2013.01); *C07K 14/31* (2013.01); *C12N 15/62* (2013.01); *C12N 15/74* (2013.01); *C07K 2319/50* (2013.01)

(58) Field of Classification Search
None
See application file for complete search history.

(56) References Cited

FOREIGN PATENT DOCUMENTS

| | | |
|---|---|---|
| EP | 2583975 A1 | 4/2013 |
| WO | 8706953 A1 | 11/1987 |
| WO | 2006036406 A2 | 4/2006 |
| WO | 2011004263 A2 | 1/2011 |
| WO | 2013057312 A1 | 4/2013 |
| WO | 2014081884 A1 | 5/2014 |
| WO | 2014170430 A1 | 10/2014 |
| WO | 2015049332 A1 | 4/2015 |
| WO | WO-2018172447 A1 * | 9/2018 ........... A61K 39/145 |

OTHER PUBLICATIONS

Uniprot accession No. Q1M2T3 (Year: 2006).*
Extended European Search Report dated Jun. 4, 2020, from parallel EP Application 20 163 961.4, 7 pages (for reference purposes only).
Extended European Search Report dated Jun. 4, 2020, from parallel EP Application 20 168 779.5, 8 pages (for reference purposes only).
International search report dated Jun. 4, 2021, from parallel PCT Application PCT/EP2021/056949, 12 pages (for reference purposes only).
Linton et al., "Translocation of green fluorescent protein by comparative analysis with multiple signal peptides", Biotechnology Journal, 2012, pp. 667-676, vol. 7, Issue 5, Wiley-VCH Verlag GmbH & Co. KGaA.
Altschul et al., "Basic Local Alignment Seach Tool", J. Mol. Biol., 1990, pp. 403-410, 215, Academic Press Limited.
Altschul et al., "Gapped BLAST and PSI-BLAST: a new generation of protein database search programs", Nucleic Acids Research, 1997, pp. 3389-3402, vol. 25, No. 17.
Chenna et al., "Multiple sequence alignment with the Clustal series of programs", Nucleic Acids Research, 2003, pp. 3497-3500, vol. 31, No. 13, Oxford University Press.
Notredame et al., "T-Coffee: A Novel Method for Fast and Accurate Multiple Sequence Alignment", J. Mol. Biol., 2000, pp. 205-217, Academic Press.
Baumann et al., "Three-dimensional structure of the alkaline protease of Pseudomonas aeruginosa: a two-domain protein with a calcium binding parallel beta roll motif", The EMBO Journal, 1993, pp. 3357-3364, vol. 12, No. 9.
Meier et al., "A Calcium-gated Lid and a Large β-Roll Sandwich Are Revealed by the Crystal Structure of Extracellular Lipase from Serratia marcescens", J. Biol. Chem., 2007, pp. 31477-31483, vol. 282, No. 43, The American Society for Biochemistry and Molecular Biology, Inc.
Sambrook et al., "Molecular Cloning, A Laboratory Manual", 1989, Second Edition, Cold Spring Harbor Laboratory Press, 30 pages.
Deangelis et al., "Solid-phase reversible immobilization for the isolation of PCR products", Nucleic Acids Research, 1995, pp. 4742-4743, vol. 23, No. 22, Oxford University Press.
Gibson et al., "Enzymatic assembly of DNA molecules up to several hundred kilobases", Nature Methods, 2009, pp. 343-345, vol. 6 No. 5, Nature America, Inc.

* cited by examiner

*Primary Examiner* — Oluwatosin A Ogunbiyi
(74) *Attorney, Agent, or Firm* — KNOBBE, MARTENS, OLSON & BEAR, LLP

(57) ABSTRACT

Polypeptides comprising hemolysin A (Hly A) fragments and/or variants and a peptide or polypeptide of interest in form of a fusion protein that exhibits improved expression and secretion as well as increased solubility and stability and improved renaturation efficiency. Also encompassed are nucleic acids encoding these polypeptides. host cells that comprise said nucleic acids, and methods and uses for protein expression using said nucleic acids, host cells and polypeptides.

15 Claims, 2 Drawing Sheets

Specification includes a Sequence Listing.

SEQUENCE LISTING

```
<160> NUMBER OF SEQ ID NOS: 40

<210> SEQ ID NO 1
<211> LENGTH: 218
<212> TYPE: PRT
<213> ORGANISM: Artificial
<220> FEATURE:
<223> OTHER INFORMATION: Fragment of HlyA (HlyA1)

<400> SEQUENCE: 1

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
            115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
            165                 170                 175

Ile Ile Ser Ala Ala Gly Ser Phe Asp Val Lys Glu Glu Arg Thr Ala
            180                 185                 190

Ala Ser Leu Leu Gln Leu Ser Gly Asn Ala Ser Asp Phe Ser Tyr Gly
        195                 200                 205

Arg Asn Ser Ile Thr Leu Thr Thr Ser Ala
    210                 215

<210> SEQ ID NO 2
<211> LENGTH: 9
<212> TYPE: PRT
<213> ORGANISM: Artificial
<220> FEATURE:
<223> OTHER INFORMATION: GG repeat 11-19

<400> SEQUENCE: 2

Gly Gly Lys Gly Asn Asp Lys Leu Tyr
1               5
```

```
<210> SEQ ID NO 3
<211> LENGTH: 9
<212> TYPE: PRT
<213> ORGANISM: Artificial
<220> FEATURE:
<223> OTHER INFORMATION: GG repeat 29-37

<400> SEQUENCE: 3

Gly Gly Glu Gly Asp Asp Leu Leu Lys
1               5

<210> SEQ ID NO 4
<211> LENGTH: 9
<212> TYPE: PRT
<213> ORGANISM: Artificial
<220> FEATURE:
<223> OTHER INFORMATION: GG repeat 38-46

<400> SEQUENCE: 4

Gly Gly Tyr Gly Asn Asp Ile Tyr Arg
1               5

<210> SEQ ID NO 5
<211> LENGTH: 8
<212> TYPE: PRT
<213> ORGANISM: Artificial
<220> FEATURE:
<223> OTHER INFORMATION: GG rich sequence 60-67

<400> SEQUENCE: 5

Gly Gly Lys Glu Asp Lys Leu Ser
1               5

<210> SEQ ID NO 6
<211> LENGTH: 218
<212> TYPE: PRT
<213> ORGANISM: Artificial
<220> FEATURE:
<223> OTHER INFORMATION: HlyA1 variant L198P

<400> SEQUENCE: 6

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
                20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160
```

-continued

Tyr Gly Ser Gln Gly Asp Leu Asn Pro Leu Ile Asn Glu Ile Ser Lys
                165               170               175

Ile Ile Ser Ala Ala Gly Ser Phe Asp Val Lys Glu Glu Arg Thr Ala
                180               185               190

Ala Ser Leu Leu Gln Pro Ser Gly Asn Ala Ser Asp Phe Ser Tyr Gly
                195               200               205

Arg Asn Ser Ile Thr Leu Thr Thr Ser Ala
      210               215

<210> SEQ ID NO 7
<211> LENGTH: 218
<212> TYPE: PRT
<213> ORGANISM: Artificial
<220> FEATURE:
<223> OTHER INFORMATION: HlyA1 variant T191D

<400> SEQUENCE: 7

Gly Asn Ser Leu Ala Lys Asn Val Leu Phe Gly Gly Lys Gly Asn Asp
1               5               10               15

Lys Leu Tyr Gly Ser Glu Gly Ala Asp Leu Leu Asp Gly Gly Glu Gly
                20               25               30

Asp Asp Leu Leu Lys Gly Gly Tyr Gly Asn Asp Ile Tyr Arg Tyr Leu
                35               40               45

Ser Gly Tyr Gly His His Ile Ile Asp Asp Gly Gly Lys Glu Asp
      50               55               60

Lys Leu Ser Leu Ala Asp Ile Asp Phe Arg Asp Val Ala Phe Lys Arg
65               70               75               80

Glu Gly Asn Asp Leu Ile Met Tyr Lys Ala Glu Gly Asn Val Leu Ser
                85               90               95

Ile Gly His Lys Asn Gly Ile Thr Phe Arg Asn Trp Phe Glu Lys Glu
                100               105               110

Ser Gly Asp Ile Ser Asn His Gln Ile Glu Gln Ile Phe Asp Lys Ser
                115               120               125

Gly Arg Ile Ile Thr Pro Asp Ser Leu Lys Lys Ala Leu Glu Tyr Gln
      130               135               140

Gln Arg Asn Asn Lys Ala Ser Tyr Val Tyr Gly Asn Asp Ala Leu Ala
145               150               155               160

Tyr Gly Ser Gln Gly Asp Leu Asn Pro Leu Ile Asn Glu Ile Ser Lys
                165               170               175

Ile Ile Ser Ala Ala Gly Ser Phe Asp Val Lys Glu Glu Arg Asp Ala
                180               185               190

Ala Ser Leu Leu Gln Leu Ser Gly Asn Ala Ser Asp Phe Ser Tyr Gly
                195               200               205

Arg Asn Ser Ile Thr Leu Thr Thr Ser Ala
      210               215

<210> SEQ ID NO 8
<211> LENGTH: 218
<212> TYPE: PRT
<213> ORGANISM: Artificial
<220> FEATURE:
<223> OTHER INFORMATION: HlyA1 variant A193P

<400> SEQUENCE: 8

Gly Asn Ser Leu Ala Lys Asn Val Leu Phe Gly Gly Lys Gly Asn Asp
1               5               10               15

Lys Leu Tyr Gly Ser Glu Gly Ala Asp Leu Leu Asp Gly Gly Glu Gly

-continued

```
                20              25              30

Asp Asp Leu Leu Lys Gly Gly Tyr Gly Asn Asp Ile Tyr Arg Tyr Leu
        35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65              70              75              80

Glu Gly Asn Asp Leu Ile Met Tyr Lys Ala Glu Gly Asn Val Leu Ser
                85              90              95

Ile Gly His Lys Asn Gly Ile Thr Phe Arg Asn Trp Phe Glu Lys Glu
            100             105             110

Ser Gly Asp Ile Ser Asn His Gln Ile Glu Gln Ile Phe Asp Lys Ser
        115             120             125

Gly Arg Ile Ile Thr Pro Asp Ser Leu Lys Lys Ala Leu Glu Tyr Gln
    130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
                165             170             175

Ile Ile Ser Ala Ala Gly Ser Phe Asp Val Lys Glu Glu Arg Thr Ala
            180             185             190

Pro Ser Leu Leu Gln Leu Ser Gly Asn Ala Ser Asp Phe Ser Tyr Gly
            195             200             205

Arg Asn Ser Ile Thr Leu Thr Thr Ser Ala
    210             215
```

```
<210> SEQ ID NO 9
<211> LENGTH: 218
<212> TYPE: PRT
<213> ORGANISM: Artificial
<220> FEATURE:
<223> OTHER INFORMATION: HlyA1 variant T191H, A193H

<400> SEQUENCE: 9

Gly Asn Ser Leu Ala Lys Asn Val Leu Phe Gly Gly Lys Gly Asn Asp
1               5               10              15

Lys Leu Tyr Gly Ser Glu Gly Ala Asp Leu Leu Asp Gly Gly Glu Gly
                20              25              30

Asp Asp Leu Leu Lys Gly Gly Tyr Gly Asn Asp Ile Tyr Arg Tyr Leu
        35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65              70              75              80

Glu Gly Asn Asp Leu Ile Met Tyr Lys Ala Glu Gly Asn Val Leu Ser
                85              90              95

Ile Gly His Lys Asn Gly Ile Thr Phe Arg Asn Trp Phe Glu Lys Glu
            100             105             110

Ser Gly Asp Ile Ser Asn His Gln Ile Glu Gln Ile Phe Asp Lys Ser
        115             120             125

Gly Arg Ile Ile Thr Pro Asp Ser Leu Lys Lys Ala Leu Glu Tyr Gln
    130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
```

```
                  165              170              175
Ile Ile Ser Ala Ala Gly Ser Phe Asp Val Lys Glu Glu Arg His Ala
            180              185              190

His Ser Leu Leu Gln Leu Ser Gly Asn Ala Ser Asp Phe Ser Tyr Gly
        195              200              205

Arg Asn Ser Ile Thr Leu Thr Thr Ser Ala
    210              215
```

<210> SEQ ID NO 10
<211> LENGTH: 217
<212> TYPE: PRT
<213> ORGANISM: Artificial
<220> FEATURE:
<223> OTHER INFORMATION: HlyA1 variant del191, A192P

<400> SEQUENCE: 10

```
Gly Asn Ser Leu Ala Lys Asn Val Leu Phe Gly Gly Lys Gly Asn Asp
1               5               10               15

Lys Leu Tyr Gly Ser Glu Gly Ala Asp Leu Leu Asp Gly Gly Glu Gly
            20              25              30

Asp Asp Leu Leu Lys Gly Gly Tyr Gly Asn Asp Ile Tyr Arg Tyr Leu
        35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65              70              75              80

Glu Gly Asn Asp Leu Ile Met Tyr Lys Ala Glu Gly Asn Val Leu Ser
            85              90              95

Ile Gly His Lys Asn Gly Ile Thr Phe Arg Asn Trp Phe Glu Lys Glu
            100              105              110

Ser Gly Asp Ile Ser Asn His Gln Ile Glu Gln Ile Phe Asp Lys Ser
        115              120              125

Gly Arg Ile Ile Thr Pro Asp Ser Leu Lys Lys Ala Leu Glu Tyr Gln
        130              135              140

Gln Arg Asn Asn Lys Ala Ser Tyr Val Tyr Gly Asn Asp Ala Leu Ala
145              150              155              160

Tyr Gly Ser Gln Gly Asp Leu Asn Pro Leu Ile Asn Glu Ile Ser Lys
            165              170              175

Ile Ile Ser Ala Ala Gly Ser Phe Asp Val Lys Glu Glu Arg Pro Ala
            180              185              190

Ser Leu Leu Gln Leu Ser Gly Asn Ala Ser Asp Phe Ser Tyr Gly Arg
        195              200              205

Asn Ser Ile Thr Leu Thr Thr Ser Ala
    210              215
```

<210> SEQ ID NO 11
<211> LENGTH: 218
<212> TYPE: PRT
<213> ORGANISM: Artificial
<220> FEATURE:
<223> OTHER INFORMATION: HlyA1 variant T191G, L195S

<400> SEQUENCE: 11

```
Gly Asn Ser Leu Ala Lys Asn Val Leu Phe Gly Gly Lys Gly Asn Asp
1               5               10               15

Lys Leu Tyr Gly Ser Glu Gly Ala Asp Leu Leu Asp Gly Gly Glu Gly
            20              25              30
```

-continued

```
Asp Asp Leu Leu Lys Gly Gly Tyr Gly Asn Asp Ile Tyr Arg Tyr Leu
        35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65                  70              75                  80

Glu Gly Asn Asp Leu Ile Met Tyr Lys Ala Glu Gly Asn Val Leu Ser
                85              90                  95

Ile Gly His Lys Asn Gly Ile Thr Phe Arg Asn Trp Phe Glu Lys Glu
                100             105             110

Ser Gly Asp Ile Ser Asn His Gln Ile Glu Gln Ile Phe Asp Lys Ser
                115             120             125

Gly Arg Ile Ile Thr Pro Asp Ser Leu Lys Lys Ala Leu Glu Tyr Gln
        130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
                165             170             175

Ile Ile Ser Ala Ala Gly Ser Phe Asp Val Lys Glu Glu Arg Gly Ala
                180             185             190

Ala Ser Ser Leu Gln Leu Ser Gly Asn Ala Ser Asp Phe Ser Tyr Gly
        195             200             205

Arg Asn Ser Ile Thr Leu Thr Thr Ser Ala
        210             215
```

```
<210> SEQ ID NO 12
<211> LENGTH: 218
<212> TYPE: PRT
<213> ORGANISM: Artificial
<220> FEATURE:
<223> OTHER INFORMATION: HlyA1 variant A218D

<400> SEQUENCE: 12
```

```
Gly Asn Ser Leu Ala Lys Asn Val Leu Phe Gly Gly Lys Gly Asn Asp
1               5               10              15

Lys Leu Tyr Gly Ser Glu Gly Ala Asp Leu Leu Asp Gly Gly Glu Gly
                20              25              30

Asp Asp Leu Leu Lys Gly Gly Tyr Gly Asn Asp Ile Tyr Arg Tyr Leu
        35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65                  70              75                  80

Glu Gly Asn Asp Leu Ile Met Tyr Lys Ala Glu Gly Asn Val Leu Ser
                85              90                  95

Ile Gly His Lys Asn Gly Ile Thr Phe Arg Asn Trp Phe Glu Lys Glu
                100             105             110

Ser Gly Asp Ile Ser Asn His Gln Ile Glu Gln Ile Phe Asp Lys Ser
                115             120             125

Gly Arg Ile Ile Thr Pro Asp Ser Leu Lys Lys Ala Leu Glu Tyr Gln
        130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
                165             170             175
```

-continued

```
Ile Ile Ser Ala Ala Gly Ser Phe Asp Val Lys Glu Glu Arg Thr Ala
            180                 185                 190

Ala Ser Leu Leu Gln Leu Ser Gly Asn Ala Ser Asp Phe Ser Tyr Gly
        195                 200                 205

Arg Asn Ser Ile Thr Leu Thr Thr Ser Asp
    210                 215
```

<210> SEQ ID NO 13
<211> LENGTH: 218
<212> TYPE: PRT
<213> ORGANISM: Artificial
<220> FEATURE:
<223> OTHER INFORMATION: HlyA1 variant T191E, S194P

<400> SEQUENCE: 13

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
            165                 170                 175

Ile Ile Ser Ala Ala Gly Ser Phe Asp Val Lys Glu Glu Arg Glu Ala
            180                 185                 190

Ala Pro Leu Leu Gln Leu Ser Gly Asn Ala Ser Asp Phe Ser Tyr Gly
        195                 200                 205

Arg Asn Ser Ile Thr Leu Thr Thr Ser Ala
    210                 215
```

<210> SEQ ID NO 14
<211> LENGTH: 218
<212> TYPE: PRT
<213> ORGANISM: Artificial
<220> FEATURE:
<223> OTHER INFORMATION: HlyA1 variant T191D, L198P

<400> SEQUENCE: 14

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45
```

-continued

```
Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
                115                 120                 125

Gly Arg Ile Ile Thr Pro Asp Ser Leu Lys Lys Ala Leu Glu Tyr Gln
            130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Asp Ala
                180                 185                 190

Ala Ser Leu Leu Gln Pro Ser Gly Asn Ala Ser Asp Phe Ser Tyr Gly
                195                 200                 205

Arg Asn Ser Ile Thr Leu Thr Thr Ser Ala
    210                 215
```

```
<210> SEQ ID NO 15
<211> LENGTH: 218
<212> TYPE: PRT
<213> ORGANISM: Artificial
<220> FEATURE:
<223> OTHER INFORMATION: HlyA1 variant A193P, L198P

<400> SEQUENCE: 15
```

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
            35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
                115                 120                 125

Gly Arg Ile Ile Thr Pro Asp Ser Leu Lys Lys Ala Leu Glu Tyr Gln
            130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Thr Ala
                180                 185                 190
```

-continued

```
Pro Ser Leu Leu Gln Pro Ser Gly Asn Ala Ser Asp Phe Ser Tyr Gly
        195                 200                 205

Arg Asn Ser Ile Thr Leu Thr Thr Ser Ala
    210                 215
```

<210> SEQ ID NO 16
<211> LENGTH: 218
<212> TYPE: PRT
<213> ORGANISM: Artificial
<220> FEATURE:
<223> OTHER INFORMATION: HlyA1 variant T191H, A193D, L198P

<400> SEQUENCE: 16

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
        20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg His Ala
                180                 185                 190

Asp Ser Leu Leu Gln Pro Ser Gly Asn Ala Ser Asp Phe Ser Tyr Gly
        195                 200                 205

Arg Asn Ser Ile Thr Leu Thr Thr Ser Ala
    210                 215
```

<210> SEQ ID NO 17
<211> LENGTH: 217
<212> TYPE: PRT
<213> ORGANISM: Artificial
<220> FEATURE:
<223> OTHER INFORMATION: HlyA1 variant del191, A192P, L198P

<400> SEQUENCE: 17

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
        20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
```

-continued

```
                  50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
                115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Pro Ala
                180                 185                 190

Ser Leu Leu Gln Pro Ser Gly Asn Ala Ser Asp Phe Ser Tyr Gly Arg
                195                 200                 205

Asn Ser Ile Thr Leu Thr Thr Ser Ala
        210                 215
```

```
<210> SEQ ID NO 18
<211> LENGTH: 218
<212> TYPE: PRT
<213> ORGANISM: Artificial
<220> FEATURE:
<223> OTHER INFORMATION: HlyA1 variant T191G, L195S, L198P

<400> SEQUENCE: 18

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
                20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
        50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
                115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Gly Ala
                180                 185                 190

Ala Ser Ser Leu Gln Pro Ser Gly Asn Ala Ser Asp Phe Ser Tyr Gly
```

```
                195                 200                 205

Arg Asn Ser Ile Thr Leu Thr Thr Ser Ala
    210                 215

<210> SEQ ID NO 19
<211> LENGTH: 218
<212> TYPE: PRT
<213> ORGANISM: Artificial
<220> FEATURE:
<223> OTHER INFORMATION: HlyA1 variant L198P, A218D

<400> SEQUENCE: 19

Gly Asn Ser Leu Ala Lys Asn Val Leu Phe Gly Gly Lys Gly Asn Asp
1                   5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
            35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
            115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
            165                 170                 175

Ile Ile Ser Ala Ala Gly Ser Phe Asp Val Lys Glu Glu Arg Thr Ala
            180                 185                 190

Ala Ser Leu Leu Gln Pro Ser Gly Asn Ala Ser Asp Phe Ser Tyr Gly
            195                 200                 205

Arg Asn Ser Ile Thr Leu Thr Thr Ser Asp
    210                 215

<210> SEQ ID NO 20
<211> LENGTH: 218
<212> TYPE: PRT
<213> ORGANISM: Artificial
<220> FEATURE:
<223> OTHER INFORMATION: HlyA1 variant T191E, S194P, L198P

<400> SEQUENCE: 20

Gly Asn Ser Leu Ala Lys Asn Val Leu Phe Gly Gly Lys Gly Asn Asp
1                   5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
            35                  40                  45

Ser Gly Tyr Gly His His Ile Ile Asp Asp Asp Gly Gly Lys Glu Asp
    50                  55                  60
```

```
Lys Leu Ser Leu Ala Asp Ile Asp Phe Arg Asp Val Ala Phe Lys Arg
65              70              75              80

Glu Gly Asn Asp Leu Ile Met Tyr Lys Ala Glu Gly Asn Val Leu Ser
                85              90              95

Ile Gly His Lys Asn Gly Ile Thr Phe Arg Asn Trp Phe Glu Lys Glu
            100             105             110

Ser Gly Asp Ile Ser Asn His Gln Ile Glu Gln Ile Phe Asp Lys Ser
            115             120             125

Gly Arg Ile Ile Thr Pro Asp Ser Leu Lys Lys Ala Leu Glu Tyr Gln
        130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
                165             170             175

Ile Ile Ser Ala Ala Gly Ser Phe Asp Val Lys Glu Glu Arg Glu Ala
            180             185             190

Ala Pro Leu Leu Gln Pro Ser Gly Asn Ala Ser Asp Phe Ser Tyr Gly
            195             200             205

Arg Asn Ser Ile Thr Leu Thr Thr Ser Ala
    210             215
```

```
<210> SEQ ID NO 21
<211> LENGTH: 218
<212> TYPE: PRT
<213> ORGANISM: Artificial
<220> FEATURE:
<223> OTHER INFORMATION: HlyA1 variant T191P, L198P

<400> SEQUENCE: 21
```

```
Gly Asn Ser Leu Ala Lys Asn Val Leu Phe Gly Gly Lys Gly Asn Asp
1               5               10              15

Lys Leu Tyr Gly Ser Glu Gly Ala Asp Leu Leu Asp Gly Gly Glu Gly
                20              25              30

Asp Asp Leu Leu Lys Gly Gly Tyr Gly Asn Asp Ile Tyr Arg Tyr Leu
            35              40              45

Ser Gly Tyr Gly His His Ile Ile Asp Asp Asp Gly Gly Lys Glu Asp
    50              55              60

Lys Leu Ser Leu Ala Asp Ile Asp Phe Arg Asp Val Ala Phe Lys Arg
65              70              75              80

Glu Gly Asn Asp Leu Ile Met Tyr Lys Ala Glu Gly Asn Val Leu Ser
                85              90              95

Ile Gly His Lys Asn Gly Ile Thr Phe Arg Asn Trp Phe Glu Lys Glu
            100             105             110

Ser Gly Asp Ile Ser Asn His Gln Ile Glu Gln Ile Phe Asp Lys Ser
            115             120             125

Gly Arg Ile Ile Thr Pro Asp Ser Leu Lys Lys Ala Leu Glu Tyr Gln
        130             135             140

Gln Arg Asn Asn Lys Ala Ser Tyr Val Tyr Gly Asn Asp Ala Leu Ala
145             150             155             160

Tyr Gly Ser Gln Gly Asp Leu Asn Pro Leu Ile Asn Glu Ile Ser Lys
                165             170             175

Ile Ile Ser Ala Ala Gly Ser Phe Asp Val Lys Glu Glu Arg Pro Ala
            180             185             190

Ala Ser Leu Leu Gln Pro Ser Gly Asn Ala Ser Asp Phe Ser Tyr Gly
            195             200             205
```

```
Arg Asn Ser Ile Thr Leu Thr Thr Ser Ala
    210                 215

<210> SEQ ID NO 22
<211> LENGTH: 110
<212> TYPE: PRT
<213> ORGANISM: Artificial
<220> FEATURE:
<223> OTHER INFORMATION: HlyA1 fragment del111-218

<400> SEQUENCE: 22

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu
            100                 105                 110

<210> SEQ ID NO 23
<211> LENGTH: 134
<212> TYPE: PRT
<213> ORGANISM: Artificial
<220> FEATURE:
<223> OTHER INFORMATION: HlyA1 fragment del135-218

<400> SEQUENCE: 23

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro
    130

<210> SEQ ID NO 24
<211> LENGTH: 164
<212> TYPE: PRT
<213> ORGANISM: Artificial
<220> FEATURE:
<223> OTHER INFORMATION: HlyA1 fragment 165-218
```

<400> SEQUENCE: 24

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
            115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln
```

<210> SEQ ID NO 25
<211> LENGTH: 184
<212> TYPE: PRT
<213> ORGANISM: Artificial
<220> FEATURE:
<223> OTHER INFORMATION: HlyA1 fragment 185-218

<400> SEQUENCE: 25

```
Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
            115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe
            180
```

-continued

```
<210> SEQ ID NO 26
<211> LENGTH: 193
<212> TYPE: PRT
<213> ORGANISM: Artificial
<220> FEATURE:
<223> OTHER INFORMATION: HlyA1 fragment del164-183 del214-218

<400> SEQUENCE: 26

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Phe Asp Val Lys Glu Glu Arg Thr Ala Ala Ser Leu Leu
                165                 170                 175

Gln Leu Ser Gly Asn Ala Ser Asp Phe Ser Tyr Gly Arg Asn Ser Ile
            180                 185                 190

Thr

<210> SEQ ID NO 27
<211> LENGTH: 203
<212> TYPE: PRT
<213> ORGANISM: Artificial
<220> FEATURE:
<223> OTHER INFORMATION: HlyA1 fragment del164-173 del214-218

<400> SEQUENCE: 27

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110
```

```
Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Ile Ser Lys Ile Ile Ser Ala Ala Gly Ser Phe Asp Val
                165                 170                 175

Lys Glu Glu Arg Thr Ala Ala Ser Leu Leu Gln Leu Ser Gly Asn Ala
                180                 185                 190

Ser Asp Phe Ser Tyr Gly Arg Asn Ser Ile Thr
        195                 200
```

```
<210> SEQ ID NO 28
<211> LENGTH: 208
<212> TYPE: PRT
<213> ORGANISM: Artificial
<220> FEATURE:
<223> OTHER INFORMATION: HlyA1 fragment del164-168 del214-218

<400> SEQUENCE: 28

Gly Asn Ser Leu Ala Lys Asn Val Leu Phe Gly Gly Lys Gly Asn Asp
1                   5                   10                  15

Lys Leu Tyr Gly Ser Glu Gly Ala Asp Leu Leu Asp Gly Gly Glu Gly
                20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
                100                 105                 110

Ser Gly Asp Ile Ser Asn His Gln Ile Glu Gln Ile Phe Asp Lys Ser
        115                 120                 125

Gly Arg Ile Ile Thr Pro Asp Ser Leu Lys Lys Ala Leu Glu Tyr Gln
        130                 135                 140

Gln Arg Asn Asn Lys Ala Ser Tyr Val Tyr Gly Asn Asp Ala Leu Ala
145                 150                 155                 160

Tyr Gly Ser Pro Leu Ile Asn Glu Ile Ser Lys Ile Ile Ser Ala Ala
                165                 170                 175

Gly Ser Phe Asp Val Lys Glu Glu Arg Thr Ala Ala Ser Leu Leu Gln
                180                 185                 190

Leu Ser Gly Asn Ala Ser Asp Phe Ser Tyr Gly Arg Asn Ser Ile Thr
        195                 200                 205
```

```
<210> SEQ ID NO 29
<211> LENGTH: 4545
<212> TYPE: DNA
<213> ORGANISM: Artificial
<220> FEATURE:
<223> OTHER INFORMATION: pSU HlyA1 vector

<400> SEQUENCE: 29
tgattacgaa ttcgagctcc caaaactcat gttggtaaag tatcagaatt tcatggaggt      60
```

```
aaaattgata aacagttagc gaataaaatt tttaaacaat atcaccacga gttaataact       120
gaagtaaaaa gaaagtcaga ttttaatttt tcattaactg gttaagaggt aattaaatgg       180
gaaattctct tgcaaaaaat gtattattcg gtggaaaagg taatgacaag ctgtacggca       240
gtgagggggc agatctgctt gatggtggag aggggggatga tctcctgaaa ggcggatatg       300
gtaatgatat ttatcgttat ctgtcaggat atggtcatca tattattgat gatgatgggg       360
ggaaagagga taaactcagt ttggctgata ttgatttccg ggatgtggcc ttcaagcgag       420
aaggtaatga cctcatcatg tataaagctg aaggtaatgt tctttccatt ggtcataaaa       480
atggtattac attcaggaac tggtttgaaa aagagtcagg tgatatctct aatcaccaga       540
tagagcagat ttttgataaa agtggccgga taatcacacc tgattccctt aaaaaggcac       600
ttgagtatca acagcgtaat aataaggcaa gttatgtgta tgggaatgat gcattagcct       660
atggaagtca gggtgatctt aatccattaa ttaatgaaat cagcaaaatc atttcagctg       720
caggtagctt cgatgttaaa gaggaaagaa ctgcagcttc tttattgcag ttgtccggta       780
atgccagtga tttttcatat ggacggaact caataacccct gaccacatca gcataatata       840
ttaatttaaa tgatagcaat cttactgggc tgtgccacat aagattgcta ttttttttgg       900
agtcataatg gattcttgtc ataaaattga ttatgggtta tacgccctgg agattttagc       960
ccaataccat aacgtctctg ttaacccgga agaaattaaa catagatttg atacagacgg      1020
gacaggtctg ggattaacgt catggttgct tgctgcgaaa tctttagaac taaaggtaaa      1080
acaggtaaaa aaacaattg atcgatgata agctgtcaaa catgagaatt acaacttata      1140
tcgtatgggg ctgacttcag gtgctacatt tgaagagata aattgcactg aaatcctgca      1200
ggcatgcaag cttggcactg gccgtcgttt tacaacgtcg tgactgggaa aaccctggcg      1260
ttacccaact taatcgcctt gcagcacatc ccccttttcgc cagctggcgt aatagcgaag      1320
aggcccgcac cgatcgccct tcccaacagt tgcgcagcct gaatggcgaa tgccgttaac      1380
ggattcttga agacgaaagg gcctcgtgat acgcctattt ttataggtta atgtcatgat      1440
aataatggtt tcttagacgt caggtggcac ttttcgggga aatgtgcgcg gaacccctat      1500
ttgtttattt ttctaaatac attcaaatat gtatccgctc atgagacaat aaccctgata      1560
aatgcttcaa taatattgaa aaaggaagag tatgagtatt caacatttcc gtgtcgccct      1620
tattcccttt tttgcggcat tttgccttcc tgttttttgct cacccagaaa cgctggtgaa      1680
agtaaaagat gctgaagatc agttgggtgc acgagtgggt tacatcgaac tggatctcaa      1740
cagcggtaag atccttgaga gttttcgccc cgaagaacgt tttccaatga tgagcacttt      1800
taaagttctg ctatgtggcg cggtattatc ccgtattgac gccgggcaag agcaactcgg      1860
tcgccgcata cactattctc agaatgactt ggttgagtac tcaccagtca cagaaaagca      1920
tcttacggat ggcatgacag taagagaatt atgcagtgct gccataacca tgagtgataa      1980
cactgcggcc aacttacttc tgacaacgat cggaggaccg aaggagctaa ccgcttttt      2040 gcacaacatg ggggatcatg taactcgcct tgatcgttgg gaaccggagc tgaatgaagc      2100
cataccaaac gacgagcgtg acaccacgat gcctgtagca atggcaacaa cgttgcgcaa      2160
actattaact ggcgaactac ttactctagc ttcccggcaa caattaatag actggatgga      2220
ggcggataaa gttgcaggac cacttctgcg ctcggccctt ccggctggct ggtttattgc      2280
tgataaatct ggagccggtg agcgtgggtc tcgcggtatc attgcagcac tggggccaga      2340
tggtaagccc tcccgtatcg tagttatcta cacgacgggg agtcaggcaa ctatggatga      2400
```

-continued

```
acgaaataga cagatcgctg agataggtgc ctcactgatt aagcattggt aactgtcaga    2460
ccaagtttac tcatatatac tttagattga tttaaaactt catttttaat ttaaaaggat    2520
ctaggtgaag atcctttttg ataatctcat gaccaaaatc ccttaacgtg agttttcgtt    2580
ccactgagcg tcagaccccg tagaaaagat caaaggatct tcttgagatc ctttttttct    2640
gcgcgtaatc tgctgcttgc aaacaaaaaa accaccgcta ccagcggtgg tttgtttgcc    2700
ggatcaagag ctaccaactc tttttccgaa ggtaactggc ttcagcagag cgcagatacc    2760
aaatactgtc cttctagtgt agccgtagtt aggccaccac ttcaagaact ctgtagcacc    2820
gcctacatac ctcgctctgc taatcctgtt accagtggct gctgccagtg gcgataagtc    2880
gtgtcttacc gggttggact caagacgata gttaccggat aaggcgcagc ggtcgggctg    2940
aacggggggt tcgtgcacac agcccagctt ggagcgaacg acctacaccg aactgagata    3000
cctacagcgt gagctatgag aaagcgccac gcttcccgaa gggagaaagg cggacaggta    3060
tccggtaagc ggcagggtcg aacaggaga gcgcacgagg gagcttccag ggggaaacgc    3120
ctggtatctt tatagtcctg tcgggtttcg ccacctctga cttgagcgtc gattttgtg    3180 atgctcgtca gggggcgga gcctatggaa aaacgccagc aacgcggcct ttttacggtt    3240
cctggccttt tgctggcctt ttgctcacat gttctttcct gcgttatccc ctgattctgt    3300
ggataaccgt attaccgcct ttgagtgagc tgataccgct cgccgcagcc gaacgaccga    3360
gcgcagcgag tcagtgagcg aggaagcgga agagcgcctg atgcggtatt ttctccttac    3420
gcatctgtgc ggtatttcac accgcatatg gtgcactctc agtacaatct gctctgatgc    3480
cgcatagtta agccagtata cactccgcta tcgctacgtg actgggtcat ggctgcgccc    3540
cgacacccgc caacacccgc tgacgcgccc tgacgggctt gtctgctccc ggcatccgct    3600
tacagacaag ctgtgaccgt ctccgggagc tgcatgtgtc agaggttttc accgtcatca    3660
ccgaaacgcg cgaggcagct gcggtaaagc tcatcagcgt ggtcgtgaag cgattcacag    3720
atgtctgcct gttcatccgc gtccagctcg ttgagtttct ccagaagcgt taatgtctgg    3780
cttctgataa agcgggccat gttaagggcg gttttttcct gtttggtcac tgatgcctcc    3840
gtgtaagggg gatttctgtt catgggggta atgataccga tgaaacgaga gaggatgctc    3900
acgatacggg ttactgatga tgaacatgcc cggttactgg aacgttgtga gggtaaacaa    3960
ctggcggtat ggatgcggcg ggaccagaga aaaatcactc agggtcaatg ccagcgcttc    4020
gttaatacag atgtaggtgt tccacagggt agccagcagc atcctgcgat gcagatccgg    4080
aacataatgg tgcagggcgc tgacttccgc gtttccagac tttacgaaac acggaaaccg    4140
aagaccattc atgttgttgc tcaggtcgca gacgttttgc agcagcagtc gcttcacgtt    4200
cgctcgcgta tcggtgattc attctgctaa ccagtaaggc aaccccgcca gcctagccgg    4260
gtcctcaacg acaggagcac gatcatgcgc acccgtggcc aggacccaac gctgcccgcc    4320
gttaacggcc aatacgcaaa ccgcctctcc ccgcgcgttg gccgattcat taatgcagct    4380
ggcacgacag gtttcccgac tggaaagcgg gcagtgagcg caacgcaatt aatgtgagtt    4440
agctcactca ttaggcaccc caggctttac actttatgct tccggctcgt atgttgtgtg    4500
gaattgtgag cggataacaa tttcacacag gaaacagcta tgaca                    4545
```

<210> SEQ ID NO 30
<211> LENGTH: 707
<212> TYPE: PRT
<213> ORGANISM: Escherichia coli

<400> SEQUENCE: 30

-continued

```
Met Asp Ser Cys His Lys Ile Asp Tyr Gly Leu Tyr Ala Leu Glu Ile
1               5                   10                  15

Leu Ala Gln Tyr His Asn Val Ser Val Asn Pro Glu Glu Ile Lys His
            20                  25                  30

Arg Phe Asp Thr Asp Gly Thr Gly Leu Gly Leu Thr Ser Trp Leu Leu
        35                  40                  45

Ala Ala Lys Ser Leu Glu Leu Lys Val Lys Gln Val Lys Lys Thr Ile
    50                  55                  60

Asp Arg Leu Asn Phe Ile Ser Leu Pro Ala Leu Val Trp Arg Glu Asp
65                  70                  75                  80

Gly Arg His Phe Ile Leu Thr Lys Val Ser Lys Glu Ala Asn Arg Tyr
                85                  90                  95

Leu Ile Phe Asp Leu Glu Gln Arg Asn Pro Arg Val Leu Glu Gln Ser
            100                 105                 110

Glu Phe Glu Ala Leu Tyr Gln Gly His Ile Ile Leu Ile Ala Ser Arg
            115                 120                 125

Ser Ser Val Ala Gly Lys Leu Ala Lys Phe Asp Phe Thr Trp Phe Ile
    130                 135                 140

Pro Ala Ile Ile Lys Tyr Arg Arg Ile Phe Ile Glu Thr Leu Val Val
145                 150                 155                 160

Ser Val Phe Leu Gln Leu Phe Ala Leu Ile Thr Pro Leu Phe Phe Gln
            165                 170                 175

Val Val Met Asp Lys Val Leu Val His Arg Gly Phe Ser Thr Leu Asn
            180                 185                 190

Val Ile Thr Val Ala Leu Ser Val Val Val Phe Glu Ile Ile Leu
            195                 200                 205

Ser Gly Leu Arg Thr Tyr Ile Phe Ala His Ser Thr Ser Arg Ile Asp
    210                 215                 220

Val Glu Leu Gly Ala Lys Leu Phe Arg His Leu Leu Ala Leu Pro Ile
225                 230                 235                 240

Ser Tyr Phe Glu Ser Arg Arg Val Gly Asp Thr Val Ala Arg Val Arg
            245                 250                 255

Glu Leu Asp Gln Ile Arg Asn Phe Leu Thr Gly Gln Ala Leu Thr Ser
            260                 265                 270

Val Leu Asp Leu Leu Phe Ser Phe Ile Phe Phe Ala Val Met Trp Tyr
            275                 280                 285

Tyr Ser Pro Lys Leu Thr Leu Val Ile Leu Phe Ser Leu Pro Cys Tyr
    290                 295                 300

Ala Ala Trp Ser Val Phe Ile Ser Pro Ile Leu Arg Arg Arg Leu Asp
305                 310                 315                 320

Asp Lys Phe Ser Arg Asn Ala Asp Asn Gln Ser Phe Leu Val Glu Ser
            325                 330                 335

Val Thr Ala Ile Asn Thr Ile Lys Ala Met Ala Val Ser Pro Gln Met
            340                 345                 350

Thr Asn Ile Trp Asp Lys Gln Leu Ala Gly Tyr Val Ala Ala Gly Phe
            355                 360                 365

Lys Val Thr Val Leu Ala Thr Ile Gly Gln Gln Gly Ile Gln Leu Ile
    370                 375                 380

Gln Lys Thr Val Met Ile Ile Asn Leu Trp Leu Gly Ala His Leu Val
385                 390                 395                 400

Ile Ser Gly Asp Leu Ser Ile Gly Gln Leu Ile Ala Phe Asn Met Leu
            405                 410                 415
```

-continued

```
Ala Gly Gln Ile Val Ala Pro Val Ile Arg Leu Ala Gln Ile Trp Gln
            420                 425                 430

Asp Phe Gln Gln Val Gly Ile Ser Val Thr Arg Leu Gly Asp Val Leu
            435                 440                 445

Asn Ser Pro Thr Glu Ser Tyr His Gly Lys Leu Ala Leu Pro Glu Ile
            450                 455                 460

Asn Gly Asp Ile Thr Phe Arg Asn Ile Arg Phe Arg Tyr Lys Pro Asp
465                 470                 475                 480

Ser Pro Val Ile Leu Asp Asn Ile Asn Leu Ser Ile Lys Gln Gly Glu
                    485                 490                 495

Val Ile Gly Ile Val Gly Arg Ser Gly Ser Gly Lys Ser Thr Leu Thr
                    500                 505                 510

Lys Leu Ile Gln Arg Phe Tyr Ile Pro Glu Asn Gly Gln Val Leu Ile
            515                 520                 525

Asp Gly His Asp Leu Ala Leu Ala Asp Pro Asn Trp Leu Arg Arg Gln
            530                 535                 540

Val Gly Val Val Leu Gln Asp Asn Val Leu Leu Asn Arg Ser Ile Ile
545                 550                 555                 560

Asp Asn Ile Ser Leu Ala Asn Pro Gly Met Ser Val Glu Lys Val Ile
                    565                 570                 575

Tyr Ala Ala Lys Leu Ala Gly Ala His Asp Phe Ile Ser Glu Leu Arg
                    580                 585                 590

Glu Gly Tyr Asn Thr Ile Val Gly Glu Gln Gly Ala Gly Leu Ser Gly
            595                 600                 605

Gly Gln Arg Gln Arg Ile Ala Ile Ala Arg Ala Leu Val Asn Asn Pro
            610                 615                 620

Lys Ile Leu Ile Phe Asp Glu Ala Thr Ser Ala Leu Asp Tyr Glu Ser
625                 630                 635                 640

Glu His Ile Ile Met Arg Asn Met His Lys Ile Cys Lys Gly Arg Thr
                    645                 650                 655

Val Ile Ile Ile Ala His Arg Leu Ser Thr Val Lys Asn Ala Asp Arg
                    660                 665                 670

Ile Ile Val Met Glu Lys Gly Lys Ile Val Glu Gln Gly Lys His Lys
            675                 680                 685

Glu Leu Leu Ser Glu Pro Glu Ser Leu Tyr Ser Tyr Leu Tyr Gln Leu
            690                 695                 700

Gln Ser Asp
705

<210> SEQ ID NO 31
<211> LENGTH: 478
<212> TYPE: PRT
<213> ORGANISM: Escherichia coli

<400> SEQUENCE: 31

Met Lys Thr Trp Leu Met Gly Phe Ser Glu Phe Leu Leu Arg Tyr Lys
1               5                   10                  15

Leu Val Trp Ser Glu Thr Trp Lys Ile Arg Lys Gln Leu Asp Thr Pro
                20                  25                  30

Val Arg Glu Lys Asp Glu Asn Glu Phe Leu Pro Ala His Leu Glu Leu
            35                  40                  45

Ile Glu Thr Pro Val Ser Arg Arg Pro Arg Leu Val Ala Tyr Phe Ile
            50                  55                  60

Met Gly Phe Leu Val Ile Ala Val Ile Leu Ser Val Leu Gly Gln Val
65                  70                  75                  80
```

```
Glu Ile Val Ala Thr Ala Asn Gly Lys Leu Thr Leu Ser Gly Arg Ser
            85                  90                  95

Lys Glu Ile Lys Pro Ile Glu Asn Ser Ile Val Lys Glu Ile Ile Val
            100                 105                 110

Lys Glu Gly Glu Ser Val Arg Lys Gly Asp Val Leu Leu Lys Leu Thr
            115                 120                 125

Ala Leu Gly Ala Glu Ala Asp Thr Leu Lys Thr Gln Ser Ser Leu Leu
            130                 135                 140

Gln Thr Arg Leu Glu Gln Thr Arg Tyr Gln Ile Leu Ser Arg Ser Ile
145                 150                 155                 160

Glu Leu Asn Lys Leu Pro Glu Leu Lys Leu Pro Asp Glu Pro Tyr Phe
            165                 170                 175

Gln Asn Val Ser Glu Glu Glu Val Leu Arg Leu Thr Ser Leu Ile Lys
            180                 185                 190

Glu Gln Phe Ser Thr Trp Gln Asn Gln Lys Tyr Gln Lys Glu Leu Asn
            195                 200                 205

Leu Asp Lys Lys Arg Ala Glu Arg Leu Thr Ile Leu Ala Arg Ile Asn
            210                 215                 220

Arg Tyr Glu Asn Leu Ser Arg Val Glu Lys Ser Arg Leu Asp Asp Phe
225                 230                 235                 240

Arg Ser Leu Leu His Lys Gln Ala Ile Ala Lys His Ala Val Leu Glu
            245                 250                 255

Gln Glu Asn Lys Tyr Val Glu Ala Ala Asn Glu Leu Arg Val Tyr Lys
            260                 265                 270

Ser Gln Leu Glu Gln Ile Glu Ser Glu Ile Leu Ser Ala Lys Glu Glu
            275                 280                 285

Tyr Gln Leu Val Thr Gln Leu Phe Lys Asn Glu Ile Leu Asp Lys Leu
            290                 295                 300

Arg Gln Thr Thr Asp Ser Ile Glu Leu Leu Thr Leu Glu Leu Glu Lys
305                 310                 315                 320

Asn Glu Glu Arg Gln Gln Ala Ser Val Ile Arg Ala Pro Val Ser Gly
            325                 330                 335

Lys Val Gln Gln Leu Lys Val His Thr Glu Gly Gly Val Val Thr Thr
            340                 345                 350

Ala Glu Thr Leu Met Val Ile Val Pro Glu Asp Asp Thr Leu Glu Val
            355                 360                 365

Thr Ala Leu Val Gln Asn Lys Asp Ile Gly Phe Ile Asn Val Gly Gln
            370                 375                 380

Asn Ala Ile Ile Lys Val Glu Ala Phe Pro Tyr Thr Arg Tyr Gly Tyr
385                 390                 395                 400

Leu Val Gly Lys Val Lys Asn Ile Asn Leu Asp Ala Ile Glu Asp Gln
            405                 410                 415

Lys Leu Gly Leu Val Phe Asn Val Ile Val Ser Val Glu Glu Asn Asp
            420                 425                 430

Leu Ser Thr Gly Asn Lys His Ile Pro Leu Ser Ser Gly Met Ala Val
            435                 440                 445

Thr Ala Glu Ile Lys Thr Gly Met Arg Ser Val Ile Ser Tyr Leu Leu
            450                 455                 460

Ser Pro Leu Glu Glu Ser Val Thr Glu Ser Leu His Glu Arg
465                 470                 475
```

```
<210> SEQ ID NO 32
<211> LENGTH: 493
```

<212> TYPE: PRT
<213> ORGANISM: Escherichia coli

<400> SEQUENCE: 32

Met Lys Lys Leu Leu Pro Ile Leu Ile Gly Leu Ser Leu Ser Gly Phe
1               5                   10                  15

Ser Ser Leu Ser Gln Ala Glu Asn Leu Met Gln Val Tyr Gln Gln Ala
            20                  25                  30

Arg Leu Ser Asn Pro Glu Leu Arg Lys Ser Ala Ala Asp Arg Asp Ala
        35                  40                  45

Ala Phe Glu Lys Ile Asn Glu Ala Arg Ser Pro Leu Leu Pro Gln Leu
    50                  55                  60

Gly Leu Gly Ala Asp Tyr Thr Tyr Ser Asn Gly Tyr Arg Asp Ala Asn
65                  70                  75                  80

Gly Ile Asn Ser Asn Ala Thr Ser Ala Ser Leu Gln Leu Thr Gln Ser
                85                  90                  95

Ile Phe Asp Met Ser Lys Trp Arg Ala Leu Thr Leu Gln Glu Lys Ala
                100                 105                 110

Ala Gly Ile Gln Asp Val Thr Tyr Gln Thr Asp Gln Gln Thr Leu Ile
            115                 120                 125

Leu Asn Thr Ala Thr Ala Tyr Phe Asn Val Leu Asn Ala Ile Asp Val
    130                 135                 140

Leu Ser Tyr Thr Gln Ala Gln Lys Glu Ala Ile Tyr Arg Gln Leu Asp
145                 150                 155                 160

Gln Thr Thr Gln Arg Phe Asn Val Gly Leu Val Ala Ile Thr Asp Val
                165                 170                 175

Gln Asn Ala Arg Ala Gln Tyr Asp Thr Val Leu Ala Asn Glu Val Thr
            180                 185                 190

Ala Arg Asn Asn Leu Asp Asn Ala Val Glu Gln Leu Arg Gln Ile Thr
            195                 200                 205

Gly Asn Tyr Tyr Pro Glu Leu Ala Ala Leu Asn Val Glu Asn Phe Lys
    210                 215                 220

Thr Asp Lys Pro Gln Pro Val Asn Ala Leu Leu Lys Glu Ala Glu Lys
225                 230                 235                 240

Arg Asn Leu Ser Leu Leu Gln Ala Arg Leu Ser Gln Asp Leu Ala Arg
                245                 250                 255

Glu Gln Ile Arg Gln Ala Gln Asp Gly His Leu Pro Thr Leu Asp Leu
            260                 265                 270

Thr Ala Ser Thr Gly Ile Ser Asp Thr Ser Tyr Ser Gly Ser Lys Thr
            275                 280                 285

Arg Gly Ala Ala Gly Thr Gln Tyr Asp Asp Ser Asn Met Gly Gln Asn
    290                 295                 300

Lys Val Gly Leu Ser Phe Ser Leu Pro Ile Tyr Gln Gly Gly Met Val
305                 310                 315                 320

Asn Ser Gln Val Lys Gln Ala Gln Tyr Asn Phe Val Gly Ala Ser Glu
                325                 330                 335

Gln Leu Glu Ser Ala His Arg Ser Val Val Gln Thr Val Arg Ser Ser
            340                 345                 350

Phe Asn Asn Ile Asn Ala Ser Ile Ser Ser Ile Asn Ala Tyr Lys Gln
        355                 360                 365

Ala Val Val Ser Ala Gln Ser Ser Leu Asp Ala Met Glu Ala Gly Tyr
    370                 375                 380

Ser Val Gly Thr Arg Thr Ile Val Asp Val Leu Asp Ala Thr Thr Thr
385                 390                 395                 400

-continued

```
Leu Tyr Asn Ala Lys Gln Glu Leu Ala Asn Ala Arg Tyr Asn Tyr Leu
            405                 410                 415

Ile Asn Gln Leu Asn Ile Lys Ser Ala Leu Gly Thr Leu Asn Glu Gln
            420                 425                 430

Asp Leu Leu Ala Leu Asn Asn Ala Leu Ser Lys Pro Val Ser Thr Asn
        435                 440                 445

Pro Glu Asn Val Ala Pro Gln Thr Pro Glu Gln Asn Ala Ile Ala Asp
    450                 455                 460

Gly Tyr Ala Pro Asp Ser Pro Ala Pro Val Val Gln Gln Thr Ser Ala
465                 470                 475                 480

Arg Thr Thr Thr Ser Asn Gly His Asn Pro Phe Arg Asn
            485                 490
```

```
<210> SEQ ID NO 33
<211> LENGTH: 41
<212> TYPE: DNA
<213> ORGANISM: Artificial
<220> FEATURE:
<223> OTHER INFORMATION: oligonucleotide primer

<400> SEQUENCE: 33
catttaatta cctcttaacc agttaatgaa aaattaaaat c                    41

<210> SEQ ID NO 34
<211> LENGTH: 21
<212> TYPE: DNA
<213> ORGANISM: Artificial
<220> FEATURE:
<223> OTHER INFORMATION: oligonucleotide primer

<400> SEQUENCE: 34
aggaactggt ttgaaaaaga g                                          21

<210> SEQ ID NO 35
<211> LENGTH: 33
<212> TYPE: DNA
<213> ORGANISM: Artificial
<220> FEATURE:
<223> OTHER INFORMATION: oligonucleotide primer

<400> SEQUENCE: 35
caaactgagt ttatcatcaa gcagatctgc ccc                            33

<210> SEQ ID NO 36
<211> LENGTH: 22
<212> TYPE: DNA
<213> ORGANISM: Artificial
<220> FEATURE:
<223> OTHER INFORMATION: oligonucleotide primer

<400> SEQUENCE: 36
ttagcctatg gaagtcaggg tg                                         22

<210> SEQ ID NO 37
<211> LENGTH: 34
<212> TYPE: DNA
<213> ORGANISM: Artificial
<220> FEATURE:
<223> OTHER INFORMATION: oligonucleotide primer

<400> SEQUENCE: 37
gataaactca gtttggctga tattgatttc cggg                           34
```

```
<210> SEQ ID NO 38
<211> LENGTH: 34
<212> TYPE: DNA
<213> ORGANISM: Artificial
<220> FEATURE:
<223> OTHER INFORMATION: oligonucleotide primer

<400> SEQUENCE: 38
acttccatag gctaatttaa gggaatcagg tgtg                                  34

<210> SEQ ID NO 39
<211> LENGTH: 34
<212> TYPE: PRT
<213> ORGANISM: Artificial
<220> FEATURE:
<223> OTHER INFORMATION: peptide of interest

<400> SEQUENCE: 39

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 40
<211> LENGTH: 7
<212> TYPE: PRT
<213> ORGANISM: Artificial
<220> FEATURE:
<223> OTHER INFORMATION: TEV cleavage site
<220> FEATURE:
<221> NAME/KEY: MISC_FEATURE
<222> LOCATION: (7)..(7)
<223> OTHER INFORMATION: Xaa is G, S, A, M or C, preferably G or S

<400> SEQUENCE: 40

Glu Asn Leu Tyr Phe Gln Xaa
1               5
```

VARIANTS OF HlyA AND USES THEREOF

CROSS-REFERENCE TO RELATED APPLICATION

The present application is a national stage entry according to 35 U.S.C. § 371 of PCT application No.: PCT/EP2021/056949 filed on Mar. 18, 2021; which claims priority to European patent application 20163961.4 filed on Mar. 18, 2020 and also claims priority to European patent application 20168779.5 filed on Apr. 8, 2020; all of which are incorporated herein by reference in their entirety and for all purposes.

REFERENCE TO A SEQUENCE LISTING SUBMITTED VIA EFS-WEB

The content of the ASCII text file of the sequence listing named "P85673US_seq_ST25", which is 67,737 bytes in size was created on Mar. 18, 2020; the sequence listing is electronically submitted via EFS-Web herewith and is herein incorporated by reference in its entirety.

TECHNICAL FIELD

The present disclosure lies in the field of molecular biology, recombinant peptide and protein expression and relates to amino acid sequences comprising hemolysin A (HlyA) variants to improve the solubility and/or stability of a fusion construct of said variants and a peptide or protein of interest.

BACKGROUND

To date, recombinant protein/enzyme production for use in industrial processes is widely established. It is expected that in the future more and more industrial processes that are currently based on traditional chemistry will be adapted to involve recombinant technologies.

Type 1 secretion systems (T1 SS), which mostly occur in Gram-negative bacteria, have been described as means to allow efficient peptide and protein expression and/or secretion (See, e.g., international patent publications WO 2013/057312 A1 and WO 20141170430 A1). Among the family of T1 SS the hemolysin (Hly) T1 SS involving HlyA as transport substrate is of particular interest, as it is devoid of any proteolytic activity and thus does not degrade the secreted peptide or protein of interest. The hemolysin (Hly) T1 SS of *E. coli* consists of the inner membrane protein HlyB, which is an ATP binding cassette (ABC) transporter, the outer membrane protein TolC and the membrane fusion-protein HlyD in the inner membrane. The interacting substrate HlyA is exported through the hemolysin secretion system in an ATP dependent manner. Both WO 2013/057312 A1 and WO 20141170430 A1 describe the industrial use of the Hly 1 SS.

While the technologies based on the Hly 1 SS, in particular fusion proteins of peptides and proteins to be expressed with HlyA or a defined fragment thereof termed HlyA1 (SEQ ID NO:1) are known in the art, in particular from the international patent publications cited above, and are commercially available, it has been found that in various instances high yields are prevented by suboptimal solubility or susceptibility to proteolysis of the fusion constructs. Thus, there still exists need for further optimized methods that allow more efficient production of peptides and proteins that overcome some of the drawbacks of existing methods.

SUMMARY

The present disclosure is based on the inventor's surprising finding that variants of the known HlyA fragment termed "HlyA1" (having the amino acid set forth in SEQ ID NO:1) that comprise one or more amino acid substitutions or deletions as defined herein when fused to a peptide or protein of interest that is to be recombinantly produced by expression of a fusion protein in a host cell provide for increased stability (decreased proteolytic sensitivity) and/or solubility as well as similar or even increased expression rates and thus allow higher yields of the desired (fused) product. It has further been found that certain variants described herein additionally exhibit increased renaturation efficiency.

In a first aspect, an isolated polypeptide may have or include a first amino acid sequence, wherein the first amino acid sequence has at least 80%, at least 85%, at least 90%, at least 95%, at least 97.5%, at least 99% or at least 99.5% sequence identity over its entire length with the amino acid sequence set forth in SEQ ID NO:1 (HlyA1) and comprises one or more amino acid substitution(s) or deletion(s) in any one of the positions corresponding to positions 161, 162, 163, 165, 171, 176, 179, 180, 181, 186, 187, 188, 190, 191, 192, 193, 194, 195, 196, 197, 198, 199, 200, 201, 205, 206, 209, 210, 212, and 218 of SEQ ID NO:1 or fragments thereof. Said first amino acid sequence derived from SEQ ID NO:1 by one or more amino acid substitution(s) or deletion (s) is also referred to herein as "variant" or "HlyA1 variant" or "variant of SEQ ID NO:1".

In various embodiments, the variant comprises one or more amino acid substitution(s) or deletion(s) in any one of the positions corresponding to positions 162, 165, 171, 179, 188, 190, 191, 193, 194, 198, 199, 201, 205, 209, 212, and 218 of SEQ ID NO:1 or fragments thereof.

In various embodiments, the variant comprises any one or more of the amino acid substitution(s): 161T, 162E, 162C, 163D, 165M, 171D, 176C, 179D, 179C, 180D, 181C, 186D, 187C, 187P, 188H, 190Q, 190A, 191D, 191E, 191G, 191H, 191P, 192P, 193D, 193E, 193C, 193P, 193L, 193H, 194T, 194V, 194I, 194P, 195S, 196G, 197G, 198E, 198P, 199D, 199P, 200S, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 161T, 162E, 162C, 163D, 165M, 171D, 176C, 179D, 179C, 180D, 181C, 186D, 187C, 187P, 188H, 190Q, 190A, 191D, 191E, 191G, 191H, 191P, 193D, 193E, 193C, 193P, 193L, 193H, 194T, 194V, 194I, 194P, 195S, 196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 161T, 162E, 162C, 163D, 165M, 171D, 176C, 179D, 179C, 180D, 181C, 186D, 187C, 187P, 188H, 190Q, 190A, 191E, 191D, 191H, 191P, 193E, 193C, 193P, 193L, 193H, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 162C, 165M, 171D, 179D, 188H, 190Q, 191D, 191E, 193E, 193P, 194, 194P, 198E, 198P, 199D, 201P, 205C, 205S, 209T, 209G, 212D, 218D, 218H and 218C.

In various embodiments, the variants do not comprise any one or more of the following substitutions: 163N, 176L, 193M, 193W, and 200S.

In various embodiments, the variant comprises any one or more of the amino acid deletions: □187, 190, □191, □192, and □209.

In various embodiments, the variant comprises any two or more, three or more, four or more, five or more, six or more, seven or more, eight or more, nine or more, ten or more, 11 or more, 12 or more, 13, or more, 14 or more, 15, or more, 16 or more, 17 or more, 18 or more, 19 or more, 20 or more, 21 or more, 22 or more, 23 or more, 24 or more, 25 or more, 26 or more, 27 or more, 28 or more, 29 or all 30 of the amino acid substitution(s): 161T, 162E, 162C, 163N, 165M, 171D, 176C, 179D, 179C, 180D, 181C, 186D, 187C, 187P, 188H, 190Q, 190A, 191E, 191D, 191H, 191P, 193E, 193C, 193P, 193L, 193H, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises at least 2, at least 3, at least 4, at least 5, at least 6, at least 7, at least 8, at least 9, at least 10, at least 11, at least 12, at least 13, at least 14 or all 15 of the amino acid substitution(s): 162C, 165M, 171D, 179D, 188H, 190Q, 191D, 191E, 193E, 193P, 194, 194P, 198E, 198P, 199D, 201P, 205C, 205S, 209T, 209G, 212D, 218D, 218H and 218C.

In various embodiments, the variant comprises any one or more of the substitutions defined above and one or more of the deletions defined above.

In various embodiments, the variant comprises amino acid substitutions/deletions in the following positions (using the numbering of SEQ ID NO:1):

162 and 165; 162 and 171; 162 and 179; 162 and 188; 162 and 190; 162 and 191; 162 and 193; 162 and 194; 162 and 198; 162 and 199; 162 and 201; 162 and 205; 162 and 209; 162 and 212; 162 and 218; 165 and 171; 165 and 179; 165 and 188; 165 and 190; 165 and 191; 165 and 193; 165 and 194; 165 and 198; 165 and 199; 165 and 201; 165 and 205; 165 and 209; 165 and 212; 165 and 218; 171 and 179; 171 and 188; 171 and 190; 171 and 191; 171 and 193; 171 and 194; 171 and 198; 171 and 199; 171 and 201; 171 and 205; 171 and 209; 171 and 212; 171 and 218; 179 and 188; 179 and 190; 179 and 191; 179 and 193; 179 and 194; 179 and 198; 179 and 199; 179 and 201; 179 and 205; 179 and 209; 179 and 212; 179 and 218; 188 and 190; 188 and 191; 188 and 193; 188 and 194; 188 and 198; 188 and 199; 188 and 201; 188 and 205; 188 and 209; 188 and 212; 188 and 218; 190 and 191; 190 and 193; 190 and 194; 190 and 198; 190 and 199; 190 and 201; 190 and 205; 190 and 209; 190 and 212; 190 and 218; 191 and 193; 191 and 194; 191 and 198; 191 and 199; 191 and 201; 191 and 205; 191 and 209; 191 and 212; 191 and 218; 193 and 194; 193 and 198; 193 and 199; 193 and 201; 193 and 205; 193 and 209; 193 and 212; 193 and 218; 194 and 198; 194 and 199; 194 and 201; 194 and 205; 194 and 209; 194 and 212; 194 and 218; 198 and 199; 198 and 201; 198 and 205; 198 and 209; 198 and 212; 198 and 218; 199 and 201; 199 and 205; 199 and 209; 199 and 212; 199 and 218; 201 and 205; 201 and 209; 201 and 212; 201 and 218; 205 and 209; 205 and 212; 205 and 218; 209 and 212; 209 and 218; 212 and 218; 162, 165 and any one of 171, 179, 188, 190, 191, 193, 194, 198, 199, 201, 205, 209, 212 and 218; 162, 171 and any one of 179, 188, 190, 191, 193, 194, 198, 199, 201, 205, 209, 212 and 218; 162, 179 and any one of 188, 190, 191, 193, 194, 198, 199, 201, 205, 209, 212 and 218; 162, 188 and any one of 190, 191, 193, 194, 198, 199, 201, 205, 209, 212 and 218; 162, 190 and any one of 191, 193, 194, 198, 199, 201, 205, 209, 212 and 218; 162, 191 and any one of 193, 194, 198, 199, 201, 205, 209, 212 and 218; 162, 193 and any one of 194, 198, 199, 201, 205, 209, 212 and 218; 162, 194 and any one of 198, 199, 201, 205, 209, 212 and 218; 162, 198 and any one of 199, 201, 205, 209, 212 and 218; 162, 199 and any one of 201, 205, 209, 212 and 218; 162, 201 and any one of 205, 209, 212 and 218; 162, 205 and any one of 209, 212 and 218; 162, 209 and any one of 212 and 218; 162, 212 and 218;

165, 171 and any one of 179, 188, 190, 191, 193, 194, 198, 199, 201, 205, 209, 212 and 218; 165, 179 and any one of 188, 190, 191, 193, 194, 198, 199, 201, 205, 209, 212 and 218; 165, 188 and any one of 190, 191, 193, 194, 198, 199, 201, 205, 209, 212 and 218; 165, 190 and any one of 191, 193, 194, 198, 199, 201, 205, 209, 212 and 218; 165, 191 and any one of 193, 194, 198, 199, 201, 205, 209, 212 and 218; 165, 193 and any one of 194, 198, 199, 201, 205, 209, 212 and 218; 165, 194 and any one of 198, 199, 201, 205, 209, 212 and 218; 165, 198 and any one of 199, 201, 205, 209, 212 and 218; 165, 199 and any one of 201, 205, 209, 212 and 218; 165, 201 and any one of 205, 209, 212 and 218; 165, 205 and any one of 209, 212 and 218; 165, 209 and any one of 212 and 218; 165, 212 and 218;

171, 179 and any one of 188, 190, 191, 193, 194, 198, 199, 201, 205, 209, 212 and 218; 171, 188 and any one of 190, 191, 193, 194, 198, 199, 201, 205, 209, 212 and 218; 171, 190 and any one of 191, 193, 194, 198, 199, 201, 205, 209, 212 and 218; 171, 191 and any one of 193, 194, 198, 199, 201, 205, 209, 212 and 218; 171, 193 and any one of 194, 198, 199, 201, 205, 209, 212 and 218; 171, 194 and any one of 198, 199, 201, 205, 209, 212 and 218; 171, 198 and any one of 199, 201, 205, 209, 212 and 218; 171, 199 and any one of 201, 205, 209, 212 and 218; 171, 201 and any one of 205, 209, 212 and 218; 171, 205 and any one of 209, 212 and 218; 171, 209 and any one of 212 and 218; 171, 212 and 218;

179, 188 and any one of 190, 191, 193, 194, 198, 199, 201, 205, 209, 212 and 218; 179, 190 and any one of 191, 193, 194, 198, 199, 201, 205, 209, 212 and 218; 179, 191 and any one of 193, 194, 198, 199, 201, 205, 209, 212 and 218; 179, 193 and any one of 194, 198, 199, 201, 205, 209, 212 and 218; 179, 194 and any one of 198, 199, 201, 205, 209, 212 and 218; 179, 198 and any one of 199, 201, 205, 209, 212 and 218; 179, 199 and any one of 201, 205, 209, 212 and 218; 179, 201 and any one of 205, 209, 212 and 218; 179, 205 and any one of 209, 212 and 218; 179, 209 and any one of 212 and 218; 179, 212 and 218;

188, 190 and any one of 191, 193, 194, 198, 199, 201, 205, 209, 212 and 218; 188, 191 and any one of 193, 194, 198, 199, 201, 205, 209, 212 and 218; 188, 193 and any one of 194, 198, 199, 201, 205, 209, 212 and 218; 188, 194 and any one of 198, 199, 201, 205, 209, 212 and 218; 188, 198 and any one of 199, 201, 205, 209, 212 and 218; 188, 199 and any one of 201, 205, 209, 212 and 218; 188, 201 and any one of 205, 209, 212 and 218; 188, 205 and any one of 209, 212 and 218; 188, 209 and any one of 212 and 218; 188, 212 and 218;

190, 191 and any one of 193, 194, 198, 199, 201, 205, 209, 212 and 218; 190, 193 and any one of 194, 198, 199, 201, 205, 209, 212 and 218; 190, 194 and any one of 198, 199, 201, 205, 209, 212 and 218; 190, 198 and any one of 199, 201, 205, 209, 212 and 218; 190, 199 and any one of 201, 205, 209, 212 and 218; 190, 201 and any one of 205, 209, 212 and 218; 190, 205 and any one of 209, 212 and 218; 190, 209 and any one of 212 and 218; 190, 212 and 218;

191, 193 and any one of 194, 198, 199, 201, 205, 209, 212 and 218; 191, 194 and any one of 198, 199, 201, 205, 209, 212 and 218; 191, 198 and any one of 199, 201, 205, 209, 212 and 218; 191, 199 and any one of 201, 205, 209, 212 and 218; 191, 201 and any one of 205, 209, 212 and 218; 191, 205 and any one of 209, 212 and 218; 191, 209 and any one of 212 and 218; 191, 212 and 218;

193, 194 and any one of 198, 199, 201, 205, 209, 212 and 218; 193, 198 and any one of 199, 201, 205, 209, 212 and 218; 193, 199 and any one of 201, 205, 209, 212 and 218; 193, 201 and any one of 205, 209, 212 and 218; 193, 205 and any one of 209, 212 and 218; 193, 209 and any one of 212 and 218; 193, 212 and 218;

194, 198 and any one of 199, 201, 205, 209, 212 and 218; 194, 199 and any one of 201, 205, 209, 212 and 218; 194, 201 and any one of 205, 209, 212 and 218; 194, 205 and any one of 209, 212 and 218; 194, 209 and any one of 212 and 218; 194, 212 and 218;

198, 199 and any one of 201, 205, 209, 212 and 218; 198, 201 and any one of 205, 209, 212 and 218; 198, 205 and any one of 209, 212 and 218; 198, 209 and any one of 212 and 218; 198, 212 and 218; 199, 201 and any one of 205, 209, 212 and 218; 199, 205 and any one of 209, 212 and 218; 199, 209 and any one of 212 and 218; 199, 212 and 218; 201, 205 and any one of 209, 212 and 218; 201, 209 and any one of 212 and 218; 201, 212 and 218; 205, 209 and any one of 212 and 218; 205, 212 and 218; 209, 212 and 218;

In any of the above embodiments, the substitutions may be selected from 162C, 165M, 171D, 179D, 188H, 190Q, 191D, 191E, 193E, 193P, 194, 194P, 198E, 198P, 199D, 201P, 205C, 205S, 209T, 209G, 212D, 218H and 218C. The deletions may be selected from del187, del190, and del209.

In various embodiments, any of the afore-mentioned variants may additionally comprise one or more amino acid substitutions/deletions in the positions corresponding to positions 161, 163, 176, 180, 181, 186, 187, 196, 197, 206, and 210 of SEQ ID NO:1.

In various embodiments, the variant comprises the amino acid substitution(s):

162C and 165M; 162C and 171D; 162C and 179D; 162CC and 188H; 162C and 190Q; 162C and 191D/E; 162C and 193E/P; 162C and 194P/I; 162C and 198E/P; 162C and 199D; 162C and 201P; 162C and 205C/S; 162C and 209T/ G; 162C and 212D; 162C and 218D/H/C; 165M and 171D; 165M and 179D; 165M and 188H; 165M and 190Q; 165M and 191D/E; 165M and 193E/P; 165M and 194P/I; 165M and 198E/P; 165M and 199D; 165M and 201P; 165M and 205C/S; 165M and 209T/G; 165M and 212D; 165M and 218D/H/C; 171D and 179D; 171D and 188H; 171D and 190Q; 171D and 191D/E; 171D and 193E/P; 171D and 194P/I; 171D and 198E/P; 171D and 199D; 171D and 201P; 171D and 205C/S; 171D and 209T/G; 171D and 212D; 171D and 218D/H/C; 179D and 188H; 179D and 190Q; 179D and 191D/E; 179D and 193E/P; 179D and 194P/I; 179D and 198E/P; 179D and 199D; 179D and 201P; 179D and 205C/S; 179D and 209T/G; 179D and 212D; 179D and 218D/H/C; 188H and 190Q; 188H and 191D/E; 188H and 193E/P; 188H and 194P/I; 188H and 198E/P; 188H and 199D; 188H and 201P; 188H and 205C/S; 188H and 209T/ G; 188H and 212D; 188H and 218D/H/C; 190Q and 191D/ E; 190Q and 193E/P; 190Q and 194P/I; 190Q and 198E/P; 190Q and 199D; 190Q and 201P; 190Q and 205C/S; 190Q and 209T/G; 190Q and 212D; 190Q and 218D/H/C; 191 D/E and 193E/P; 191D/E and 194P/I; 191D/E and 198E/P; 191D/E and 199D; 191D/E and 201P; 191D/E and 205C/S;

191D/E and 209T/G; 191D/E and 212D; 191D/E and 218D/ H/C; 193E/P and 194P/I; 193E/P and 198E/P; 193E/P and 199D; 193E/P and 201P; 193E/P and 205C/S; 193E/P and 209T/G; 193E/P and 212D; 193E/P and 218D/H/C; 194P/I and 198E/P; 194P/I and 199D; 194P/I and 201P; 194P/I and 205C/S; 194P/I and 209T/G; 194P/I and 212D; 194P/I and 218D/H/C; 198E/P and 199D; 198E/P and 201P; 198E/P and 205C/S; 198E/P and 209T/G; 198E/P and 212D; 198E/P and 218D/H/C; 199D and 201P; 199D and 205C/S; 199D and 209T/G; 199D and 212D; 199D and 218D/H/C; 201P and 205C/S; 201P and 209T/G; 201P and 212D; 201P and 218D/H/C; 205C/S and 209T/G; 205C/S and 212D; 205C/S and 218D/H/C; 209T/G and 212D; 209T/G and 218D/H/C; 212D and 218D/H/C;

162C, 165M and any one of 171D, 179D, 188H, 190Q, 191D/E, 193E/P, 194P/I, 198E/P, 199D, 201P, 205C/S, 209T/G, 212D and 218D/H/C; 162C, 171D and any one of 179D, 188H, 190Q, 191D/E, 193E/P, 194P/I, 198E/P, 199D, 201P, 205C/S, 209T/G, 212D and 218D/H/C; 162C, 179D and any one of 188H, 190Q, 191D/E, 193E/P, 194P/I, 198E/P, 199D, 201P, 205C/S, 209T/G, 212D and 218D/H/C; 162C, 188H and any one of 190Q, 191D/E, 193E/P, 194P/I, 198E/P, 199D, 201P, 205C/S, 209T/G, 212D and 218D/H/C; 162C, 190Q and any one of 191 D/E, 193E/P, 194P/I, 198E/P, 199D, 201P, 205C/S, 209T/G, 212D and 218D/H/C; 162C, 191D/E and any one of 193E/P, 194P/I, 198E/P, 199D, 201P, 205C/S, 209T/G, 212D and 218D/H/C; 162C, 193E/P and any one of 194P/I, 198E/P, 199D, 201P, 205C/S, 209T/G, 212D and 218D/H/C; 162C, 194P/I and any one of 198E/P, 199D, 201P, 205C/S, 209T/G, 212D and 218D/H/C; 162C, 198E/P and any one of 199D, 201P, 205C/S, 209T/G, 212D and 218D/H/C; 162C, 199D and any one of 201P, 205C/S, 209T/G, 212D and 218D/H/C; 162C, 201P and any one of 205C/S, 209T/G, 212D and 218D/H/C; 162C, 205C/S and any one of 209T/G, 212D and 218D/H/C; 162C, 209T/G and any one of 212D and 218D/H/C; 162C, 212D and 218D/H/C;

165M, 171D and any one of 179D, 188H, 190Q, 191D/E, 193E/P, 194P/I, 198E/P, 199D, 201P, 205C/S, 209T/G, 212D and 218D/H/C; 165M, 179D and any one of 188H, 190Q, 191D/E, 193E/P, 194P/I, 198E/P, 199D, 201P, 205C/S, 209T/G, 212D and 218D/H/C; 165M, 188H and any one of 190Q, 191D/E, 193E/P, 194P/I, 198E/P, 199D, 201P, 205C/ S, 209T/G, 212D and 218D/H/C; 165M, 190Q and any one of 191D/E, 193E/P, 194P/I, 198E/P, 199D, 201P, 205C/S, 209T/G, 212D and 218D/H/C; 165M, 191D/E and any one of 193E/P, 194P/I, 198E/P, 199D, 201P, 205C/S, 209T/G, 212D and 218D/H/C; 165M, 193E/P and any one of 194P/I, 198E/P, 199D, 201P, 205C/S, 209T/G, 212D and 218D/H/C; 165M, 194P/I and any one of 198E/P, 199D, 201P, 205C/S, 209T/G, 212D and 218D/H/C; 165M, 198E/P and any one of 199D, 201P, 205C/S, 209T/G, 212D and 218D/H/C; 165M, 199D and any one of 201P, 205C/S, 209T/G, 212D and 218D/H/C; 165M, 201P and any one of 205C/S, 209T/ G, 212D and 218D/H/C; 165M, 205C/S and any one of 209T/G, 212D and 218D/H/C; 165M, 209T/G and any one of 212D and 218D/H/C; 165M, 212D and 218D/H/C;

171D, 179D and any one of 188H, 190Q, 191D/E, 193E/P, 194P/I, 198E/P, 199D, 201P, 205C/S, 209T/G, 212D and 218D/H/C; 171D, 188H and any one of 190Q, 191D/E, 193E/P, 194P/I, 198E/P, 199D, 201P, 205C/S, 209T/G, 212D and 218D/H/C; 171D, 190Q and any one of 191D/E, 193E/P, 194P/I, 198E/P, 199D, 201P, 205C/S, 209T/G, 212D and 218D/H/C; 171D, 191D/E and any one of 193E/P, 194P/I, 198E/P, 199D, 201P, 205C/S, 209T/G, 212D and 218D/H/C; 171D, 193E/P and any one of 194P/I, 198E/P, 199D, 201P, 205C/S, 209T/G, 212D and 218D/H/C; 171D, 194P/I and any one of 198E/P, 199D, 201P, 205C/S, 209T/G, 212D and 218D/H/C; 171D, 198E/P and any one of 199D, 201P, 205C/S, 209T/G, 212D and 218D/H/C; 171D, 199D and any one of 201P, 205C/S, 209T/G, 212D and 218D/H/C; 171D, 201P and any one of 205C/S, 209T/G, 212D and 218D/H/C; 171D, 205C/S and any one of 209T/G, 212D and 218D/H/C; 171D, 209T/G and any one of 212D and 218D/H/C; 171D, 212D and 218D/H/C;

179D, 188H and any one of 190Q, 191D/E, 193E/P, 194P/I, 198E/P, 199D, 201P, 205C/S, 209T/G, 212D and 218D/H/C; 179D, 190Q and any one of 191D/E, 193E/P, 194P/I, 198E/P, 199D, 201P, 205C/S, 209T/G, 212D and 218D/H/C; 179D, 191D/E and any one of 193E/P, 194P/I, 198E/P, 199D, 201P, 205C/S, 209T/G, 212D and 218D/H/C; 179D, 193E/P and any one of 194P/I, 198E/P, 199D, 201P, 205C/S, 209T/G, 212D and 218D/H/C; 179D, 194P/I and any one of 198E/P, 199D, 201P, 205C/S, 209T/G, 212D and 218D/H/C; 179D, 198E/P and any one of 199D, 201P, 205C/S, 209T/G, 212D and 218D/H/C; 179D, 199D and any one of 201P, 205C/S, 209T/G, 212D and 218D/H/C; 179D, 201P and any one of 205C/S, 209T/G, 212D and 218D/H/C; 179D, 205C/S and any one of 209T/G, 212D and 218D/H/C; 179D, 209T/G and any one of 212D and 218D/H/C; 179D, 212D and 218D/H/C; 188H, 190Q and any one of 191D/E, 193E/P, 194P/I, 198E/P, 199D, 201P, 205C/S, 209T/G, 212D and 218D/H/C; 188H, 191D/E and any one of 193E/P, 194P/I, 198E/P, 199D, 201P, 205C/S, 209T/G, 212D and 218D/H/C; 188H, 193E/P and any one of 194P/I, 198E/P, 199D, 201P, 205C/S, 209T/G, 212D and 218D/H/C; 188H, 194P/I and any one of 198E/P, 199D, 201P, 205C/S, 209T/G, 212D and 218D/H/C; 188H, 198E/P and any one of 199D, 201P, 205C/S, 209T/G, 212D and 218D/H/C; 188H, 199D and any one of 201P, 205C/S, 209T/G, 212D and 218D/H/C; 188H, 201P and any one of 205C/S, 209T/G, 212D and 218D/H/C; 188H, 205C/S and any one of 209T/G, 212D and 218D/H/C; 188H, 209T/G and any one of 212D and 218D/H/C; 188H, 212D and 218D/H/C;

190Q, 191D/E and any one of 193E/P, 194P/I, 198E/P, 199D, 201P, 205C/S, 209T/G, 212D and 218D/H/C; 190Q, 193E/P and any one of 194P/I, 198E/P, 199D, 201P, 205C/S, 209T/G, 212D and 218D/H/C; 190Q, 194P/I and any one of 198E/P, 199D, 201P, 205C/S, 209T/G, 212D and 218D/H/C; 190Q, 198E/P and any one of 199D, 201P, 205C/S, 209T/G, 212D and 218D/H/C; 190Q, 199D and any one of 201P, 205C/S, 209T/G, 212D and 218D/H/C; 190Q, 201P and any one of 205C/S, 209T/G, 212D and 218D/H/C; 190Q, 205C/S and any one of 209T/G, 212D and 218D/H/C; 190Q, 209T/G and any one of 212D and 218D/H/C; 190Q, 212D and 218D/H/C;

191D/E, 193E/P and any one of 194P/I, 198E/P, 199D, 201P, 205C/S, 209T/G, 212D and 218D/H/C; 191D/E, 194P/I and any one of 198E/P, 199D, 201P, 205C/S, 209T/G, 212D and 218D/H/C; 191D/E, 198E/P and any one of 199D, 201P, 205C/S, 209T/G, 212D and 218D/H/C; 191D/E, 199D and any one of 201P, 205C/S, 209T/G, 212D and 218D/H/C; 191D/E, 201P and any one of 205C/S, 209T/G, 212D and 218D/H/C; 191D/E, 205C/S and any one of 209T/G, 212D and 218D/H/C; 191D/E, 209T/G and any one of 212D and 218D/H/C; 191D/E, 212D and 218D/H/C;

193E/P, 194P/I and any one of 198E/P, 199D, 201P, 205C/S, 209T/G, 212D and 218D/H/C; 193E/P, 198E/P and any one of 199D, 201P, 205C/S, 209T/G, 212D and 218D/H/C; 193E/P, 199D and any one of 201P, 205C/S, 209T/G, 212D and 218D/H/C; 193E/P, 201P and any one of 205C/S, 209T/G, 212D and 218D/H/C; 193E/P, 205C/S and any one of 209T/G, 212D and 218D/H/C; 193E/P, 209T/G and any one of 212D and 218D/H/C; 193E/P, 212D and 218D/H/C;

194P/I, 198E/P and any one of 199D, 201P, 205C/S, 209T/G, 212D and 218D/H/C; 194P/I, 199D and any one of 201P, 205C/S, 209T/G, 212D and 218D/H/C; 194P/I, 201P and any one of 205C/S, 209T/G, 212D and 218D/H/C; 194P/I, 205C/S and any one of 209T/G, 212D and 218D/H/C; 194P/I, 209T/G and any one of 212D and 218D/H/C; 194P/I, 212D and 218D/H/C;

198E/P, 199D and any one of 201P, 205C/S, 209T/G, 212D and 218D/H/C; 198E/P, 201P and any one of 205C/S, 209T/G, 212D and 218D/H/C; 198E/P, 205C/S and any one of 209T/G, 212D and 218D/H/C; 198E/P, 209T/G and any one of 212D and 218D/H/C; 198E/P, 212D and 218D/H/C; 199D, 201P and any one of 205C/S, 209T/G, 212D and 218D/H/C; 199D, 205C/S and any one of 209T/G, 212D and 218D/H/C; 199D, 209T/G and any one of 212D and 218D/H/C; 199D, 212D and 218D/H/C;

201P, 205C/S and any one of 209T/G, 212D and 218D/H/C; 201P, 209T/G and any one of 212D and 218D/H/C; 201P, 212D and 218D/H/C; 205C/S, 209T/G and any one of 212D and 218D/H/C; 205C/S, 212D and 218D/H/C; 209T/G, 212D and 218D/H/C;

In various embodiments, the variant comprises the amino acid substitution(s):

162C and 165M; 162C and 171D; 162C and 179D; 162C and 188H; 162C and 190Q; 162C and 191E; 162C and 193P; 162C and 194P; 162C and 198P; 162C and 199D; 162C and 201P; 162C and 205C; 162C and 209T/G; 162C and 212D; 162C and 218H/C; 165M and 171D; 165M and 179D; 165M and 188H; 165M and 190Q; 165M and 191E; 165M and 193P; 165M and 194P; 165M and 198P; 165M and 199D; 165M and 201P; 165M and 205C; 165M and 209T/G; 165M and 212D; 165M and 218H/C; 171D and 179D; 171D and 188H; 171D and 190Q; 171D and 191E; 171D and 193P; 171D and 194P; 171D and 198P; 171D and 199D; 171D and 201P; 171D and 205C; 171D and 209T/G; 171D and 212D; 171 D and 218H/C; 179D and 188H; 179D and 190Q; 179D and 191E; 179D and 193P; 179D and 194P; 179D and 198P; 179D and 199D; 179D and 201P; 179D and 205C; 179D and 209T/G; 179D and 212D; 179D and 218H/C; 188H and 190Q; 188H and 191E; 188H and 193P; 188H and 194P; 188H and 198P; 188H and 199D; 188H and 201P; 188H and 205C; 188H and 209T/G; 188H and 212D; 188H and 218H/C; 190Q and 191E; 190Q and 193P; 190Q and 194P; 190Q and 198P; 190Q and 199D; 190Q and 201P; 190Q and 205C; 190Q and 209T/G; 190Q and 212D; 190Q and 218H/C; 191E and 193P; 191E and 194P; 191E and 198P; 191E and 199D; 191E and 201P; 191E and 205C; 191E and 209T/G; 191E and 212D; 191E and 218H/C; 193P and 194P; 193P and 198P; 193P and 199D; 193P and 201P; 193P and 205C; 193P and 209T/G; 193P and 212D; 193P and 218H/C; 194P and 198P; 194P and 199D; 194P and 201P; 194P and 205C; 194P and 209T/G; 194P and 212D; 194P and 218H/C; 198P and 199D; 198P and 201P; 198P and 205C; 198P and 209T/G; 198P and 212D; 198P and 218H/C; 199D and 201P; 199D and 205C; 199D and 209T/G; 199D and 212D; 199D and 218H/C; 201P and 205C; 201P and 209T/G; 201P and 212D; 201P and 218H/C; 205C and 209T/G; 205C and 212D; 205C and 218H/C; 209T/G and 212D; 209T/G and 218H/C; 212D and 218H/C;

162C, 165M and any one of 171D, 179D, 188H, 190Q, 191E, 193P, 194P, 198P, 199D, 201P, 205C, 209T/G, 212D and 218H/C; 162C, 171D and any one of 179D, 188H, 190Q, 191E, 193P, 194P, 198P, 199D, 201P, 205C, 209T/G, 212D and 218H/C; 162C, 179D and any one of 188H, 190Q, 191E, 193P, 194P, 198P, 199D, 201P, 205C, 209T/G, 212D and 218H/C; 162C, 188H and any one of 190Q, 191E, 193P, 194P, 198P, 199D, 201P, 205C, 209T/G, 212D and 218H/C; 162C, 190Q and any one of 191E, 193P, 194P, 198P, 199D, 201P, 205C, 209T/G, 212D and 218H/C; 162C, 191E and any one of 193P, 194P, 198P, 199D, 201P, 205C, 209T/G, 212D and 218H/C; 162C, 193P and any one of 194P, 198P, 199D, 201P, 205C, 209T/G, 212D and 218H/C; 162C, 194P and any one of 198P, 199D, 201P, 205C, 209T/G, 212D and 218H/C; 162C, 198P and any one of 199D, 201P, 205C, 209T/G, 212D and 218H/C; 162C, 199D and any one of 201P, 205C, 209T/G, 212D and 218H/C; 162C, 201P and any one of 205C, 209T/G, 212D and 218H/C; 162C, 205C and any one of 209T/G, 212D and 218H/C; 162C, 209T/G and any one of 212D and 218H/C; 162C, 212D and 218H/C; 165M, 171D and any one of 179D, 188H, 190Q, 191E, 193P, 194P, 198P, 199D, 201P, 205C, 209T/G, 212D and 218H/C; 165M, 179D and any one of 188H, 190Q, 191E, 193P, 194P, 198P, 199D, 201P, 205C, 209T/G, 212D and 218H/C; 165M, 188H and any one of 190Q, 191E, 193P, 194P, 198P, 199D, 201P, 205C, 209T/G, 212D and 218H/C; 165M, 190Q and any one of 191E, 193P, 194P, 198P, 199D, 201P, 205C, 209T/G, 212D and 218H/C; 165M, 191E and any one of 193P, 194P, 198P, 199D, 201P, 205C, 209T/G, 212D and 218H/C; 165M, 193P and any one of 194P, 198P, 199D, 201P, 205C, 209T/G, 212D and 218H/C; 165M, 194P and any one of 198P, 199D, 201P, 205C, 209T/G, 212D and 218H/C; 165M, 198P and any one of 199D, 201P, 205C, 209T/G, 212D and 218H/C; 165M, 199D and any one of 201P, 205C, 209T/G, 212D and 218H/C; 165M, 201P and any one of 205C, 209T/G, 212D and 218H/C; 165M, 205C and any one of 209T/G, 212D and 218H/C; 165M, 209T/G and any one of 212D and 218H/C; 165M, 212D and 218H/C;

171D, 179D and any one of 188H, 190Q, 191E, 193P, 194P, 198P, 199D, 201P, 205C, 209T/G, 212D and 218H/C; 171D, 188H and any one of 190Q, 191E, 193P, 194P, 198P, 199D, 201P, 205C, 209T/G, 212D and 218H/C; 171D, 190Q and any one of 191E, 193P, 194P, 198P, 199D, 201P, 205C, 209T/G, 212D and 218H/C; 171D, 191E and any one of 193P, 194P, 198P, 199D, 201P, 205C, 209T/G, 212D and 218H/C; 171D, 193P and any one of 194P, 198P, 199D, 201P, 205C, 209T/G, 212D and 218H/C; 171D, 194P and any one of 198P, 199D, 201P, 205C, 209T/G, 212D and 218H/C; 171 D, 198P and any one of 199D, 201P, 205C, 209T/G, 212 D and 218H/C; 171D, 199D and any one of 201P, 205C, 209T/G, 212D and 218H/C; 171D, 201P and any one of 205C, 209T/G, 212D and 218H/C; 171D, 205C and any one of 209T/G, 212D and 218H/C; 171D, 209T/G and any one of 212D and 218H/C; 171D, 212D and 218H/C; 179D, 188H and any one of 190Q, 191E, 193P, 194P, 198P, 199D, 201P, 205C, 209T/G, 212D and 218H/C; 179D, 190Q and any one of 191E, 193P, 194P, 198P, 199D, 201P, 205C, 209T/G, 212D and 218H/C; 179D, 191E and any one of 193P, 194P, 198P, 199D, 201P, 205C, 209T/G, 212D and 218H/C; 179D, 193P and any one of 194P, 198P, 199D, 201P, 205C, 209T/G, 212D and 218H/C; 179D, 194P and any one of 198P, 199D, 201P, 205C, 209T/G, 212D and 218H/C; 179D, 198P and any one of 199D, 201P, 205C, 209T/G, 212D and 218H/C; 179D, 199D and any one of 201P, 205C, 209T/G, 212D and 218H/C; 179D, 201P and any one of 205C, 209T/G, 212D and 218H/C; 179D, 205C and any one of 209T/G, 212D and 218H/C; 179D, 209T/G and any one of 212D and 218H/C; 179D, 212D and 218H/C; 188H, 190Q and any one of 191E, 193P, 194P, 198P, 199D, 201P, 205C, 209T/G, 212D and 218H/C; 188H, 191E and any one of 193P, 194P, 198P, 199D, 201P, 205C, 209T/G, 212D and 218H/C; 188H, 193P and any one of 194P, 198P, 199D, 201P, 205C, 209T/G, 212D and 218H/C; 188H, 194P and any one of 198P, 199D, 201P, 205C, 209T/G, 212D and 218H/C; 188H, 198P and any one of 199D, 201P, 205C, 209T/G, 212D and 218H/C; 188H, 199D and any one of 201P, 205C, 209T/G, 212D and 218H/C; 188H, 201P and any one of 205C, 209T/G, 212D and 218H/C; 188H, 205C and any one of 209T/G, 212D and 218H/C; 188H, 209T/G and any one of 212D and 218H/C; 188H, 212D and 218H/C; 190Q, 191E and any one of 193P, 194P, 198P, 199D, 201P, 205C, 209T/G, 212D and 218H/C; 190Q, 193P and any one of 194P, 198P, 199D, 201P, 205C, 209T/G, 212D and 218H/C; 190Q, 194P and any one of 198P, 199D, 201P, 205C, 209T/G, 212D and 218H/C; 190Q, 198P and any one of 199D, 201P, 205C, 209T/G, 212D and 218H/C; 190Q, 199D and any one of 201P, 205C, 209T/G, 212D and 218H/C;

190Q, 201P and any one of 205C, 209T/G, 212D and 218H/C; 190Q, 205C and any one of 209T/G, 212D and 218H/C; 190Q, 209T/G and any one of 212D and 218H/C; 190Q, 212D and 218H/C;

191E, 193P and any one of 194P, 198P, 199D, 201P, 205C, 209T/G, 212D and 218H/C; 191E, 194P and any one of 198P, 199D, 201P, 205C, 209T/G, 212D and 218H/C; 191E, 198P and any one of 199D, 201P, 205C, 209T/G, 212D and 218H/C; 191E, 199D and any one of 201P, 205C, 209T/G, 212D and 218H/C; 191E, 201P and any one of 205C, 209T/G, 212D and 218H/C; 191E, 205C and any one of 209T/G, 212D and 218H/C; 191E, 209T/G and any one of 212D and 218H/C; 191E, 212D and 218H/C; 193P, 194P and any one of 198P, 199D, 201P, 205C, 209T/G, 212D and 218H/C; 193P, 198P and any one of 199D, 201P, 205C, 209T/G, 212D and 218H/C; 193P, 199D and any one of 201P, 205C, 209T/G, 212D and 218H/C; 193P, 201P and any one of 205C, 209T/G, 212D and 218H/C; 193P, 205C and any one of 209T/G, 212D and 218H/C; 193P, 209T/G and any one of 212D and 218H/C; 193P, 212D and 218H/C;

194P, 198P and any one of 199D, 201P, 205C, 209T/G, 212D and 218H/C; 194P, 199D and any one of 201P, 205C, 209T/G, 212D and 218H/C; 194P, 201P and any one of 205C, 209T/G, 212D and 218H/C; 194P, 205C and any one of 209T/G, 212D and 218H/C; 194P, 209T/G and any one of 212D and 218H/C; 194P, 212D and 218H/C;

198P, 199D and any one of 201P, 205C, 209T/G, 212D and 218H/C; 198P, 201P and any one of 205C, 209T/G, 212D and 218H/C; 198P, 205C and any one of 209T/G, 212D and 218H/C; 198P, 209T/G and any one of 212D and 218H/C; 198P, 212D and 218H/C;

199D, 201P and any one of 205C, 209T/G, 212D and 218H/C; 199D, 205C and any one of 209T/G, 212D and 218H/C; 199D, 209T/G and any one of 212D and 218H/C; 199D, 212D and 218H/C;

201P, 205C and any one of 209T/G, 212D and 218H/C; 201P, 209T/G and any one of 212D and 218H/C; 201P, 212D and 218H/C; 205C, 209T/G and any one of 212D and 218H/C; 205C, 212D and 218H/C; 209T/G, 212D and 218H/C.

In various embodiments, the first amino acid sequence comprises any one of the following sets of substitutions and/or deletions: 191D+198P, 191P+198P, 193P+198P, 191H+193H+198P, 191H+193D+198P, 191G+195S+198P, 191E+194P+198P, del191+192P+198P, 191G+L195S+198P, and 218D+198P. These double and triple mutants have been shown to exhibit further increased stability relative to a single mutant that already has increased stability relative to the wildtype.

In various embodiments, said fragments of the variants are at least 50 amino acids in length and retain at least one of the one or more amino acid substitution(s) or deletion(s).

In various embodiments, said fragments comprise at least one GG repeat sequence, preferably two or three GG repeat sequences, as defined below. In various embodiments, said fragments retain most of the C-terminal secretion signal, i.e. the C-terminal 40-60 amino acids, optionally with substitutions and deletions as defined herein.

In various embodiments, the isolated polypeptide comprises less than 218 continuous amino acids of the amino acid sequence set forth in SEQ ID NO:1. In various embodiments, the total length of the first amino acid sequence is 218 amino acids or less.

In some embodiments, the first amino acid sequence is derived from the amino acid sequence set forth in SEQ ID NO:1 by any one or more of an N-terminal truncation, a C-terminal truncation or a deletion of one or more amino acids. The first amino acid sequence may be at least 50 amino acids in length, preferably at least 60, 70, 80, 90, 100, 110, 120, 130, 140, 150, 160, 170, 180, 190, 200, 210, 211, 212, 213, 214, 215, 216, 217 or 218 amino acids long. In various embodiments, the fragment has a C-terminal truncation, for example of amino acids in the positions corresponding to positions 214-218, 215-218, 185-218, 165-218, 135-218, or 111-218 of SEQ ID NO:1. In various embodiments the C-terminal end up to amino acid 110 (not including 110) in the numbering of SEQ ID NO:1 may be truncated. In various other embodiments, the amino acids in positions corresponding to positions 214-218 or 215-218 of SEQ ID NO:1 and additionally in the positions corresponding to positions 164-168, 165-168, 164-173, 165-173, 164-183, 165-183, 164-182 or 165-182 of SEQ ID NO:1 may be deleted. In various embodiments any continuous 4 or more amino acids in the region corresponding to positions 164-183 of SEQ ID NO:1, in particular starting from position 164 or 165 and up to position 182 or 183 may be deleted. Exemplary embodiments of such truncated variants are set forth in SEQ ID Nos. 22-28. In various embodiments, the first amino acid sequence is not C-terminally truncated. This may mean that it comprises an intact C-terminus comprising the 40-60 C-terminal amino acids of SEQ ID NO:1, these may however include the substitutions disclosed herein as well as 5 or less, for example 4, 3, 2, 1 or 0, single amino acid deletions.

In various embodiments, the isolated polypeptide comprises a second amino acid sequence N-terminal or C-terminal to the first amino acid sequence, wherein the second amino acid sequence encodes for at least one peptide or polypeptide of interest. The second amino acid sequence may be linked directly or via a linker sequence to the N- or C-terminal end of the first amino acid sequence. The linker sequence, if present, may be 1 to 30 amino acids in length. In some embodiments, the linker sequence comprises a protease recognition and cleavage site. Exemplary embodiments are described below.

In various embodiments, the second amino acid sequence is 2 to 1000, for example 2 to 500 amino acids in length, preferably 10 to 200 amino acids in length. The lower limit may also be 12 or 15 amino acids and the upper limit, independently thereof, also 180 or 150 or 100 amino acids.

In some embodiments, the isolated polypeptide further comprises at least one third amino acid sequence, optionally at least one affinity tag.

In various embodiments, the isolated polypeptide has relative to a polypeptide having the amino acid sequence of SEQ ID NO:1 as the first amino acid sequence an increased solubility or stability and, optionally, an equal or increased expression in a host cell under identical (expression) conditions. In various embodiments, where the first amino acid sequence is shorter than SEQ ID NO:1, the yields of the fused second amino acid sequence, i.e. the polypeptide/peptide of interest, may still be higher, even if the total expression level is only the same or slightly lower, since the ratio of tag to peptide of interest is better.

In another aspect, a nucleic acid, nucleic acid molecule or isolated nucleic acid molecule may encode the isolated polypeptide as described herein. In one aspect, said nucleic acid is part of a vector. One aspect thus features a (nucleic acid) vector comprising a nucleic acid molecule. The vector may be an expression vector and may comprise additional nucleic acid sequences necessary to facilitate its function in a host cell.

One further aspect relates to a host cell comprising a nucleic acid molecule or a vector. The host cell may be a prokaryotic host cell, for example an *E. coli* cell.

In a still further aspect, a method for the production of a polypeptide (isolated polypeptide) as described herein may include (1) cultivating the host cell described herein under conditions that allow the expression of the polypeptide; and (2) isolating the expressed polypeptide from the host cell.

The method may, in various embodiments, further comprise recovering the expressed peptide or protein from the host cell and/or the culture medium. In some embodiments of the methods described herein, the method further comprises secretion of the expressed recombinant peptide or protein into the culture medium by cultivating the host cell under conditions that allow secretion of the recombinant peptide or protein into the culture medium. To achieve this, the host cell may comprise further nucleic acid molecules that encode for components of a secretion system.

The method may in various embodiments also comprise recovering the expressed peptide or protein from the host cell in form of insoluble protein aggregates, namely inclusion bodies. In such embodiments, the methods may comprise a step of re-solubilizing the peptide/protein and/or reconstituting/refolding it under suitable conditions.

In various embodiments of the methods, the host cell is a prokaryotic cell, for example an *E. coli* cell. In various embodiments, the host cell may express HlyB and HlyD, for example either endogenously or by introduction of exogenous nucleic acid sequences. In various embodiments, the expression is performed in minimal culture medium; and/or the culture medium comprises 1-40 mM of an earth alkaline metal ion, such as Ca2+. In various embodiments, the recombinant peptide or protein is purified using a method selected from affinity chromatography, ion exchange chromatography, reverse phase chromatography, size exclusion chromatography, and combinations thereof; and/or the method comprises treatment of the recombinant peptide or protein with a protease suitable for cleavage of a protease cleavage site within the recombinant peptide or protein and, optionally, said treatment with a protease is followed by purification of the recombinant peptide or protein.

In still another aspect, an isolated polypeptide may be used for facilitating the production of a recombinant peptide or protein.

It is understood that all combinations of the above disclosed embodiments are also intended to fall within the scope of the claims.

DETAILED DESCRIPTION

Figure 1:
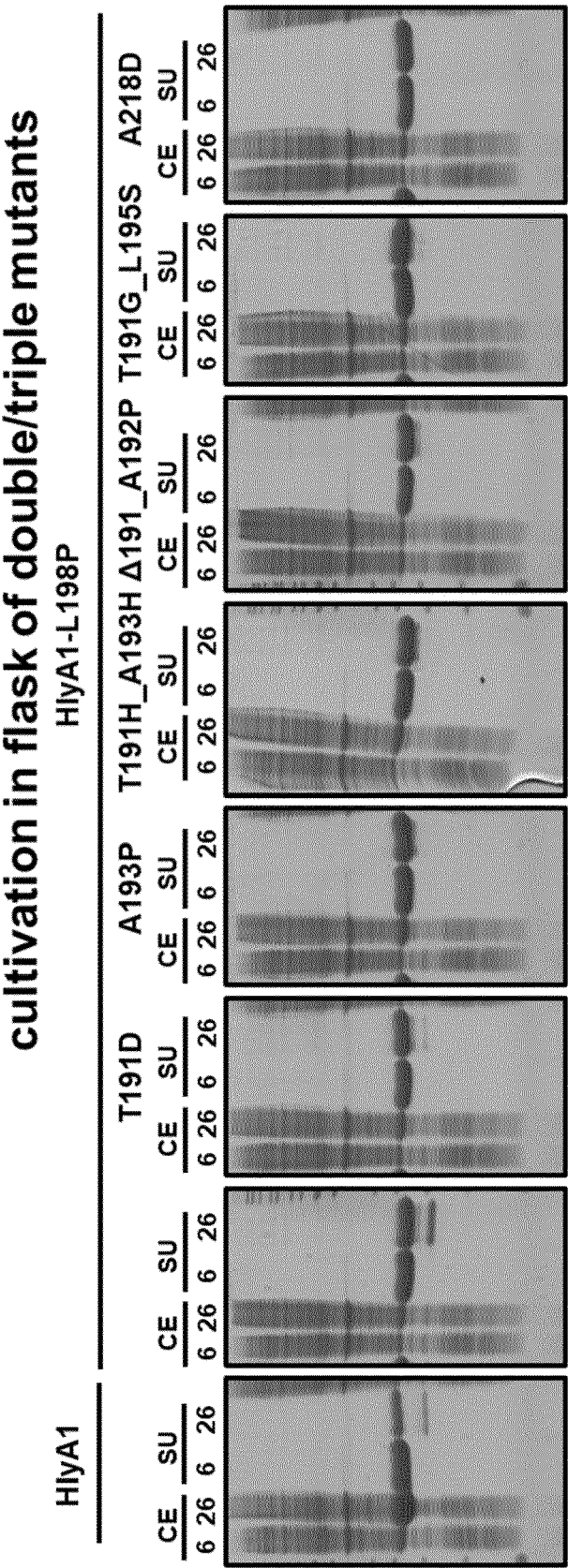
FIG. 1 shows an SDS-PAGE analysis of secreted polypeptides ("SU") comprising different substitutions (as detailed in Example 2) after "6" and "26" hours of cultivation in flasks. "CE"=cell lysate.

The terms used herein have, unless explicitly stated otherwise, the meanings as commonly understood in the art.

"At least one", as used herein, relates to one or more, in particular 1, 2, 3, 4, 5, 6, 7, 8, 9, 10 or more.

"Isolated" as used herein in relation to a molecule means that said molecule has been at least partially separated from other molecules it naturally associates with or other cellular components. "Isolated" may mean that the molecule has been purified to separate it from other molecules and components, such as other proteins and nucleic acids and cellular debris.

"Nucleic acid" as used herein includes all natural forms of nucleic acids, such as DNA and RNA. Preferably, the nucleic acid molecules are DNA.

The term "peptide" is used throughout the specification to designate a polymer of amino acid residues connected to each other by peptide bonds. A peptide may have 2-100 amino acid residues. The terms "protein" and "polypeptide" are used interchangeably throughout the specification to designate a polymer of amino acid residues connected to each other by peptide bonds. A protein or polypeptide has preferably 100 or more amino acid residues.

The term "an N-terminal fragment" relates to a peptide or protein sequence which is in comparison to a reference peptide or protein sequence C-terminally truncated, such that a contiguous amino acid polymer starting from the N-terminus of the peptide or protein remains. In some embodiments, such fragments may have a length of at least 30 amino acids, at least 50 amino acids or at least 70 amino acids.

The term "a C-terminal fragment" relates to a peptide or protein sequence which is in comparison to a reference peptide or protein sequence N-terminally truncated, such that a contiguous amino acid polymer starting from the C-terminus of the peptide or protein remains. In some embodiments, such fragments may have a length of at least 30 amino acids, at least 50 amino acids or at least 70 amino acids.

The term "fusion protein" as used herein concerns two or more peptides and proteins which are N- or C-terminally connected to each other, typically by peptide bonds, including via an amino acid/peptide linker sequence. Such fusion proteins may be encoded by two or more nucleic acid sequences which are operably fused to each other. In certain embodiments, a fusion protein refers to at least one peptide or protein of interest C-terminally or N-terminally fused to a first amino acid sequence. In various embodiments, the peptide or protein of interest is fused to the C-terminus of the first amino acid sequence, optionally via a linker sequence.

"Stability", as used herein in relation to the polypeptides, primarily relates to resistance to proteolytic degradation, which is a commonly encountered issue, in particular in conditions of high cell density and/or high protein yields.

"Solubility", as used herein in relation to the polypeptides, primarily relates to solubility in the cytoplasm and/or culture medium so that the polypeptide can be successfully secreted and purified from the cultivation medium.

"Renaturation" and "renaturation efficiency", as used herein in relation to the polypeptides, primarily relates to the possibility to isolate the polypeptide in denatured/unfolded form, for example from insoluble protein aggregates, such as inclusion bodies, and induce its proper folding to the active, three-dimensional conformation. The efficiency may be given as the mass of successfully renatured protein relative to the total mass of all expressed protein, including insoluble protein, in percent. The refolding may be effected in special refolding buffers including earth alkaline metal ions, in particular calcium ions, to induce refolding of the first amino acid sequence, which in turn facilitates renaturation of the complete fusion construct into its functional conformation.

Generally, the skilled person understands that any nucleotide sequence described herein may comprise an additional start and/or stop codon or that a start and/or stop codon included in any of the sequences described herein may be deleted, depending on the nucleic acid construct used. The skilled person will base this decision, e.g., on whether a nucleic acid sequence comprised in the nucleic acid molecule is to be translated and/or is to be translated as a fusion protein. In various embodiments, the polypeptide variants additionally comprise the amino acid M on the N-terminus of the isolated polypeptide.

The hemolysin (Hly) secretion system is a protein secretion system which mostly occurs in gram-negative bacteria. This secretion system belongs to the family of type I secretion systems which transport their substrates in an ATP driven manner in a single step from the cytosol to the extracellular space without an intermediate station in the periplasm. The Hly secretion system comprises hemolysin B (HlyB) which represents an ATP-binding cassette (ABC) transporter, the membrane fusion protein hemolysin D (HlyD), and the universal outer membrane protein TolC. The 110 kDa hemolytic toxin hemolysin A (HlyA) is a transport substrate of the Hly secretion system. On genetic level, the components necessary for hemolysin A-specific secretion are organized in an operon structure. The nucleic acid sequence encoding for hemolysin C (HlyC) also forms part of this operon but is not required for HlyA secretion through the Hly secretion system. HlyC catalyzes acylation of HlyA which renders HlyA hemolytic. HlyA is a protein which consists of 1024 amino acid residues and requires for its export via the Hly secretion system its C-terminus, comprising about 40-60 amino acids. Furthermore, HlyA is characterized in that it comprises N-terminally to the 40-60 C-terminal amino acids a domain comprising several glycine rich (GG) repeats (GGXGXDXXX, wherein X can be any amino acid). Glycine rich repeats are the characteristic of the repeats in toxin (RTX) toxin family. The glycine rich repeats bind $Ca^{2+}$ which induces their folding. Hence, in absence of Ca2+ the domain comprising the glycine rich repeats is unstructured.

Certain variants of HlyA (SEQ ID NO:1) are equally if not better suited for facilitating the expression of a peptide/protein of interest than the previously used full length HlyA or the known fragment thereof having the amino acid sequence of SEQ ID NO:1 in that they have higher solubility, better resistance against proteolytic degradation, equal or higher expression levels, higher yields and/or better renaturation efficiency.

Thus, in a first aspect, an isolated polypeptide may include a first amino acid sequence, wherein the first amino acid sequence has at least 80%, at least 85%, at least 90%, at least 95%, at least 97.5%, at least 99% or at least 99.5% sequence identity over its entire length with the amino acid sequence set forth in SEQ ID NO:1 (HlyA1) and comprises one or more amino acid substitution(s) or deletion(s) in any one of the positions corresponding to positions 161, 162, 163, 165, 171, 176, 179, 180, 181, 186, 187, 188, 190, 191, 192, 193, 194, 195, 196, 197, 198, 199, 200, 201, 205, 206, 209, 210, 212, and 218 of SEQ ID NO:1 or fragments thereof.

The isolated polypeptide does not include the amino acid sequence as set forth in SEQ ID NO:1, but comprises a variant thereof that comprises at least one substitution and/or deletion as defined above.

The first amino acid sequence has, over its entire length, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97.5%, at least 98%, at least 98.5%, at least 99% or 99.5% sequence identity with the corresponding part of the amino acid sequence set forth in SEQ ID NO:1. In various embodiments, the first amino acid sequence is of the same length as the sequence set forth in SEQ ID NO:1. In other embodiments, it is a shortened fragment thereof that may be obtainable by deletions/truncations. In various embodiments, the sequence of the first amino acid sequence with the exception of the above-indicated positions that may be substituted or deleted, i.e. the remainder of the first amino acid sequence that is not substituted or deleted, is essentially identical to the sequence set forth in SEQ ID NO:1, i.e. has sequence identities of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97.5%, at least 98%, at least 98.5%, at least 99%, at least 99.5% or 100% with the sequence of SEQ ID NO:1.

Determination of the sequence identity of nucleic acid or amino acid sequences can be done by a sequence alignment based on well-established and commonly used BLAST algorithms (See, e.g. Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, S. 3389-3402). Such an alignment is based on aligning similar nucleotide or amino acid sequences stretches with each other. Another algorithm known in the art for said purpose is the FASTA algorithm. Alignments, in particular multiple sequence comparisons, are typically done by using computer programs. Commonly used are the Clustal series (See, e.g., Chenna et al. (2003): Multiple sequence alignment with the Clustal series of programs. Nucleic Acid Research 31, 3497-3500), T-Coffee (See, e.g., Notredame et al. (2000): T-Coffee: A novel method for multiple sequence alignments. J. Mol. Biol. 302, 205-217) or programs based on these known programs or algorithms. Also possible are sequence alignments using the computer program Vector NTI® Suite 10.3 (Invitrogen Corporation, 1600 Faraday Avenue, Carlsbad, CA, USA) with the set standard parameters, with the AlignX module for sequence comparisons being based on the ClustalW. If not indicated otherwise, the sequence identity is determined using the BLAST algorithm.

Such a comparison also allows determination of the similarity of the compared sequences. Said similarity is typically expressed in percent identify, i.e. the portion of identical nucleotides/amino acids at the same or corresponding (in an alignment) sequence positions relative to the total number of the aligned nucleotides/amino acids. For example, if in an alignment 90 amino acids of a 100 aa long query sequence are identical to the amino acids in corresponding positions of a template sequence, the sequence identity is 90%. The broader term "homology" additionally considers conserved amino acid substitutions, i.e. amino acids that are similar in regard to their chemical properties, since those typically have similar chemical properties in a protein. Accordingly, such homology can be expressed in percent homology. If not indicated otherwise, sequence identity and sequence homology relate to the entire length of the aligned sequence.

The feature that an amino acid position corresponds to a numerically defined position in SEQ ID NO:1 means that the respective position correlates to the numerically defined position in SEQ ID NO:1 in an alignment obtained as described above.

In various embodiments, the first amino acid sequence comprised in the isolated polypeptide is a variant of HlyA1 with the amino acid set forth in SEQ ID NO:1 and comprises, relative to the amino acid sequence of SEQ ID NO:1, one or more amino acid substitution(s) or deletion(s) in any one of the positions corresponding to positions 161, 162, 163, 165, 171, 176, 179, 180, 181, 186, 187, 188, 190, 191, 192, 193, 194, 195, 196, 197, 198, 199, 200, 201, 205, 206, 209, 210, 212, and 218, preferably one or more amino acid substitution(s) or deletion(s) in any one of the positions corresponding to positions 162, 165, 171, 179, 188, 190, 191, 193, 194, 198, 199, 201, 205, 209, 212, and 218 of SEQ ID NO:1.

In the amino acid sequence as set forth in SEQ ID NO:1, the above-identified positions are occupied by the following amino acid residues: Y161, G162, S163, G165, I171, K176, S179, A180, A181, V186, K187, E188, R190, T191, A192, A193, S194, L195, L196, Q197, L198, S199, G200, N201, F205, S206, R209, N210, I212, and A218. "Amino acid substitution", as used herein, relates to modification of the sequence such that the amino acid residue occurring at the corresponding position in SEQ ID NO:1 is replaced by another amino acid residue. The amino acid residue for substitution is typically selected from the 20 proteinogenic amino acids G, A, V, L, 1, F, C, M, P, R, K, H, N, Q, D, E, S, T, W, and Y. Accordingly, if a position in SEQ ID NO:1 is occupied by any one of these 20 amino acid residues, its substitution means that it is replaced by any one of the other 19 amino acids listed above. A "deletion" at one or more positions means that the residues adjacent to the deletion site are directly connected by a peptide bond. In various embodiments, a substitution by amino acid residues P, E, D, and C, in particular P, C and E or P and E may be particularly advantageous.

While it has been found that in principle all of the positions defined herein may be mutated such that the naturally occurring amino acid residue is replaced by any other amino acid residue, it can be preferable, in various embodiments, that the following substitutions are excluded: 163N, 176L, 193M, 193W, and 200S. Also excluded may be 215N and/or 203R. It has been found that these may yield undesired decreases in either solubility or proteolytic stability. In various embodiments, all other substitutions theoretically possible are however encompassed herein. This means that in position 163, S may be replaced by any amino acid with the exception of N, in position 176 K may be replaced by any amino acid with the exception of L, etc. All other indicated positions can be substituted by the full spectrum of the other 19 amino acids.

It has been found that the following substitutions provide for particularly good results with respect to the increase in solubility of the respective amino acid sequences and polypeptides comprising them: 161T, 162E, 162C, 163D, 165M, 171D, 176C, 179D, 179C, 180D, 181C, 186D, 187C, 187P, 188H, 190Q, 190A, 191D, 191E, 191G, 191H, 191P, 192P, 193D, 193E, 193C, 193P, 193L, 193H, 194T, 194V, 194I, 194P, 195S, 196G, 197G, 198E, 198P, 199D, 199P, 200S, 201E, 201P, 201A, 205S, 205C, 205P, 206E, 206C, 206P, 206L, 209T, 209G, 210P, 212D, 218D, 218H and 218C. While the substitution 200S has been found to be advantageous with respect to solubility, it was also found to lower proteolytic stability.

Consequently, in various embodiments, the variant comprises any one or more of the amino acid substitution(s) listed above with the exception of 200S, i.e. any one or more of: 161T, 162E, 162C, 163D, 165M, 171D, 176C, 179D, 179C, 180D, 181C, 186D, 187C, 187P, 188H, 190Q, 190A, 191D, 191E, 191G, 191H, 191P, 193D, 193E, 193C, 193P, 193L, 193H, 194T, 194V, 194I, 194P, 195S, 196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 161T, 162E, 162C, 163D, 165M, 171D, 176C, 179D, 179C, 180D, 181C, 186D, 187C, 187P, 188H, 190Q, 190A, 191E, 191D, 191H, 191P, 193E, 193C, 193P, 193L, 193H, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 161T, 162E, 162C, 163D, 165M, 171D, 176C, 179D, 179C, 180D, 181C, 186D, 187C, 187P, 188H, 190Q, 190A, 191E, 191D, 193E, 193C, 193P, 193L, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H and 218C.

In various embodiments, the variant comprises any one or more of the amino acid substitution(s): 162C, 165M, 171D, 179D, 188H, 190Q, 191D, 191E, 193E, 193P, 194, 194P, 198E, 198P, 199D, 201P, 205C, 205S, 209T, 209G, 212D, 218D, 218H and 218C. These substitutions have been found to be not only particularly advantageous with respect to increased solubility but also with respect to stability towards proteolytic degradation.

While in principle, the amino acid residues in any of the indicated positions may be deleted, it can be preferred, in various embodiments, that the variant comprises not more than 5 deletions in the indicated positions, preferably 4 or less, more preferably 3 or less, most preferably 2 or only 1 deletion. These deletions are preferably limited to the following positions using the numbering of SEQ ID NO:1: ☐187, ☐190, ☐191, ☐192, and ☐209. Deletions are referred to herein either by using the symbol ☐ followed by the position at which the amino acid residue is deleted or by using the term "del" in front of the position number, such as "del187". This means that the residue corresponding to the amino acid at position 187 in SEQ ID NO:1 is deleted such that the amino acids at positions 186 and 188 are directly linked by a peptide bond. Deletions of stretches of amino acids are identified by, for example, "del111-218" or "☐111-218", i.e. residues at positions 111-218 are deleted. In various embodiments, the comprised amino acid substitutions and/or deletions are exclusively substitutions, i.e. no deletions are comprised in the respective variants.

In various embodiments, the variant comprises any one or more of the substitutions defined above and one or more of the deletions defined above. This means that the substitutions and deletions described herein may be combined in the first amino acid sequence. All such combinations arising from the specified substitutions/deletions are contemplated herein.

Any positional numbering used herein refers, if not explicitly indicated otherwise, to the positional numbering of SEQ ID NO:1. As described above, the corresponding positions in a given amino acid sequence may be identified using alignments.

In various embodiments, the variant comprises any two or more, three or more, four or more, five or more, six or more, seven or more, eight or more, nine or more or ten or more of the amino acid substitution(s) and/or deletion(s) identified herein. In various embodiments, the variant comprises any two or more, three or more, four or more, five or more, six or more, seven or more, eight or more, nine or more or ten or more of the amino acid substitution(s) identified herein. These any two or more, three or more, four or more, five or more, six or more, seven or more, eight or more, nine or more or ten or more of the amino acid substitution(s) may be selected from the group consisting of: 161T, 162E, 162C, 163D, 165M, 171D, 176C, 179D, 179C, 180D, 181C, 186D, 187C, 187P, 188H, 190Q, 190A, 191E, 191D, 191H, 191P, 193E, 193C, 193P, 193L, 193H, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H, and 218C.

In various exemplary embodiments, the variant comprises at least 2, at least 3, at least 4, at least 5, at least 6, at least 7, at least 8, at least 9, at least 10, at least 11, at least 12, at least 13, at least 14 or all 15 of the amino acid substitution (s): 162C, 165M, 171D, 179D, 188H, 190Q, 191D, 191E, 193E, 193P, 194, 194P, 198E, 198P, 199D, 201P, 205C, 205S, 209T, 209G, 212D, 218D, 218H and 218C.

In various embodiments, it can be preferred that the variant comprises at least two or at least three of the indicated substitutions.

In various embodiments, the variant comprises amino acid substitutions/deletions, preferably substitutions, in the following positions (using the numbering of SEQ ID NO:1): 162 and 165; 162 and 171; 162 and 179; 162 and 188; 162 and 190; 162 and 191; 162 and 193; 162 and 194; 162 and 198; 162 and 199; 162 and 201; 162 and 205; 162 and 209; 162 and 212; 162 and 218; 165 and 171; 165 and 179; 165 and 188; 165 and 190; 165 and 191; 165 and 193; 165 and 194; 165 and 198; 165 and 199; 165 and 201; 165 and 205; 165 and 209; 165 and 212; 165 and 218; 171 and 179; 171 and 188; 171 and 190; 171 and 191; 171 and 193; 171 and 194; 171 and 198; 171 and 199; 171 and 201; 171 and 205; 171 and 209; 171 and 212; 171 and 218; 179 and 188; 179 and 190; 179 and 191; 179 and 193; 179 and 194; 179 and 198; 179 and 199; 179 and 201; 179 and 205; 179 and 209; 179 and 212; 179 and 218; 188 and 190; 188 and 191; 188 and 193; 188 and 194; 188 and 198; 188 and 199; 188 and 201; 188 and 205; 188 and 209; 188 and 212; 188 and 218; 190 and 191; 190 and 193; 190 and 194; 190 and 198; 190 and 199; 190 and 201; 190 and 205; 190 and 209; 190 and 212; 190 and 218; 191 and 193; 191 and 194; 191 and 198; 191 and 199; 191 and 201; 191 and 205; 191 and 209; 191 and 212; 191 and 218; 193 and 194; 193 and 198; 193 and 199; 193 and 201; 193 and 205; 193 and 209; 193 and 212; 193 and 218; 194 and 198; 194 and 199; 194 and 201; 194 and 205; 194 and 209; 194 and 212; 194 and 218; 198 and 199; 198 and 201; 198 and 205; 198 and 209; 198 and 212; 198 and 218; 199 and 201; 199 and 205; 199 and 209; 199 and 212; 199 and 218; 201 and 205; 201 and 209; 201 and 212; 201 and 218; 205 and 209; 205 and 212; 205 and 218; 209 and 212; 209 and 218; 212 and 218;

162, 165 and any one of 171, 179, 188, 190, 191, 193, 194, 198, 199, 201, 205, 209, 212 and 218; 162, 171 and any one of 179, 188, 190, 191, 193, 194, 198, 199, 201, 205, 209, 212 and 218; 162, 179 and any one of 188, 190, 191, 193, 194, 198, 199, 201, 205, 209, 212 and 218; 162, 188 and any one of 190, 191, 193, 194, 198, 199, 201, 205, 209, 212 and 218; 162, 190 and any one of 191, 193, 194, 198, 199, 201, 205, 209, 212 and 218; 162, 191 and any one of 193, 194, 198, 199, 201, 205, 209, 212 and 218; 162, 193 and any one of 194, 198, 199, 201, 205, 209, 212 and 218; 162, 194 and any one of 198, 199, 201, 205, 209, 212 and 218; 162, 198 and any one of 199, 201, 205, 209, 212 and 218; 162, 199 and any one of 201, 205, 209, 212 and 218; 162, 201 and any one of 205, 209, 212 and 218; 162, 205 and any one of 209, 212 and 218; 162, 209 and any one of 212 and 218; 162, 212 and 218;

165, 171 and any one of 179, 188, 190, 191, 193, 194, 198, 199, 201, 205, 209, 212 and 218; 165, 179 and any one of 188, 190, 191, 193, 194, 198, 199, 201, 205, 209, 212 and 218; 165, 188 and any one of 190, 191, 193, 194, 198, 199, 201, 205, 209, 212 and 218; 165, 190 and any one of 191, 193, 194, 198, 199, 201, 205, 209, 212 and 218; 165, 191 and any one of 193, 194, 198, 199, 201, 205, 209, 212 and 218; 165, 193 and any one of 194, 198, 199, 201, 205, 209, 212 and 218; 165, 194 and any one of 198, 199, 201, 205, 209, 212 and 218; 165, 198 and any one of 199, 201, 205, 209, 212 and 218; 165, 199 and any one of 201, 205, 209, 212 and 218; 165, 201 and any one of 205, 209, 212 and 218; 165, 205 and any one of 209, 212 and 218; 165, 209 and any one of 212 and 218; 165, 212 and 218;

171, 179 and any one of 188, 190, 191, 193, 194, 198, 199, 201, 205, 209, 212 and 218; 171, 188 and any one of 190, 191, 193, 194, 198, 199, 201, 205, 209, 212 and 218; 171, 190 and any one of 191, 193, 194, 198, 199, 201, 205, 209, 212 and 218; 171, 191 and any one of 193, 194, 198, 199, 201, 205, 209, 212 and 218; 171, 193 and any one of 194, 198, 199, 201, 205, 209, 212 and 218; 171, 194 and any one of 198, 199, 201, 205, 209, 212 and 218; 171, 198 and any one of 199, 201, 205, 209, 212 and 218; 171, 199 and any one of 201, 205, 209, 212 and 218; 171, 201 and any one of 205, 209, 212 and 218; 171, 205 and any one of 209, 212 and 218; 171, 209 and any one of 212 and 218; 171, 212 and 218; 179, 188 and any one of 190, 191, 193, 194, 198, 199, 201, 205, 209, 212 and 218; 179, 190 and any one of 191, 193, 194, 198, 199, 201, 205, 209, 212 and 218; 179, 191 and any one of 193, 194, 198, 199, 201, 205, 209, 212 and 218; 179, 193 and any one of 194, 198, 199, 201, 205, 209, 212 and 218; 179, 194 and any one of 198, 199, 201, 205, 209, 212 and 218; 179, 198 and any one of 199, 201, 205, 209, 212 and 218; 179, 199 and any one of 201, 205, 209, 212 and 218; 179, 201 and any one of 205, 209, 212 and 218; 179, 205 and any one of 209, 212 and 218; 179, 209 and any one of 212 and 218; 179, 212 and 218;

188, 190 and any one of 191, 193, 194, 198, 199, 201, 205, 209, 212 and 218; 188, 191 and any one of 193, 194, 198, 199, 201, 205, 209, 212 and 218; 188, 193 and any one of 194, 198, 199, 201, 205, 209, 212 and 218; 188, 194 and any one of 198, 199, 201, 205, 209, 212 and 218; 188, 198 and any one of 199, 201, 205, 209, 212 and 218; 188, 199 and any one of 201, 205, 209, 212 and 218; 188, 201 and any one of 205, 209, 212 and 218; 188, 205 and any one of 209, 212 and 218; 188, 209 and any one of 212 and 218; 188, 212 and 218;

190, 191 and any one of 193, 194, 198, 199, 201, 205, 209, 212 and 218; 190, 193 and any one of 194, 198, 199, 201, 205, 209, 212 and 218; 190, 194 and any one of 198, 199, 201, 205, 209, 212 and 218; 190, 198 and any one of 199, 201, 205, 209, 212 and 218; 190, 199 and any one of 201, 205, 209, 212 and 218; 190, 201 and any one of 205, 209, 212 and 218; 190, 205 and any one of 209, 212 and 218; 190, 209 and any one of 212 and 218; 190, 212 and 218;

191, 193 and any one of 194, 198, 199, 201, 205, 209, 212 and 218; 191, 194 and any one of 198, 199, 201, 205, 209, 212 and 218; 191, 198 and any one of 199, 201, 205, 209, 212 and 218; 191, 199 and any one of 201, 205, 209, 212 and 218; 191, 201 and any one of 205, 209, 212 and 218; 191, 205 and any one of 209, 212 and 218; 191, 209 and any one of 212 and 218; 191, 212 and 218;

193, 194 and any one of 198, 199, 201, 205, 209, 212 and 218; 193, 198 and any one of 199, 201, 205, 209, 212 and 218; 193, 199 and any one of 201, 205, 209, 212 and 218; 193, 201 and any one of 205, 209, 212 and 218; 193, 205 and any one of 209, 212 and 218; 193, 209 and any one of 212 and 218; 193, 212 and 218;

194, 198 and any one of 199, 201, 205, 209, 212 and 218; 194, 199 and any one of 201, 205, 209, 212 and 218; 194, 201 and any one of 205, 209, 212 and 218; 194, 205 and any one of 209, 212 and 218; 194, 209 and any one of 212 and 218; 194, 212 and 218;

198, 199 and any one of 201, 205, 209, 212 and 218; 198, 201 and any one of 205, 209, 212 and 218; 198, 205 and any one of 209, 212 and 218; 198, 209 and any one of 212 and 218; 198, 212 and 218;

199, 201 and any one of 205, 209, 212 and 218; 199, 205 and any one of 209, 212 and 218; 199, 209 and any one of 212 and 218; 199, 212 and 218; 201, 205 and any one of 209, 212 and 218; 201, 209 and any one of 212 and 218; 201, 212 and 218; 205, 209 and any one of 212 and 218; 205, 212 and 218; 209, 212 and 218;

In any of the above embodiments, the substitutions may be selected from 162C, 165M, 171D, 179D, 188H, 190Q, 191D, 191E, 193E, 193P, 194, 194P, 198E, 198P, 199D, 201P, 205C, 205S, 209T, 209G, 212D, 218H and 218C. The deletions may be selected from del187, del190, and del209. In various other embodiments, the above variants do not comprise any of the indicated deletions.

In other embodiments, fragments of the amino acid sequence set forth in SEQ ID NO:1 may include deletions of 4 or more amino acids. Such fragments will be described in more detail below. It may, in various embodiments, be preferred that the C-terminus remains intact so that it can mediate secretion of the fusion proteins.

In various embodiments, any of the afore-mentioned variants with specified substitution/deletion patterns may additionally comprise one or more amino acid substitutions/deletions in the positions corresponding to positions 161, 163, 176, 180, 181, 186, 187, 196, 197, 206, and 210 of SEQ ID NO:1.

In various embodiments, the variant comprises the following sets of amino acid substitution(s): 162C and 165M; 162C and 171D; 162C and 179D; 162CC and 188H; 162C and 190Q; 162C and 191D/E/P/H; 162C and 193E/P/H; 162C and 194P/I; 162C and 198E/P; 162C and 199D; 162C and 201P; 162C and 205C/S; 162C and 209T/G; 162C and 212D; 162C and 218D/H/C; 165M and 171D; 165M and 179D; 165M and 188H; 165M and 190Q; 165M and 191D/E/P/H; 165M and 193E/P/H; 165M and 194P/I; 165M and 198E/P; 165M and 199D; 165M and 201P; 165M and 205C/S; 165M and 209T/G; 165M and 212D; 165M and 218D/H/C; 171D and 179D; 171D and 188H; 171D and 190Q; 171D and 191D/E/P/H; 171D and 193E/P/H; 171D and 194P/I; 171D and 198E/P; 171D and 199D; 171D and 201P; 171D and 205C/S; 171D and 209T/G; 171D and 212D; 171D and 218D/H/C; 179D and 188H; 179D and 190Q; 179D and 191D/E/P/H; 179D and 193E/P/H; 179D and 194P/I; 179D and 198E/P; 179D and 199D; 179D and 201P; 179D and 205C/S; 179D and 209T/G; 179D and 212D; 179D and 218D/H/C; 188H and 190Q; 188H and 191D/E/P/H; 188H and 193E/P/H; 188H and 194P/I; 188H and 198E/P; 188H and 199D; 188H and 201P; 188H and 205C/S; 188H and 209T/G; 188H and 212D; 188H and 218D/H/C; 190Q and 191D/E/P/H; 190Q and 193E/P/H; 190Q and 194P/I; 190Q and 198E/P; 190Q and 199D; 190Q and 201P; 190Q and 205C/S; 190Q and 209T/G; 190Q and 212D; 190Q and 218D/H/C; 191D/E/P/H and 193E/P/H; 191D/E/P/H and 194P/I; 191D/E/P/H and 198E/P; 191D/E/P/H and 199D; 191D/E/P/H and 201P; 191D/E/P/H and 205C/S; 191D/E/P/H and 209T/G; 191D/E/P/H and 212D; 191D/E/P/H and 218D/H/C; 193E/P/H and 194P/I; 193E/P/H and 198E/P; 193E/P/H and 199D; 193E/P/H and 201P; 193E/P/H and 205C/S; 193E/P/H and 209T/G; 193E/P/H and 212D; 193E/P/H and 218D/H/C; 194P/I and 198E/P; 194P/I and 199D; 194P/I and 201P; 194P/I and 205C/S; 194P/I and 209T/G; 194P/I and 212D; 194P/I and 218D/H/C; 198E/P and 199D; 198E/P and 201P; 198E/P and 205C/S; 198E/P and 209T/G; 198E/P and 212D; 198E/P and 218D/H/C; 199D and 201P; 199D and 205C/S; 199D and 209T/G; 199D and 212D; 199D and 218D/H/C; 201P and 205C/S; 201P and 209T/G; 201P and 212D; 201P and 218D/H/C; 205C/S and 209T/G; 205C/S and 212D; 205C/S and 218D/H/C; 209T/G and 212D; 209T/G and 218D/H/C; 212D and 218D/H/C;

162C, 165M and any one of 171D, 179D, 188H, 190Q, 191D/E/P/H, 193E/P/H, 194P/I, 198E/P, 199D, 201P, 205C/S, 209T/G, 212D and 218D/H/C; 162C, 171D and any one of 179D, 188H, 190Q, 191D/E/P/H, 193E/P/H, 194P/I, 198E/P, 199D, 201P, 205C/S, 209T/G, 212D and 218D/H/C; 162C, 179D and any one of 188H, 190Q, 191D/E/P/H, 193E/P/H, 194P/I, 198E/P, 199D, 201P, 205C/S, 209T/G, 212D and 218D/H/C; 162C, 188H and any one of 190Q, 191D/E/P/H, 193E/P/H, 194P/I, 198E/P, 199D, 201P, 205C/S, 209T/G, 212D and 218D/H/C; 162C, 190Q and any one of 191D/E/P/H, 193E/P/H, 194P/I, 198E/P, 199D, 201P, 205C/S, 209T/G, 212D and 218D/H/C; 162C, 191D/E/P/H and any one of 193E/P/H, 194P/I, 198E/P, 199D, 201P, 205C/S, 209T/G, 212D and 218D/H/C; 162C, 193E/P/H and any one of 194P/I, 198E/P, 199D, 201P, 205C/S, 209T/G, 212D and 218D/H/C; 162C, 194P/I and any one of 198E/P, 199D, 201P, 205C/S, 209T/G, 212D and 218D/H/C; 162C, 198E/P and any one of 199D, 201P, 205C/S, 209T/G, 212D and 218D/H/C; 162C, 199D and any one of 201P, 205C/S, 209T/G, 212D and 218D/H/C; 162C, 201P and any one of 205C/S, 209T/G, 212D and 218D/H/C; 162C, 205C/S and any one of 209T/G, 212D and 218D/H/C; 162C, 209T/G and any one of 212D and 218D/H/C; 162C, 212D and 218D/H/C;
165M, 171D and any one of 179D, 188H, 190Q, 191D/E/P/H, 193E/P/H, 194P/I, 198E/P, 199D, 201P, 205C/S, 209T/G, 212D and 218D/H/C; 165M, 179D and any one of 188H, 190Q, 191D/E/P/H, 193E/P/H, 194P/I, 198E/P, 199D, 201P, 205C/S, 209T/G, 212D and 218D/H/C; 165M, 188H and any one of 190Q, 191D/E/P/H, 193E/P/H, 194P/I, 198E/P, 199D, 201P, 205C/S, 209T/G, 212D and 218D/H/C; 165M, 190Q and any one of 191 D/E/P/H, 193E/P/H, 194P/I, 198E/P, 199D, 201P, 205C/S, 209T/G, 212D and 218D/H/C; 165M, 191D/E/P/H and any one of 193E/P/H, 194P/I, 198E/P, 199D, 201P, 205C/S, 209T/G, 212D and 218D/H/C; 165M, 193E/P/H and any one of 194P/I, 198E/P, 199D, 201P, 205C/S, 209T/G, 212D and 218D/H/C; 165M, 194P/I and any one of 198E/P, 199D, 201P, 205C/S, 209T/G, 212D and 218D/H/C; 165M, 198E/P and any one of 199D, 201P, 205C/S, 209T/G, 212D and 218D/H/C; 165M, 199D and any one of 201P, 205C/S, 209T/G, 212D and 218D/H/C; 165M, 201P and any one of 205C/S, 209T/G, 212D and 218D/H/C; 165M, 205C/S and any one of 209T/G, 212D and 218D/H/C; 165M, 209T/G and any one of 212D and 218D/H/C; 165M, 212D and 218D/H/C;

171D, 179D and any one of 188H, 190Q, 191D/E/P/H, 193E/P/H, 194P/I, 198E/P, 199D, 201P, 205C/S, 209T/G, 212D and 218D/H/C; 171D, 188H and any one of 190Q, 191D/E/P/H, 193E/P/H, 194P/I, 198E/P, 199D, 201P, 205C/S, 209T/G, 212D and 218D/H/C; 171D, 190Q and any one of 191D/E/P/H, 193E/P/H, 194P/I, 198E/P, 199D, 201P, 205C/S, 209T/G, 212D and 218D/H/C; 171D, 191D/E/P/H and any one of 193E/P/H, 194P/I, 198E/P, 199D, 201P, 205C/S, 209T/G, 212D and 218D/H/C; 171D, 193E/P/H and any one of 194P/I, 198E/P, 199D, 201P, 205C/S, 209T/G, 212D and 218D/H/C; 171D, 194P/I and any one of 198E/P, 199D, 201P, 205C/S, 209T/G, 212D and 218D/H/C; 171D, 198E/P and any one of 199D, 201P, 205C/S, 209T/G, 212D and 218D/H/C; 171D, 199D and any one of 201P, 205C/S, 209T/G, 212D and 218D/H/C; 171D, 201P and any one of 205C/S, 209T/G, 212D and 218D/H/C; 171D, 205C/S and any one of 209T/G, 212D and 218D/H/C; 171D, 209T/G and any one of 212D and 218D/H/C; 171D, 212D and 218D/H/C;

179D, 188H and any one of 190Q, 191D/E/P/H, 193E/P/H, 194P/I, 198E/P, 199D, 201P, 205C/S, 209T/G, 212D and 218D/H/C; 179D, 190Q and any one of 191D/E/P/H, 193E/P/H, 194P/I, 198E/P, 199D, 201P, 205C/S, 209T/G, 212D and 218D/H/C; 179D, 191D/E/P/H and any one of 193E/P/H, 194P/I, 198E/P, 199D, 201P, 205C/S, 209T/G, 212D and 218D/H/C; 179D, 193E/P/H and any one of 194P/I, 198E/P, 199D, 201P, 205C/S, 209T/G, 212D and 218D/H/C; 179D, 194P/I and any one of 198E/P, 199D, 201P, 205C/S, 209T/G, 212D and 218D/H/C; 179D, 198E/P and any one of 199D, 201P, 205C/S, 209T/G, 212D and 218D/H/C; 179D, 199D and any one of 201P, 205C/S, 209T/G, 212D and 218D/H/C; 179D, 201P and any one of 205C/S, 209T/G, 212D and 218D/H/C; 179D, 205C/S and any one of 209T/G, 212D and 218D/H/C; 179D, 209T/G and any one of 212D and 218D/H/C; 179D, 212D and 218D/H/C;

188H, 190Q and any one of 191D/E/P/H, 193E/P/H, 194P/I, 198E/P, 199D, 201P, 205C/S, 209T/G, 212D and 218D/H/C; 188H, 191D/E/P/H and any one of 193E/P/H, 194P/I, 198E/P, 199D, 201P, 205C/S, 209T/G, 212D and 218D/H/C; 188H, 193E/P/H and any one of 194P/I, 198E/P, 199D, 201P, 205C/S, 209T/G, 212D and 218D/H/C; 188H, 194P/I and any one of 198E/P, 199D, 201P, 205C/S, 209T/G, 212D and 218D/H/C; 188H, 198E/P and any one of 199D, 201P, 205C/S, 209T/G, 212D and 218D/H/C; 188H, 199D and any one of 201P, 205C/S, 209T/G, 212D and 218D/H/C; 188H, 201P and any one of 205C/S, 209T/G, 212D and 218D/H/C; 188H, 205C/S and any one of 209T/G, 212D and 218D/H/C; 188H, 209T/G and any one of 212D and 218D/H/C; 188H, 212D and 218D/H/C;

190Q, 191D/E/P/H and any one of 193E/P/H, 194P/I, 198E/P, 199D, 201P, 205C/S, 209T/G, 212D and 218D/H/C; 190Q, 193E/P/H and any one of 194P/I, 198E/P, 199D, 201P, 205C/S, 209T/G, 212D and 218D/H/C; 190Q, 194P/I and any one of 198E/P, 199D, 201P, 205C/S, 209T/G, 212D and 218D/H/C; 190Q, 198E/P and any one of 199D, 201P, 205C/S, 209T/G, 212D and 218D/H/C; 190Q, 199D and any one of 201P, 205C/S, 209T/G, 212D and 218D/H/C; 190Q, 201P and any one of 205C/S, 209T/G, 212D and 218D/H/C; 190Q, 205C/S and any one of 209T/G, 212D and 218D/H/C; 190Q, 209T/G and any one of 212D and 218D/H/C; 190Q, 212D and 218D/H/C;

191D/E/P/H, 193E/P/H and any one of 194P/I, 198E/P, 199D, 201P, 205C/S, 209T/G, 212D and 218D/H/C; 191D/E/P/H, 194P/I and any one of 198E/P, 199D, 201P, 205C/S, 209T/G, 212D and 218D/H/C; 191D/E/P/H, 198E/P and any one of 199D, 201P, 205C/S, 209T/G, 212D and 218D/H/C; 191D/E/P/H, 199D and any one of 201P, 205C/S, 209T/G, 212D and 218D/H/C; 191D/E/P/H, 201P and any one of 205C/S, 209T/G, 212D and 218D/H/C; 191D/E/P/H, 205C/S and any one of 209T/G, 212D and 218D/H/C; 191D/E/P/H, 209T/G and any one of 212D and 218D/H/C; 191D/E/P/H, 212D and 218D/H/C;

193E/P/H, 194P/I and any one of 198E/P, 199D, 201P, 205C/S, 209T/G, 212D and 218D/H/C; 193E/P/H, 198E/P and any one of 199D, 201P, 205C/S, 209T/G, 212D and 218D/H/C; 193E/P/H, 199D and any one of 201P, 205C/S, 209T/G, 212D and 218D/H/C; 193E/P/H, 201P and any one of 205C/S, 209T/G, 212D and 218D/H/C; 193E/P/H, 205C/S and any one of 209T/G, 212D and 218D/H/C; 193E/P/H, 209T/G and any one of 212D and 218D/H/C; 193E/P/H, 212D and 218D/H/C;

194P/I, 198E/P and any one of 199D, 201P, 205C/S, 209T/G, 212D and 218D/H/C; 194P/I, 199D and any one of 201P, 205C/S, 209T/G, 212D and 218D/H/C; 194P/I, 201P and any one of 205C/S, 209T/G, 212D and 218D/H/C; 194P/I, 205C/S and any one of 209T/G, 212D and 218D/H/C; 194P/I, 209T/G and any one of 212D and 218D/H/C; 194P/I, 212D and 218D/H/C;

198E/P, 199D and any one of 201P, 205C/S, 209T/G, 212D and 218D/H/C; 198E/P, 201P and any one of 205C/S, 209T/G, 212D and 218D/H/C; 198E/P, 205C/S and any one of 209T/G, 212D and 218D/H/C; 198E/P, 209T/G and any one of 212D and 218D/H/C; 198E/P, 212D and 218D/H/C; 199D, 201P and any one of 205C/S, 209T/G, 212D and 218D/H/C; 199D, 205C/S and any one of 209T/G, 212D and 218D/H/C; 199D, 209T/G and any one of 212D and 218D/H/C; 199D, 212D and 218D/H/C;

201P, 205C/S and any one of 209T/G, 212D and 218D/H/C; 201P, 209T/G and any one of 212D and 218D/H/C; 201P, 212D and 218D/H/C; 205C/S, 209T/G and any one of 212D and 218D/H/C; 205C/S, 212D and 218D/H/C; 209T/G, 212D and 218D/H/C.

In various embodiments, the variant comprises the following sets of amino acid substitution(s):

191D and 193E/P/H; 191E and 193E/P/H; 191P and 193E/P/H; 191H and 193E/P/H; 191D and 194P/I; 191E and 194P/I; 191P and 194P/I; 191H and 194P/I; 191D and 198E/P; 191E and 198E/P; 191P and 198E/P; 191H and 198E/P; 191D and 205C/S; 191E and 205C/S; 191P and 205C/S; 191H and 205C/S; 191D and 209T/G; 191E and 209T/G; 191P and 209T/G; 191H and 209T/G; 191D and 218D/H/C; 191E and 218D/H/C; 191P and 218D/H/C; 191H and 218D/H/C; 193E and 194P/I; 193P and 194P/I; 193H and 194P/I; 193E and 198E/P; 193P and 198E/P; 193H and 198E/P; 193E and 205C/S; 193P and 205C/S; 193H and 205C/S; 193E and 209T/G; 193P and 209T/G; 193H and 209T/G; 193E and 218D/H/C; 193P and 218D/H/C; 193H and 218D/H/C; 194P and 198E/P; 194I and 198E/P; 194P and 205C/S; 194I and 205C/S; 194P and 209T/G; 194I and 209T/G; 194P and 218D/H/C; 194I and 218D/H/C; 198P and 205C/S; 198E and 205C/S; 198P and 209T/G; 198E and 209T/G; 198P and 218D/H/C; 198E and 218D/H/C; 205C and 209T/G; 205S and 209T/G; 205C and 218D/H/C; 205S and 218D/H/C; 209T and 218D/H/C; 209G and 218D/H/C;

162C, 191D and any one of 193E/P/H, 194P/I, 198E/P, 199D, 201P, 205C/S, 209T/G, 212D and 218D/H/C; 162C, 191E and any one of 193E/P/H, 194P/I, 198E/P, 199D, 201P, 205C/S, 209T/G, 212D and 218D/H/C; 162C, 191P and any one of 193E/P/H, 194P/I, 198E/P, 199D, 201P, 205C/S, 209T/G, 212D and 218D/H/C; 162C, 191H and any one of 193E/P/H, 194P/I, 198E/P, 199D, 201P, 205C/S, 209T/G, 212D and 218D/H/C; 162C, 193E and any one of 194P/I, 198E/P, 199D, 201P, 205C/S, 209T/G, 212D and 218D/H/C; 162C, 193P and any one of 194P/I, 198E/P, 199D, 201P, 205C/S, 209T/G, 212D and 218D/H/C; 162C, 193H and any one of 194P/I, 198E/P, 199D, 201P, 205C/S, 209T/G, 212D and 218D/H/C; 162C, 194P and any one of 198E/P, 199D, 201P, 205C/S, 209T/G, 212D and 218D/H/C; 162C, 194I and any one of 198E/P, 199D, 201P, 205C/S, 209T/G, 212D and 218D/H/C; 162C, 198E and any one of 199D, 201P, 205C/S, 209T/G, 212D and 218D/H/C; 162C, 198P and any one of 199D, 201P, 205C/S, 209T/G, 212D and 218D/H/C; 162C, 205C and any one of 209T/G, 212D and 218D/H/C; 162C, 205S and any one of 209T/G, 212D and 218D/H/C; 162C, 209T and any one of 212D and 218D/H/C; 162C, 209G and any one of 212D and 218D/H/C; 165M, 191D and any one of 193E/P/H, 194P/I, 198E/P, 199D, 201P, 205C/S, 209T/G, 212D and 218D/H/C; 165M, 191E and any one of 193E/P/H, 194P/I, 198E/P, 199D, 201P, 205C/S, 209T/G, 212D and 218D/H/C; 165M, 191P and any one of 193E/P/H, 194P/I, 198E/P, 199D, 201P, 205C/S, 209T/G, 212D and 218D/H/C; 165M, 191H and any one of 193E/P/H, 194P/I, 198E/P, 199D, 201P, 205C/S, 209T/G, 212D and 218D/H/C; 165M, 193E and any one of 194P/I, 198E/P, 199D, 201P, 205C/S, 209T/G, 212D and 218D/H/C; 165M, 193P and any one of 194P/I, 198E/P, 199D, 201P, 205C/S, 209T/G, 212D and 218D/H/C; 165M, 193H and any one of 194P/I, 198E/P, 199D, 201P, 205C/S, 209T/G, 212D and 218D/H/C; 165M, 194P and any one of 198E/P, 199D, 201P, 205C/S, 209T/G, 212D and 218D/H/C; 165M, 194I and any one of 198E/P, 199D, 201P, 205C/S, 209T/G, 212D and 218D/H/C; 165M, 198E and any one of 199D, 201P, 205C/S, 209T/G, 212D and 218D/H/C; 165M, 198P and any one of 199D, 201P, 205C/S, 209T/G, 212D and 218D/H/C; 165M, 205C and any one of 209T/G, 212D and 218D/H/C; 165M, 205S and any one of 209T/G, 212D and 218D/H/C; 165M, 209T and any one of 212D and 218D/H/C; 165M, 209G and any one of 212D and 218D/H/C; 171D, 191D and any one of 193E/P/H, 194P/I, 198E/P, 199D, 201P, 205C/S, 209T/G, 212D and 218D/H/C; 171D, 191E and any one of 193E/P/H, 194P/I, 198E/P, 199D, 201P, 205C/S, 209T/G, 212D and 218D/H/C; 171D, 191P and any one of 193E/P/H, 194P/I, 198E/P, 199D, 201P, 205C/S, 209T/G, 212D and 218D/H/C; 171D, 191H and any one of 193E/P/H, 194P/I, 198E/P, 199D, 201P, 205C/S, 209T/G, 212D and 218D/H/C; 171D, 193E and any one of 194P/I, 198E/P, 199D, 201P, 205C/S, 209T/G, 212D and 218D/H/C; 171D, 193P and any one of 194P/I, 198E/P, 199D, 201P, 205C/S, 209T/G, 212D and 218D/H/C; 171D, 193H and any one of 194P/I, 198E/P, 199D, 201P, 205C/S, 209T/G, 212D and 218D/H/C; 171D, 194P and any one of 198E/P, 199D, 201P, 205C/S, 209T/G, 212D and 218D/H/C; 171D, 194I and any one of 198E/P, 199D, 201P, 205C/S, 209T/G, 212D and 218D/H/C; 171D, 198E and any one of 199D, 201P, 205C/S, 209T/G, 212D and 218D/H/C; 171D, 198P and any one of 199D, 201P, 205C/S, 209T/G, 212D and 218D/H/C; 171D, 205C and any one of 209T/G, 212D and 218D/H/C; 171D, 205S and any one of 209T/G, 212D and 218D/H/C; 171D, 209T and any one of 212D and 218D/H/C; 171D, 209G and any one of 212D and 218D/H/C; 179D, 191D and any one of 193E/P/H, 194P/I, 198E/P, 199D, 201P, 205C/S, 209T/G, 212D and 218D/H/C; 179D, 191E and any one of 193E/P/H, 194P/I, 198E/P, 199D, 201P, 205C/S, 209T/G, 212D and 218D/H/C; 179D, 191P and any one of 193E/P/H, 194P/I, 198E/P, 199D, 201P, 205C/S, 209T/G, 212D and 218D/H/C; 179D, 191H and any one of 193E/P/H, 194P/I, 198E/P, 199D, 201P, 205C/S, 209T/G, 212D and 218D/H/C; 179D, 193E and any one of 194P/I, 198E/P, 199D, 201P, 205C/S, 209T/G, 212D and 218D/H/C; 179D, 193P and any one of 194P/I, 198E/P, 199D, 201P, 205C/S, 209T/G, 212D and 218D/H/C; 179D, 193H and any one of 194P/I, 198E/P, 199D, 201P, 205C/S, 209T/G, 212D and 218D/H/C; 179D, 194P and any one of 198E/P, 199D, 201P, 205C/S, 209T/G, 212D and 218D/H/C; 179D, 194I and any one of 198E/P, 199D, 201P, 205C/S, 209T/G, 212D and 218D/H/C; 179D, 198E and any one of 199D, 201P, 205C/S, 209T/G, 212D and 218D/H/C; 179D, 198P and any one of 199D, 201P, 205C/S, 209T/G, 212D and 218D/H/C; 179D, 205C and any one of 209T/G, 212D and 218D/H/C; 179D, 205S and any one of 209T/G, 212D and 218D/H/C; 179D, 209T and any one of 212D and 218D/H/C; 179D, 209G and any one of 212D and 218D/H/C; 188H, 191D and any one of 193E/P/H, 194P/I, 198E/P, 199D, 201P, 205C/S, 209T/G, 212D and 218D/H/C; 188H, 191E and any one of 193E/P/H, 194P/I, 198E/P, 199D, 201P, 205C/S, 209T/G, 212D and 218D/H/C; 188H, 191P and any one of 193E/P/H, 194P/I, 198E/P, 199D, 201P, 205C/S, 209T/G, 212D and 218D/H/C; 188H, 191H and any one of 193E/P/H, 194P/I, 198E/P, 199D, 201P, 205C/S, 209T/G, 212D and 218D/H/C; 188H, 193E and any one of 194P/I, 198E/P, 199D, 201P, 205C/S, 209T/G, 212D and 218D/H/C; 188H, 193P and any one of 194P/I, 198E/P, 199D, 201P, 205C/S, 209T/G, 212D and 218D/H/C; 188H, 193H and any one of 194P/I, 198E/P, 199D, 201P, 205C/S, 209T/G, 212D and 218D/H/C; 188H, 194P and any one of 198E/P, 199D, 201P, 205C/S, 209T/G, 212D and 218D/H/C; 188H, 194I and any one of 198E/P, 199D, 201P, 205C/S, 209T/G, 212D and 218D/H/C; 188H, 198E and any one of 199D, 201P, 205C/S, 209T/G, 212D and 218D/H/C; 188H, 198P and any one of 199D, 201P, 205C/S, 209T/G, 212D and 218D/H/C; 188H, 205C and any one of 209T/G, 212D and 218D/H/C; 188H, 205S and any one of 209T/G, 212D and 218D/H/C; 188H, 209T and any one of 212D and 218D/H/C; 188H, 209G and any one of 212D and 218D/H/C; 190Q, 191D and any one of 193E/P/H, 194P/I, 198E/P, 199D, 201P, 205C/S, 209T/G, 212D and 218D/H/C; 190Q, 191E and any one of 193E/P/H, 194P/I, 198E/P, 199D, 201P, 205C/S, 209T/G, 212D and 218D/H/C; 190Q, 191P and any one of 193E/P/H, 194P/I, 198E/P, 199D, 201P, 205C/S, 209T/G, 212D and 218D/H/C; 190Q, 191H and any one of 193E/P/H, 194P/I, 198E/P, 199D, 201P, 205C/S, 209T/G, 212D and 218D/H/C; 190Q, 193E and any one of 194P/I, 198E/P, 199D, 201P, 205C/S, 209T/G, 212D and 218D/H/C; 190Q, 193P and any one of 194P/I, 198E/P, 199D, 201P, 205C/S, 209T/G, 212D and 218D/H/C; 190Q, 193H and any one of 194P/I, 198E/P, 199D, 201P, 205C/S, 209T/G, 212D and 218D/H/C; 190Q, 194P and any one of 198E/P, 199D, 201P, 205C/S, 209T/G, 212D and 218D/H/C; 190Q, 194I and any one of 198E/P, 199D, 201P, 205C/S, 209T/G, 212D and 218D/H/C; 190Q, 198E and any one of 199D, 201P, 205C/S, 209T/G, 212D and 218D/H/C; 190Q, 198P and any one of 199D, 201P, 205C/S, 209T/G, 212D and 218D/H/C; 190Q, 205C and any one of 209T/G, 212D and 218D/H/C; 190Q, 205S and any one of 209T/G, 212D and 218D/H/C; 190Q, 209T and any one of 212D and 218D/H/C; 190Q, 209G and any one of 212D and 218D/H/C; 191D, 193E and any one of 194P/I, 198E/P, 199D, 201P, 205C/S, 209T/G, 212D and 218D/H/C; 191D, 193P and any one of 194P/I, 198E/P, 199D, 201P, 205C/S, 209T/G, 212D and 218D/H/C; 191D, 193H and any one of 194P/I, 198E/P, 199D, 201P, 205C/S, 209T/G, 212D and 218D/H/C; 191E, 193E and any one of 194P/I, 198E/P, 199D, 201P, 205C/S, 209T/G, 212D and 218D/H/C; 191E, 193P and any one of 194P/I, 198E/P, 199D, 201P, 205C/S, 209T/G, 212D and 218D/H/C; 191E, 193H and any one of 194P/I, 198E/P, 199D, 201P, 205C/S, 209T/G, 212D and 218D/H/C; 191P, 193E and any one of 194P/I, 198E/P, 199D, 201P, 205C/S, 209T/G, 212D and 218D/H/C; 191P, 193P and any one of 194P/I, 198E/P, 199D, 201P, 205C/S, 209T/G, 212D and 218D/H/C; 191P, 193H and any one of 194P/I, 198E/P, 199D, 201P, 205C/S, 209T/G, 212D and 218D/H/C; 191H, 193E and any one of 194P/I, 198E/P, 199D, 201P, 205C/S, 209T/G, 212D and 218D/H/C; 191H, 193P and any one of 194P/I, 198E/P, 199D, 201P, 205C/S, 209T/G, 212D and 218D/H/C; 191H, 193H and any one of 194P/I, 198E/P, 199D, 201P, 205C/S, 209T/G, 212D and 218D/H/C; 191D, 194P and any one of 198E/P, 199D, 201P, 205C/S, 209T/G, 212D and 218D/H/C; 191D, 194I and any one of 198E/P, 199D, 201P, 205C/S, 209T/G, 212D and 218D/H/C; 191E, 194P and any one of 198E/P, 199D, 201P, 205C/S, 209T/G, 212D and 218D/H/C; 191E, 194I and any one of 198E/P, 199D, 201P, 205C/S, 209T/G, 212D and 218D/H/C; 191P, 194P and any one of 198E/P, 199D, 201P, 205C/S, 209T/G, 212D and 218D/H/C; 191P, 194I and any one of 198E/P, 199D, 201P, 205C/S, 209T/G, 212D and 218D/H/C; 191H, 194P and any one of 198E/P, 199D, 201P, 205C/S, 209T/G, 212D and 218D/H/C; 191H, 194I and any one of 198E/P, 199D, 201P, 205C/S, 209T/G, 212D and 218D/H/C; 191D, 198E and any one of 199D, 201P, 205C/S, 209T/G, 212D and 218D/H/C; 191D, 198P and any one of 199D, 201P, 205C/S, 209T/G, 212D and 218D/H/C; 191E, 198E and any one of 199D, 201P, 205C/S, 209T/G, 212D and 218D/H/C; 191E, 198P and any one of 199D, 201P, 205C/S, 209T/G, 212D and 218D/H/C; 191P, 198E and any one of 199D, 201P, 205C/S, 209T/G, 212D and 218D/H/C; 191P, 198P and any one of 199D, 201P, 205C/S, 209T/G, 212D and 218D/H/C; 191H, 198E and any one of 199D, 201P, 205C/S, 209T/G, 212D and 218D/H/C; 191H, 198P and any one of 199D, 201P, 205C/S, 209T/G, 212D and 218D/H/C; 191D, 199D and any one of 201P, 205C/S, 209T/G, 212D and 218D/H/C; 191E, 199D and any one of 201P, 205C/S, 209T/G, 212D and 218D/H/C; 191P, 199D and any one of 201P, 205C/S, 209T/G, 212D and 218D/H/C; 191H, 199D and any one of 201P, 205C/S, 209T/G, 212D and 218D/H/C; 191D, 201P and any one of 205C/S, 209T/G, 212D and 218D/H/C; 191E, 201P and any one of 205C/S, 209T/G, 212D and 218D/H/C; 191P, 201P and any one of 205C/S, 209T/G, 212D and 218D/H/C; 191H, 201P and any one of 205C/S, 209T/G, 212D and 218D/H/C; 191D, 205C and any one of 209T/G, 212D and 218D/H/C; 191D, 205S and any one of 209T/G, 212D and 218D/H/C; 191E, 205C and any one of 209T/G, 212D and 218D/H/C; 191E, 205S and any one of 209T/G, 212D and 218D/H/C; 191P, 205C and any one of 209T/G, 212D and 218D/H/C; 191P, 205S and any one of 209T/G, 212D and 218D/H/C; 191H, 205C and any one of 209T/G, 212D and 218D/H/C; 191H, 205S and any one of 209T/G, 212D and 218D/H/C; 191D, 209T and any one of 212D and 218D/H/C; 191D, 209G and any one of 212D and 218D/H/C; 191E, 209T and any one of 212D and 218D/H/C; 191E, 209G and any one of 212D and 218D/H/C; 191P, 209T and any one of 212D and 218D/H/C; 191P, 209G and any one of 212D and 218D/H/C; 191H, 209T and any one of 212D and 218D/H/C; 191H, 209G and any one of 212D and 218D/H/C; 191D, 212D and 218D/H/ C; 191E, 212D and 218D/H/C; 191P, 212D and 218D/H/C; 191H, 212D and 218D/H/C; 193E, 194P and any one of 198E/P, 199D, 201P, 205C/S, 209T/G, 212D and 218D/H/C; 193E, 194I and any one of 198E/P, 199D, 201P, 205C/S, 209T/G, 212D and 218D/H/C; 193P, 194P and any one of 198E/P, 199D, 201P, 205C/S, 209T/G, 212D and 218D/H/C; 193P, 194I and any one of 198E/P, 199D, 201P, 205C/S, 209T/G, 212D and 218D/H/C; 193H, 194P and any one of 198E/P, 199D, 201P, 205C/S, 209T/G, 212D and 218D/H/C; 193H, 194I and any one of 198E/P, 199D, 201P, 205C/S, 209T/G, 212D and 218D/H/C;

193E, 198E and any one of 199D, 201P, 205C/S, 209T/G, 212D and 218D/H/C; 193E, 198P and any one of 199D, 201P, 205C/S, 209T/G, 212D and 218D/H/C; 193P, 198E and any one of 199D, 201P, 205C/S, 209T/G, 212D and 218D/H/C; 193P, 198P and any one of 199D, 201P, 205C/S, 209T/G, 212D and 218D/H/C; 193H, 198E and any one of 199D, 201P, 205C/S, 209T/G, 212D and 218D/H/C; 193H, 198P and any one of 199D, 201P, 205C/S, 209T/G, 212D and 218D/H/C; 193E, 199D and any one of 201P, 205C/S, 209T/G, 212D and 218D/H/C; 193P, 199D and any one of 201P, 205C/S, 209T/G, 212D and 218D/H/C; 193H, 199D and any one of 201P, 205C/S, 209T/G, 212D and 218D/H/C; 193E, 201P and any one of 205C/S, 209T/G, 212D and 218D/H/C; 193P, 201P and any one of 205C/S, 209T/G, 212D and 218D/H/C; 193H, 201P and any one of 205C/S, 209T/G, 212D and 218D/H/C; 193E, 205C and any one of 209T/G, 212D and 218D/H/C; 193E, 205S and any one of 209T/G, 212D and 218D/H/C; 193P, 205C and any one of 209T/G, 212D and 218D/H/C; 193P, 205S and any one of 209T/G, 212D and 218D/H/C; 193H, 205C and any one of 209T/G, 212D and 218D/H/C; 193H, 205S and any one of 209T/G, 212D and 218D/H/C; 193E, 209T and any one of 212D and 218D/H/C; 193E, 209G and any one of 212D and 218D/H/C; 193P, 209T and any one of 212D and 218D/H/C; 193P, 209G and any one of 212D and 218D/H/C; 193H, 209T and any one of 212D and 218D/H/C; 193H, 209G and any one of 212D and 218D/H/C; 193E, 212D and 218D/H/ C; 193P, 212D and 218D/H/C; 193H, 212D and 218D/H/C; 194P, 198E and any one of 199D, 201P, 205C/S, 209T/G, 212D and 218D/H/C; 194P, 198P and any one of 199D, 201P, 205C/S, 209T/G, 212D and 218D/H/C; 194I, 198P and any one of 199D, 201P, 205C/S, 209T/G, 212D and 218D/H/C; 194I, 198E and any one of 199D, 201P, 205C/S, 209T/G, 212D and 218D/H/C; 194P, 199D and any one of 201P, 205C/S, 209T/G, 212D and 218D/H/C; 194I, 199D and any one of 201P, 205C/S, 209T/G, 212D and 218D/H/C; 194P, 201P and any one of 205C/S, 209T/G, 212D and 218D/H/C; 194I, 201P and any one of 205C/S, 209T/G, 212D and 218D/H/C; 194P, 205C and any one of 209T/G, 212D and 218D/H/C; 194P, 205S and any one of 209T/G, 212D and 218D/H/C; 194I, 205C and any one of 209T/G, 212D and 218D/H/C; 194I, 205S and any one of 209T/G, 212D and 218D/H/C; 194P, 209T and any one of 212D and 218D/H/C; 194P, 209G and any one of 212D and 218D/H/C; 194I, 209T and any one of 212D and 218D/H/C; 194I, 209G and any one of 212D and 218D/H/C; 194P, 212D and 218D/H/C; 194I, 212D and 218D/H/C; 198E, 199D and any one of 201P, 205C/S, 209T/G, 212D and 218D/H/C; 198P, 199D and any one of 201P, 205C/S, 209T/G, 212D and 218D/H/C; 198E, 201P and any one of 205C/S, 209T/G, 212D and 218D/H/C; 198P, 201P and any one of 205C/S, 209T/G, 212D and 218D/H/C; 198E, 205C and any one of 209T/G, 212D and 218D/H/C; 198E, 205S and any one of 209T/G, 212D and 218D/H/C; 198P, 205C and any one of 209T/G, 212D and 218D/H/C; 198P, 205S and any one of 209T/G, 212D and 218D/H/C; 198E, 209T and any one of 212D and 218D/H/C; 198E, 209G and any one of 212D and 218D/H/C; 198P, 209T and any one of 212D and 218D/H/C; 198P, 209G and any one of 212D and 218D/H/C; 198E, 212D and 218D/H/C; 198P, 212D and 218D/H/C; 199D, 205C and any one of 209T/G, 212D and 218D/H/C; 199D, 205S and any one of 209T/G, 212D and 218D/H/C; 199D, 209T and any one of 212D and 218D/H/C; 199D, 209G and any one of 212D and 218D/H/C; 201P, 205C and any one of 209T/G, 212D and 218D/H/C; 201P, 205S and any one of 209T/G, 212D and 218D/H/C; 201P, 209T and any one of 212D and 218D/H/C; 201P, 209G and any one of 212D and 218D/H/C; 205C, 209T and any one of 212D and 218D/H/ C; 205C, 209G and any one of 212D and 218D/H/C; 205S, 209T and any one of 212D and 218D/H/C; 205S, 209G and any one of 212D and 218D/H/C; 205C, 212D and 218D/H/ C; 205S, 212D and 218D/H/C; 209G, 212D and 218D/H/C; 209T, 212D and 218D/H/C.

The disclosure also covers fragments of the identified variants. As such fragments are technically also variants comprising deletions, there is an overlap in terminology if the variant comprises one or more deletions, in particular deletions of amino acids at the N- or C-terminus. In various embodiments, said fragments of the variants are at least 50 amino acids in length and retain at least one of the one or more amino acid substitution(s) or deletion(s). In various embodiments, said fragments comprise at least one GG repeat sequence, preferably two, three or 4 GG repeat sequences, as defined below, and/or the C-terminal secretion sequence, i.e. the 40 C-terminal amino acids of SEQ ID NO:1, preferably the 50 C-terminal amino acids of SEQ ID NO:1, more preferably the 55 or 60 C-terminal amino acids of SEQ ID NO:1. In some other embodiments, said fragments comprise deletions of at least the amino acids corresponding to positions 215-218 of SEQ ID NO:1. In addition, any one or more of the amino acids up to the position corresponding to position 109 of SEQ ID NO:1 (starting from 218 and counting backwards) may be deleted, thus effectively covering deletion of all positions indicated herein. Such deletions may cover the amino acid residues at the positions corresponding to positions 185-218, positions 165-218, positions 135-218 or positions 110-218 of SEQ ID NO:1. Also encompassed are any deletions of ranges between those recited above, such as 184-218, 183-218, 182-218, 181-218, 180-218, 179-218, 178-218, 177-218, 176-218, 175-218, 174-218, 173-218, 172-218, 171-218, 170-218, 169-218, 168-218, 167-218, 166-218, 165-218, 164-218, 163-218, 162-218, 161-218, 160-218, 159-218, 158-218, 157-218, 156-218, 155-218, 154-218; 153-218; 152-218; 151-218; 150-218; 149-218; 148-218; 147-218; 146-218; 145-218; 144-218; 143-218; 142-218; 141-218; 140-218; 139-218; 138-218; 137-218; 136-218; 134-218; 133-218; 132-218; 131-218; 130-218; 129-218; 128-218; 127-218; 126-218; 125-218; 124-218; 123-218; 122-218; 121-218; 120-218; 119-218; 118-218; 117-218; 116-218; 115-218; 114-218; 113-218; 112-218; and 111-218. Furthermore, deletions of the amino acids at the positions corresponding to positions 215-218 of SEQ ID NO:1 may be combined with deletions at the positions corresponding to positions 165-182, such as 165-168, 165-169, 165-170, 165-171, 165-172, 165-173, 165-174, 165-175, 165-176, 165-177, 165-178, 165-179, 165-180, and 165-181. In various embodiments, the fragments of the amino acid sequence set forth in SEQ ID NO:1 include at least amino acids at positions corresponding to positions 10-68 of SEQ ID NO:1, preferably 1-68, more preferably 1-75, even more preferably 1-90, 1-100, 1-105 or 1-109 of SEQ ID NO:1. In various other embodiments, the first amino acid sequence is not C-terminally truncated. This may mean that it comprises an intact C-terminus comprising the 40, preferably 45, 50, 55 or 60, C-terminal amino acids of SEQ ID NO:1. These may however include the substitutions disclosed herein as well as 5 or less, for example 4, 3, 2, 1 or 0, single amino acid deletions.

In some embodiments, the first amino acid sequence may thus be derived from the amino acid sequence set forth in SEQ ID NO:1 by any one or more of an N-terminal truncation, a C-terminal truncation, both or a deletion of one or more amino acids. The first amino acid sequence may be at least 50 amino acids in length, preferably at least 60, 70, 80, 90, 100, 110, 120, 130, 140, 150, 160, 170, 180, 190, 200, 210, 211, 212, 213, 214, 215, 216, 217 or 218 amino acids in length. In various embodiments, the fragment has a C-terminal truncation, for example of amino acids in the positions corresponding to positions 215-218, 214-218, 185-218, 165-218, 135-218, or 111-218 of SEQ ID NO:1. In various embodiments the C-terminal end up to amino acid 110 (not including 110) in the numbering of SEQ ID NO:1 may be truncated. In various other embodiments, the amino acids in positions corresponding to positions 215-218 or 214-218 of SEQ ID NO:1 and additionally in the positions corresponding to positions 164-168, 165-168, 164-173, 165-173, 164-183, 165-183 or 165-182 of SEQ ID NO:1 may be deleted. In various embodiments any continuous 4 or more amino acids in the region corresponding to positions 164-183 of SEQ ID NO:1, in particular starting from position 164 or 165 and up to position 182 or 183 may be deleted. Exemplary embodiments of such truncations/deletions are set forth in SEQ ID Nos. 22-28. In various other embodiments, in particular in embodiments where secretion of the polypeptide is desired, the first amino acid sequence is not C-terminally truncated. This may mean that it comprises an intact C-terminus comprising the 40, preferably 45, 50, 55 or 60, C-terminal amino acids of SEQ ID NO:1. These may however include the substitutions disclosed herein as well as 5 or less, for example 4, 3, 2, 1 or 0, single amino acid deletions. It has been found that the deletions and/or substitutions disclosed herein may even increase stability of secreted proteins.

If any of the positions indicated above as being suitable for amino acid substitutions are retained in the fragment sequences described herein, these may be substituted in accordance with the present disclosure.

The first amino acid sequence is, in various embodiments, 30 to 218 amino acids in length. The lower limit may be 35, 40, 45, 50, 55, 60, 65, 70, 75, 80, 85, 90, 95 or 100 amino acids in length. In various embodiments, it may be preferred that the first amino acid sequence is as short as possible, as long as its beneficial influence on expression levels and/or yields is not impaired and it retains sufficiently high solubility and/or proteolytic stability. Generally, the skilled person will know how to find a balance between a sequence that is as short as possible while still providing for the desired expression levels/yields within the scope defined by the claims.

While the first amino acid sequence may correspond to a continuous amino acid stretch of the amino acid sequence set forth in SEQ ID NO:1 having the indicated length, it is similarly possible that the first amino acid sequence corresponds to discontinuous stretches of the amino acid sequence set forth in SEQ ID NO:1, for example if it corresponds to stretches of SEQ ID NO:1 with certain amino acids or amino acid sequences being deleted therefrom. The first amino acid sequence may thus be derived from the amino acid sequence set forth in SEQ ID NO:1 by any one or more of an N-terminal truncation, a C-terminal truncation or a deletion of one or more amino acids, in particular as described above.

In various embodiments, if the first amino acid sequence comprises a deletion relative to SEQ ID NO:1, the first amino acid sequence does not comprise any one of the full amino acid sequences of SEQ ID Nos. 46-50 as set forth in WO 2013/057312 A1. In various other embodiments, the first amino acid sequence does not comprise any one of the full amino acid sequences of SEQ ID Nos. 33, 34, 36 of EP 2 583 975 A1, as well as SEQ ID Nos. 4 and 7 of WO 2006/036406 A2 and EPOP:A12703 (200 aa long C-terminal fragment of HlyA) of WO 8706953 A1.

In various embodiments, the first amino acid sequence, comprising any one or more amino acid substitution(s) and/or deletion(s) defined herein, comprises at least one GG repeat sequence of SEQ ID NO:1. "GG repeat" as used herein, relates to the consensus sequence GGxGxDxUx, wherein x can be any amino acid and U is a hydrophobic, large amino acid, such as F, W, Y, I, L, M. SEQ ID NO:1 comprises 3 such GG repeats in its sequence. These span residues 11-19, 29-37, and 38-46 of SEQ ID NO:1 and have the sequences GGKGNDKLY (SEQ ID NO:2), GGEGD-DLLK (SEQ ID NO:3) and GGYGNDIYR (SEQ ID NO:4). Another glycine-rich sequence spans amino acids 60-67 of SEQ ID NO:1 (GGKEDKLS; SEQ ID NO:5) and may also be comprised in the first amino acid sequence.

The presence of one or more of these GG repeat sequences may, in some embodiments, facilitate secretion/refolding of the polypeptide either after secretion or purification. However, the expression level as such is not necessarily influenced by the presence or absence of a GG repeat sequence.

In various embodiments, the first amino acid sequence comprises the sequence set forth in any one of SEQ ID Nos. 6-28. In further embodiments, also encompassed are variants of these sequences that have at least 80%, at least 85%, at least 90%, at least 95%, at least 97.5%, at least 99% or at least 99.5% sequence identity with the amino acid sequence set forth in the respective template sequence of any one of SEQ ID Nos. 6-28. These variants include truncated versions of the sequences set forth in SEQ ID Nos. 6-28, for example N- or C-terminal truncations, preferably C-terminal truncations, with these truncations (i.e. the deleted amino acid stretches) typically being 1-10, preferably 1-5 amino acids in length. N-terminal truncations are generally not preferred. In particular, the amino acid sequence set forth in SEQ ID Nos. 22-28, which are already truncated versions of SEQ ID NO:1 are preferably not further truncated, or truncated only by 1-10 amino acids, preferably on the C-terminal end.

The isolated polypeptide typically comprises a second amino acid sequence N-terminal or C-terminal to the first amino acid sequence, wherein the second amino acid sequence is at least one peptide or polypeptide of interest. The second amino acid sequence may be 2 to 500 amino acids in length, preferably 10, 12 or 15 to 200, 180, 150, 120 or 100 amino acids in length. The terms "second amino acid sequence" and the terms "peptide of interest" and "polypeptide/protein of interest" are used interchangeably herein.

In various embodiments, the peptide or protein of interest may comprise two or more naturally occurring peptides or proteins, the two or more peptides or proteins may be separated by protease cleavage sites. This also includes embodiments, where the same peptide or protein is included multiple times in said second amino acid sequence. This then allows production of higher amounts of the respective peptide or protein of interest. In other embodiments, the peptide or protein of interest is only a single peptide or protein.

Generally, any peptide or protein may be chosen as protein of interest. In certain embodiments, the protein of interest is a protein, which does not form a homo-dimer or homo-multimer. The avoidance of self-interacting peptides or proteins may be advantageous if the recombinant peptide or protein is to be secreted into the cell culture supernatant, because the formation of larger protein complexes may disturb an efficient protein export. However, the protein of interest may also be a peptide or protein which is a subunit of a larger peptide or protein complex. Such a peptide or protein may be isolated after expression and optionally secretion and be suitable for an in vitro reconstitution of the multi peptide or protein complex. In certain embodiments, the protein or peptide of interest is a protein or peptide having less than 500 amino acid residues, for example less than 200 amino acids or less than 150 amino acids. If these peptides comprise pre- and/or pro-sequences in their native state after translation the nucleic acid sequence encoding for the peptide of interest may be engineered to be limited to the sequence encoding the mature peptide. One exemplary peptide is insulin, e.g., human insulin. The expression of over-expressed peptides and proteins as inclusion bodies is especially advantageous where the peptide or protein is harmful to the host cell. Lipases and proteases are known to be toxic to the host cell and thus the expression of these proteins claimed systems and methods are advantageous.

In various embodiments, the peptide or protein of interest is an enzyme. The International Union of Biochemistry and Molecular Biology has developed a nomenclature for enzymes, the EC numbers; each enzyme is described by a sequence of four numbers preceded by "EC". The first number broadly classifies the enzyme based on its mechanism. The complete nomenclature can be browsed at http://www.chem.qmul.ac.uk/iubmb/enzyme/.

Accordingly, a peptide or protein of interest may be chosen from any of the classes EC 1 (Oxidoreductases), EC 2 (Transferases), EC 3 (Hydrolases), EC 4 (Lyases), EC 5 (Isomerases), and EC 6 (Ligases), and the subclasses thereof.

In certain embodiments, the peptide or protein of interest is cofactor dependent or harbors a prosthetic group. For expression of such peptides or proteins, in some embodiments, the corresponding cofactor or prosthetic group may be added to the culture medium during expression.

In certain cases, the peptide or protein of interest is a dehydrogenase or an oxidase. In case the peptide or protein of interest is a dehydrogenase, in some embodiments, the peptide or protein of interest is chosen from the group consisting of alcohol dehydrogenases, glutamate dehydrogenases, lactate dehydrogenases, cellobiose dehydrogenases, formate dehydrogenases, and aldehydes dehydrogenases. In case the peptide or protein of interest is an oxidase, in some embodiments, the peptide or protein of interest is chosen from the group consisting of cytochrome P450 oxidoreductases, in particular P450 BM3 and mutants thereof, peroxidases, monooxygenases, hydrogenases, monoamine oxidases, aldehydes oxidases, xanthin oxidases, amino acid oxidases, and NADH oxidases.

In further embodiments, the peptide or protein of interest is a transaminase or a kinase. In case the peptide or protein of interest is a transaminase, in some embodiments, the peptide or protein of interest is chosen from the group consisting of alanine aminotransferases, aspartate aminotransferases, glutamate-oxaloacetic transaminases, histidinol-phosphate transaminases, and histidinol-pyruvate transaminases. In various embodiments, if the peptide or protein of interest is a kinase, the peptide or protein of interest is chosen from the group consisting of nucleoside diphosphate kinases, nucleoside monophosphate kinases, pyruvate kinase, and glucokinases. In some embodiments, if the peptide or protein of interest is a hydrolase, the peptide or protein of interest is chosen from the group consisting of lipases, amylases, proteases, cellulases, nitrile hydrolases, halogenases, phospholipases, and esterases.

In certain embodiments, if the peptide or protein of interest is a lyase, the peptide or protein of interest is chosen from the group consisting of aldolases, e.g., hydroxynitrile lyases, thiamine-dependent enzymes, e.g., benzaldehyde lyases, and pyruvate decarboxylases. In various embodiments, if the peptide or protein of interest is an isomerase, the peptide or protein of interest is chosen from the group consisting of isomerases and mutases.

In some embodiments, if the peptide or protein of interest is a ligase, the peptide or protein of interest may be a DNA ligase.

In certain embodiments, the peptide or protein of interest may be an antibody. This may include a complete immunoglobulin or fragment thereof, which immunoglobulins include the various classes and isotypes, such as IgA, IgD, IgE, IgGI, IgG2a, IgG2b and IgG3, IgM, etc. Fragments thereof may include Fab, Fv and F(ab')2, Fab', the variable domain of the light chain (VL) or the variable domain of the heavy chain (VH) and related fragments, such as nanobodies, and the like.

Also contemplated herein are therapeutically active peptides and proteins of interest, e.g., cytokines.

Thus, in certain embodiments the peptide or protein of interest is selected from the group consisting cytokines, in particular human or murine interferons, interleukins (IL-1, IL-2, IL-3, IL-4; IL-5; IL-6; IL-7; IL-8; IL-9; IL-10; IL-11; IL-12; IL-13; IL-14; IL-15; IL-16; and IL-17), colony-stimulating factors, necrosis factors, e.g., tumor necrosis factor, such as TNF alpha, and growth factors, such as transforming growth factor beta family members, such as TGF-beta1; TGF-beta2 and TGF-beta3.

In some embodiments, if the peptide or protein of interest is an interferon, the peptide or protein of interest may be selected from the group consisting of interferon alpha, e.g., alpha-1, alpha-2, alpha-2a, and alpha-2b, alpha-2, alpha-16, alpha 21, beta, e.g., beta-1, beta-1a, and beta-1b, or gamma.

In further embodiments, the peptide or protein of interest is an antimicrobial peptide, in particular a peptide selected from the group consisting of bacteriocines and Iantibiotics, e.g., nisin, cathelicidins, defensins, and saposins.

Also disclosed herein are peptides or proteins of interest which are therapeutically active peptides or proteins. In certain embodiments, the peptide or protein of interest is a therapeutically active peptide. In some embodiments, a therapeutically active peptide may be selected from the group consisting of Fuzeon/T20, human calcitonin, salmon calcitonin, human corticotropin release factor, Mab40, Mab42, peptides associated with Alzheimer's disease, exenatide, Tesamorelin, Teriparatide, BMP-2, Corticorelin ovine triflutate, Linaclotide, Nesiritide, Lucinactant, Bivalirudin, Lepirudin, Thymalfasin, Glatiramer, Glucagon, Aviptadil, Secretin, Thymosin-b4, Teduglutide, GLP-1, GLP-2 and analoga, Plecanatide, Ecallantide, Anakinra, Disiteritide, Lixisenatide, Liraglutide, Semaglutide, Abaloparatide, Goserelin, Lanreotide, Carfilzomib, Enfuvirtide, T-20, Terlipressin, Elcatonin, Afamelanotide, Oxodotreotide, Caspofungin, Colistin, Polymyxin E, Cyclosporine, Dactinomcyin, Lyovac-Cosmegen, Degarelix, Vancomycin, Secretin, Ziconotide, Gonadorelin, Somastatin, Sincalide, Eptifibatid, Vapreotide, Triptorelin, Desmopressin, Lypressin, Atosiban, Pramintide, Pasireotide, Sandostatin, and Icatibant. The afore-mentioned peptides may be of mammalian or human origin. Also encompassed are analogues of the afore-mentioned peptides that originate from other species, for example homologues from other animals, microorganisms, virus and others.

In certain embodiments, the peptide or protein of interest is a type I secretion substrate. More than 1000 proteins are annotated or have been described as type I secretion substrates in the literature. Many of them have interesting characteristics for the biotechnological usage, in particular proteases and lipases. Suitable proteases and lipases have been described by Baumann et al. (1993) EMBO J 12, 3357-3364; and Meier et al. (2007) J. BIOL. CHEM.: 282(43), pp. 31477-31483. The content of each of these documents is incorporated by reference herein in its entirety.

In certain embodiments, the second amino acid sequence is a peptide or protein of interest which is chosen from the group consisting of MBP, lipase CalB, protease SprP, hydrolase PlaB, hydrolase PlaK, hydrolase PlbF, lipase TesA, Vif, human interferon alpha-1, alpha-2, alpha-8, alpha-16, alpha-21, human interferon beta, human interferon gamma, murine interferon alpha, murine interferon gamma, IFABP, Cas2, affibody protein ZA3, nisin, corticotropin release factor, amyloid-beta peptide, exenatide, Fuzeon/T20, salmon calcitonin, Mab40, Mab42, lipase LipA, SprP, the HIV-1 protein Vif, human calcitonin, Tesamorelin, Teriparatide, BMP-2, Corticorelin ovine triflutate, Linaclotide, Nesiritide, Lucinactant, Bivalirudin, Lepirudin, Thymalfasin, Glatiramer, Glucagon, Aviptadil, Secretin, Thymosin-b4, Teduglutide, GLP-1, GLP-2 and analoga, Plecanatide, Ecallantide, Anakinra, Disiteritide, Lixisenatide, Liraglutide, Semaglutide, Abaloparatide, Goserelin, Lanreotide, Carfilzomib, Enfuvirtide, T-20, Terlipressin, Elcatonin, Afamelanotide, Oxodotreotide, Caspofungin, Colistin, Polymyxin E, Cyclosporine, Dactinomcyin, Lyovac-Cosmegen, Degarelix, Vancomycin, Secretin, Ziconotide, Gonadorelin, Somastatin, Sincalide, Eptifibatid, Vapreotide, Triptorelin, Desmopressin, Lypressin, Atosiban, Pramintide, Pasireotide, Sandostatin, and Icatibant.

The second amino acid sequence may be directly or via a linker sequence linked to the first amino acid sequence. It may be located N- or C-terminally relative to the first amino acid sequence, typically, for example but without limitation, if secretion is not desired or necessary, C-terminally. This means that the N-terminus of the second amino acid sequence is linked, optionally via a linker sequence, to the C-terminus of the first amino acid sequence. However, in other embodiments, the C-terminus of the second amino acid sequence may be fused, optionally via a linker sequence, to the N-terminus of the first amino acid sequence. This latter embodiment may, for example but without limitation, be used, if secretion is desired and the HlyA1 fragment has an intact C-terminal secretion sequence.

In various embodiments, the linker sequence that connects the first and second amino acid sequences is also a peptide sequence and connected to the respective ends of the first and second amino acid sequence via a peptide bond. In various embodiments, the linker sequence may be 1 to 50 amino acids in length, for example 1 to 30 amino acids or 4 to 20 or 5 to 15, 5 to 10 or 5 to 8 amino acids.

The linker sequence may be functional in that it may provide for easy cleavage and separation of the first and second amino acid. To facilitate such a purpose, it can comprise or consist of a protease recognition and cleavage site. The linker may also comprise both, a linker sequence that serves only as a link and a protease cleavage site. The linker sequence may be a G-rich sequence, for example a sequence that comprises 4 or 5 consecutive G residues, preferably followed by a S residue.

The term "protease (recognition and) cleavage site" refers to a peptide sequence which can be cleaved by a selected protease thus allowing the separation of peptide or protein sequences which are interconnected by a protease cleavage site. In certain embodiments the protease cleavage site is selected from the group consisting of a Factor Xa, a tobacco edge virus (TEV) protease, a enterokinase, a SUMO Express protease, an Arg-C proteinase, an Asp-N endopeptidases, an Asp-N endopeptidase +N-terminal Glu, a caspase 1, a caspase 2, a caspase 3, a caspase 4, a caspase 5, a caspase 6, a caspase 7, a caspase 8, a caspase 9, a caspase 10, a chymotrypsin-high specificity, a chymotrypsin-low specificity, a clostripain (Clostridiopeptidase B), a glutamyl endopeptidase, a granzyme B, a pepsin, a proline-endopeptidase, a proteinase K, Welqut protease, Clean Cut protease, a staphylococcal peptidase I, a Thrombin, a Trypsin, inteins, SprB or SpIA-E from Staphylococcus aureus, and a Thermolysin cleavage site. In various embodiments, it may be a Factor Xa, SprB or TEV protease cleavage site. It can be preferred, in some embodiments, to design the protease recognition site such that as few amino acids as possible of the recognition and cleavage site remain attached to the peptide or protein of interest. In various embodiments, a protease recognition and cleavage site is included, the site being for example a TEV protease recognition and cleavage site. The TEV protease cleavage site typically comprises the amino acid sequence ENLYFQG/S (SEQ ID NO:40) and cleaves between the Gin (Q) and Gly/Ser (G/S) residues. In various embodiments, the P1' amino acids may be A, M or C instead of G or S.

In various embodiments, the isolated polypeptide may further comprise at least one third amino acid sequence, for example an affinity tag.

The term "affinity tag" as used herein relates to entities which are coupled to a molecule of interest and allow enrichment of the complex between the molecule of interest and the affinity tag using an affinity tag receptor. In certain embodiments affinity tags may be selected from the group consisting of the Strep-tag® or Strep-tag® II, the myc-tag, the FLAG-tag, the His-tag, the small ubiquitin-like modifier (SUMO) tag, the covalent yet dissociable NorpD peptide (CYD) tag, the heavy chain of protein C (HPC) tag, the calmodulin binding peptide (CBP) tag, or the HA-tag or proteins such as Streptavidin binding protein (SBP), maltose binding protein (MBP), and glutathione-S-transferase.

In various embodiments, the isolated polypeptide has relative to a polypeptide comprising the sequence of SEQ ID NO:1 as the first amino acid sequence an equal or increased expression in a host cell under identical expression conditions. "Equal", as used in this connection, includes expression levels that are within 10%, preferably within 5%, of the yields achieved with SEQ ID NO:1 as the first amino acid sequence. In various embodiments, this equal or increased expression is tantamount to an increased peptide to fusion protein mass ratio. By shortening the expression tag, similar expression levels still mean a higher yield of the peptide of interest.

In various embodiments, the isolated polypeptide has relative to a polypeptide comprising the sequence of SEQ ID NO:1 as the first amino acid sequence an increased solubility. "Increased", as used in this connection, refers to solubility levels that are at least 10%, preferably at least 20% higher than those achieved with SEQ ID NO:1 as the first amino acid sequence. Solubility may be determined by comparing the yields of isolated polypeptides comprising as the first amino acid sequence the amino acid sequence of SEQ ID NO:1 and comprising as the first amino acid sequence a variant of SEQ ID NO:1 as described herein secreted into the host cell medium upon cultivation under otherwise identical conditions.

In various embodiments, the isolated polypeptide has relative to a polypeptide comprising the sequence of SEQ ID NO:1 as the first amino acid sequence an increased resistance to proteolytic degradation. "Increased", as used in this connection, refers to non-hydrolyzed protein levels that are at least 10%, preferably at least 20% higher than those achieved with SEQ ID NO:1 as the first amino acid sequence. Resistance to proteolytic degradation may be determined by comparing the levels of (i) hydrolysis of isolated polypeptides comprising as the first amino acid sequence the amino acid sequence of SEQ ID NO:1 and (ii) non-hydrolyzed isolated polypeptides comprising as the first amino acid sequence a variant of SEQ ID NO:1 as described herein, after cultivation under otherwise identical conditions.

In various embodiments, the isolated polypeptide has relative to a polypeptide comprising the sequence of SEQ ID NO:1 as the first amino acid sequence an increased renaturation efficiency. "Increased", as used in this connection, refers to yields of re-natured polypeptides that are at least 10%, preferably at least 20% higher than those achieved with SEQ ID NO:1 as the first amino acid sequence. Renaturation efficiency may be determined by comparing the levels of (i) renaturation of isolated polypeptides comprising as the first amino acid sequence the amino acid sequence of SEQ ID NO:1 and (ii) non-hydrolyzed isolated polypeptides comprising as the first amino acid sequence a variant of SEQ ID NO:1 as described herein, after expression in form of inclusion bodies, purification and renaturation under otherwise identical conditions.

In various embodiments, the first amino acid sequence comprises as the first, N-terminal amino acid the residue M. If this is not present within the specific sequences disclosed herein, it may be artificially added, if desired, in particular to facilitate expression in a host cell.

The nucleic acid, in particular the isolated nucleic acid molecule, may encode the polypeptide as described above. The polypeptide comprises the first amino acid sequence and optionally the second amino acid sequence and also optionally at least one third amino acid sequence. All of these amino acid sequences are typically linked by peptide bonds and expressed as a single fusion protein. To facilitate said expression, the nucleic acid molecule comprises a first nucleotide sequence encoding the first amino acid sequence and optionally a second, third and further nucleotide sequence encoding the second, third and further amino acid sequence, with said nucleotide sequences being operably linked to allow expression of the single fusion protein comprising all afore-mentioned amino acid sequences.

The term "operably linked" in the context of nucleic acid sequences means that a first nucleic acid sequence is linked to a second nucleic acid sequence such that the first nucleic acid sequence is placed in a functional relationship with the second nucleic acid sequence. For instance, a promoter sequence is operably linked to a coding sequence of a heterologous gene if the promoter can initiate the transcription of the coding sequence. In a further context, a sequence encoding for the first amino acid sequence is linked such to a second amino acid sequence encoding for a peptide or protein of interest, that if the two sequences are translated a single peptide/protein chain is obtained.

In certain embodiments, the above defined nucleic acid molecules may be comprised in a vector, for example a cloning or expression vector. Generally, the nucleic acid molecules can also be part of a vector or any other kind of cloning vehicle, including, but not limited to a plasmid, a phagemid, a phage, a baculovirus, a cosmid, or an artificial chromosome. Generally, a nucleic acid molecule disclosed in this application may be "operably linked" to a regulatory sequence (or regulatory sequences) to allow expression of this nucleic acid molecule.

Such cloning vehicles can include, besides the regulatory sequences described above and a nucleic acid sequence, replication and control sequences derived from a species compatible with the host cell that is used for expression as well as selection markers conferring a selectable phenotype on transformed or transfected cells. Large numbers of suitable cloning vectors are known in the art, and are commercially available.

In certain embodiments the nucleic acid molecules disclosed herein are comprised in a cloning vector. In some embodiments the nucleic acid molecules disclosed herein are comprised in an expression vector. The vectors may comprise regulatory elements for replication and selection markers. In certain embodiments, the selection marker may be selected from the group consisting of genes conferring ampicillin, kanamycin, chloramphenicol, tetracycline, blasticidin, spectinomycin, gentamicin, hygromycin, and zeocin resistance. In various other embodiments, the selection may be carried out using antibiotic-free systems, for example by using toxin/antitoxin systems, cer sequence, triclosan, auxotrophies or the like. Suitable methods are known to those skilled in the art.

The above-described nucleic acid molecule, comprising a nucleic acid sequence encoding for a protein of interest, if integrated in a vector, must be integrated such that the peptide or protein of interest can be expressed. Therefore, a vector comprises sequence elements which contain information regarding to transcriptional and/or translational regulation, and such sequences are "operably linked" to the nucleotide sequence encoding the polypeptide. An operable linkage in this context is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

In various embodiments, a vector comprising a nucleic acid molecule can therefore comprise a regulatory sequence, preferably a promoter sequence. In certain embodiments, the promoter is identical or homologous to promoter sequences of the host genome. In such cases endogenous polymerases may be capable to transcribe the nucleic acid molecule sequence comprised in the vector. In various embodiments, the promoter is selected from the group of weak, intermediate and strong promoters, preferably from weak to intermediate promoters.

In another preferred embodiment, a vector comprising a nucleic acid molecule comprises a promoter sequence and a transcriptional termination sequence. Suitable promoters for prokaryotic expression are, for example, the araBAD promoter, the tet-promoter, the lacUV5 promoter, the CMV promo tor, the EF1 alpha promotor, the AOX1 promotor, the tac promotor, the T7promoter, or the lac promotor. Examples of promoters useful for expression in eukaryotic cells are the SV40 promoter or the CMV promoter. Furthermore, a nucleic acid molecule can comprise transcriptional regulatory elements, e.g., repressor elements, which allow regulated transcription and translation of coding sequences comprised in the nucleic acid molecule. Repressor element may be selected from the group consisting of the Lac-, AraC-, or MalR-repressor.

The vector may be effective for prokaryotic or eukaryotic protein expression. In particular, the nucleic acid molecules may be comprised in a vector for prokaryotic protein expression. Such vector sequences are constructed such that a sequence of interest can easily be inserted using techniques well known to those skilled in the art. In certain embodiments, the vector is selected from the group consisting of a pET-vector, a pBAD-vector, a pK184-vector, a pMONO-vector, a pSELECT-vector, pSELECT-Tag-vector, a pVITRO-vector, a pVIVO-vector, a pORF-vector, a pBLAST-vector, a pUO-vector, a pDUO-vector, a pZERO-vector, a pDeNy-vector, a pDRIVE-vector, a pDRIVE-SEAP-vector, a HaloTag® Fusion-vector, a pTARGET™-vector, a Flexi®-vector, a pDEST-vector, a pHIL-vector, a pPIC-vector, a pMET-vector, a pPink-vector, a pLP-vector, a pTOPO-vector, a pBud-vector, a pCEP-vector, a pCMV-vector, a pDisplay-vector, a pEF-vector, a pFL-vector, a pFRT-vector, a pFastBac-vector, a pGAPZ-vector, a pIZ/V5-vector, a p3S-vector, a pIAR-vector, pSEC, pMS, a pSU2726-vector, a pLenti6-vector, a pMIB-vector, a pOG-vector, a pOpti-vector, a pREP4-vector, a pRSET-vector, a p SCREEN-vector, a pSecTag-vector, a pTEFI-vector, a pTracer-vector, a pTrc-vector, a pUB6-vector, a pVAXI-vector, a pYC2-vector, a pYES2-vector, a pZeo-vector, a pcDNA-vector, a pFLAG-vector, a pTAC-vector, a pT7-vector, a Gateway®-vector, a pQE-vector, a pLEXY-vector, a pRNA-vector, a pPK-vector, a pUMVC-vector, a pLIVE-vector, a pCRUZ-vector, a Duet-vector, and other vectors or derivatives thereof.

The vectors may be chosen from the group consisting of high, medium and low copy vectors.

The above described vectors may be used for the transformation or transfection of a host cell in order to achieve expression of a peptide or protein which is encoded by an above described nucleic acid molecule and comprised in the vector DNA. Thus, in a further aspect, to a host cell may include a vector or nucleic acid molecule as disclosed herein.

Also contemplated herein are host cells, which comprise a nucleic acid molecule as described herein integrated into their genomes. The skilled person is aware of suitable methods for achieving the nucleic acid molecule integration. For example, the molecule may be delivered into the host cells by means of liposome transfer or viral infection and afterwards the nucleic acid molecule may be integrated into the host genome by means of homologous recombination. In certain embodiments, the nucleic acid molecule is integrated at a site in the host genome, which mediates transcription of the peptide or protein encoded by the nucleic acid molecule. In various embodiments, the nucleic acid molecule further comprises elements which mediate transcription of the nucleic acid molecule once the molecule is integrated into the host genome and/or which serve as selection markers.

In certain embodiments, the nucleic acid molecule is transcribed by a polymerase natively encoded in the host genome. In various embodiments, the nucleic acid molecule is transcribed by a RNA-polymerase which is non-native to the host genome. In such embodiments, the nucleic acid molecule may further comprise a sequence encoding for a polymerase and/or the host genome may be engineered or the host cell may be infected to comprise a nucleic acid sequence encoding for an exogenous polymerase. The host cell may be specifically chosen as a host cell capable of expressing the gene. In addition or otherwise, in order to produce the isolated polypeptide, the nucleic acid coding for it can be genetically engineered for expression in a suitable system. Transformation can be performed using standard techniques (Sambrook, J. et al. (2001), Molecular Cloning: A Laboratory Manual, 3rd Ed., Cold Spring Harbor Laboratory Press, Cold Spring Harbor, NY).

Prokaryotic or eukaryotic host organisms comprising such a vector for recombinant expression of the polypeptide as described herein form also part. Suitable host cells can be prokaryotic cells. In certain embodiments the host cells are selected from the group consisting of gram positive and gram negative bacteria. In some embodiments, the host cell is a gram negative bacterium, such as E. coli. In certain embodiments, the host cell is E. coli, in particular E. coli BL21 (DE3) or other E. coli K12 or E. coli B834 derivatives. In further embodiments, the host cell is selected from the group consisting of Escherichia coli (E. coli), Pseudomonas, Serratia marcescens, Salmonella, Shigella (and other enterobacteriaceae), Neisseria, Hemophilus, Klebsiella, Proteus, Enterobacter, Helicobacter, Acinetobacter, Moraxella, Helicobacter, Stenotrophomonas, Bdellovibrio, Legionella, acetic acid bacteria, Bacillus, Bacilli, Carynebacterium, Clostridium, Listeria, Streptococcus, Staphylococcus, and Archaea cells. Suitable eukaryotic host cells are among others CHO cells, insect cells, fungi, yeast cells, e.g., Saccharomyces cerevisiae, S. pombe, Pichia pastoris.

In certain embodiments, the host cell is a prokaryotic cell, such as E. coli, in particular E. coli BL21 (DE3), E. coli BL21, E. coli K12, E. coli BLR, E. coli BL21 AI, E. coli BL21 pLysS, E. coli XL1 and E. coli DH5a. Further suitable E. coli strains include, but are not limited to DH1, DH5a, DM1, HB101, JMIOI-110, Rosetta(DE3)pLysS, SURE, TOP10, XLI-Blue, XL2-Blue and XLIO-Blue strains.

The transformed host cells are cultured under conditions suitable for expression of the nucleotide sequence encoding the polypeptide. In certain embodiments, the cells are cultured under conditions suitable for expression of the nucleotide sequence encoding a polypeptide and, optionally, its secretion.

For producing the recombinant peptide or protein of interest in form of the fusion proteins described herein, a vector can be introduced into a suitable prokaryotic or eukaryotic host organism by means of recombinant DNA technology (as already outlined above). For this purpose, the host cell is first transformed with a vector comprising a nucleic acid molecule using established standard methods (Sambrook, J. et al. (2001), supra). The host cell is then cultured under conditions, which allow expression of the heterologous DNA and thus the synthesis of the corresponding polypeptide. Subsequently, the polypeptide is recovered either from the cell or from the cultivation medium.

For expression of the peptides and proteins several suitable protocols are known to the skilled person. The expression of a recombinant polypeptide may be achieved by the following method comprising: (a) introducing a nucleic acid molecule or vector into a host cell, wherein the nucleic acid molecule or vector encodes the recombinant polypeptide; and (b) cultivating the host cell in a culture medium under conditions that allow expression of the recombinant polypeptide.

Step (a) may be carried out by using suitable transformation and transfection techniques known to those skilled in the art. These techniques are usually selected based on the type of host cell into which the nucleic acid is to be introduced. In some embodiments, the transformation may be achieved using electroporation or heat shock treatment of the host cell.

Step (b) may include a cultivation step that allows growth of the host cells. Alternatively, such step allowing growth of the host cells and a step that allows expression of the polypeptide may be performed separately in that the cells are first cultivated such that they grow to a desired density and then they are cultivated under conditions that allow expression of the polypeptide. The expression step can however still allow growth of the cells.

The method may further include a step of recovering the expressed polypeptide. The polypeptide may be recovered from the growth medium, if it is secreted, or from the cells or both. The recovery of the polypeptide may include various purification steps.

Generally, any known culture medium suitable for growth of the selected host may be employed in this method. In various embodiments, the medium is a rich medium or a minimal medium. Also contemplated herein is a method, wherein the steps of growing the cells and expressing the peptide or protein comprise the use of different media. For example, the growth step may be performed using a rich medium which is replaced by a minimal medium in the expression step. In certain cases, the medium is selected from the group consisting of LB medium, TB medium, 2YT medium, synthetical medium and minimal medium.

In some embodiments, glycerol is added to the culture medium in concentrations of 0.1 v/v % to up to 50 v/v %. The addition of glycerol to the growth medium may positively influence the amount of secreted peptide or protein, if secretion is desired. Without wishing to be bound to a specific theory, it is believed that the folding rate of the recombinantly expressed polypeptides in the cytoplasm of the expression host cell is reduced due to the presence of glycerol in the culture medium. As the intracellular peptide or protein folding rate is reduced, the secretion efficiency is increased.

In some embodiments, the above method further comprises the secretion of the recombinant polypeptide into the culture medium by cultivating the host cell under conditions that allow secretion of the recombinant polypeptide into the culture medium. The term "conditions that allow secretion of the recombinant polypeptide into the culture medium" means that the temperature and medium are chosen such that the polypeptide is secreted. In certain embodiments, this involves supplementing the medium with an inducer of protein expression or changing a physical parameter to induce the protein expression. For example, if the vector encoding for the polypeptide of interest is constructed such that the sequence encoding for the polypeptide of interest is under transcriptional control, the addition of a substrate which releases the suppression of the transcriptional control may be added to the medium or the culture conditions may be reset to induce transcription. Thus, in some embodiments, the medium may be supplemented with IPTG, arabinose, tryptophan and/or maltose, and/or the culture temperature may be changed and/or the culture may be exposed to UV light. In various embodiments, the conditions that allow secretion of the recombinant polypeptide are the same used for the expression of the polypeptide.

In various embodiments, where secretion of the polypeptide into the culture medium is desired, the first amino acid sequence comprises the C-terminal part of SEQ ID NO:1 or a functional variant thereof, as described herein. This means that the amino acids corresponding to the C-terminal 10, preferably C-terminal 20, more preferably C-terminal 30, most preferably C-terminal 40, 45, 50, 55, or 60 or more amino acids of SEQ ID NO:1 are included in the first amino acid sequence. In various embodiments, these may be modified by substitution(s) and/or deletion(s), as defined herein, wherein deletions, if present, are preferably limited to up to 5 single amino acid residues, preferably up to 3, more preferably 2 or 1 amino acids, most preferably no deletion.

Furthermore, in various embodiments where secretion is desired, the host cell may express the other components of the T1 SS, in particular TolC, HlyB, and HlyD. The use of the type 1 secretion system may ensure that the polypeptide is directly secreted to the extracellular space without an intermediate step in the periplasm so that the exposure of the expressed peptide or protein to proteases is avoided.

The other components of the T1 SS may include HlyB and HlyD. In some cases, the two proteins are endogenously expressed, whereas in other cases the two proteins are recombinantly expressed. In the latter case, the nucleic acid molecules encoding for HlyB and/or HlyD may be comprised in the vector harboring the nucleic acid molecule. Alternatively, both proteins are encoded together in one or two additional vectors. For example, HlyB and HlyD may be encoded in a single expression vector which comprises several integration sites for encoding nucleic acid sequences. Such a vector may also comprise a nucleic acid molecule. Suitable vectors may be Duet vectors (Novagen) or derivatives thereof. The above-mentioned one or two additional vectors may comprise selection markers which are the same or different from the selection marker of the vector. Host cells comprising the desired combination of expression vectors can be easily selected if the selection markers of the employed vectors are different from each other. Exemplary sequences of HlyB and HlyD are set forth in SEQ ID Nos. 30 and 31, respectively.

In some embodiments, if the host cell does not endogenously express TolC, a nucleic acid molecule encoding for TolC may also be comprised in one of the vectors comprised in the host cell or be introduced in the host with an additional vector. An exemplary sequences of TolC is set forth in SEQ ID NO: 32. In certain embodiments, if the expression and secretion of the recombinant polypeptide is desired, the host cell expresses HlyB, HlyD and TolC in addition to the recombinant peptide or protein. This allows for secretion of the recombinant peptide or protein.

In some embodiments, the entire culture of the host cell, e.g., during growth and expression, is carried out in minimal medium. In various embodiments, the method comprises secretion of the recombinant polypeptide and during secretion the host cell may be cultivated in minimal medium. Minimal medium is advantageous if the recombinant polypeptide is secreted, as the protein, lipid, carbohydrate, pigment, and impurity content in this medium is reduced and thus circumvents or reduces the need of extensive purification steps.

Furthermore, supplementation of the culture medium with alkaline earth metal salts may be advantageous for secretion of the recombinant polypeptide. For an improvement of the secretion, the medium may be complemented at least during secretion or during the entire cell cultivation with at least one alkaline earth metal salt. In some embodiments, the final concentration in the medium is in the range of 1-40 mM. In certain embodiments, the secretion medium may be complemented with at least one alkaline earth metal salt selected from the group consisting of a magnesium salt, calcium salt, strontium salt, or barium salt. In some embodiments, the secretion medium comprises 1-40 mM of a calcium salt. The total concentration of 1-40 mM earth alkaline metal salt may be achieved by combining several salts from different earth alkaline metals and/or the same earth alkaline metal. If the earth alkaline metal is selected from magnesium salt, calcium salt, strontium salt, or barium salt, the composition may comprise 1-40 mM of a single calcium, strontium or barium salt or combinations of several magnesium, calcium, strontium or barium salts, leading to a total concentration in the range of 1-40 mM. In particular, a calcium salt concentration in the range of 1-40 mM may be achieved by combining several calcium salts leading to a total concentration of 1-40 mM. In certain embodiments, the calcium salts are selected from the group consisting of $CaCl_2$), $CaCO_3$, $Ca(OH)_2$, $CaSO_4$ $2H_2O$, $Ca_3(PO_4)_2$, $Ca(CH_3COO)_2$ $H_2O$, and $Ca(C_2H_3O_2)_2$. In one specific embodiment, the medium contains 1-40 mM $Ca^{2+}$ ions. The medium supplemented accordingly, may be the medium used in the cultivation step that allows expression and/or secretion of the polypeptide.

In particular, if the recombinant polypeptide comprises one or more GG repeats of SEQ ID NO:1, as defined above, the secretion efficiency is significantly raised if the medium is supplemented with earth alkaline metal salts.

In various other embodiments, the polypeptide is not secreted. In such embodiments, it may be expressed in form of inclusion bodies (IBs). In many cases, it may be useful to express the polypeptide in such an insoluble form, particularly in cases where the peptide of interest is rather short, normally soluble and/or subject to proteolytic degradation within the host cell. Production of the peptide in insoluble form both facilitates simple recovery and additionally protects the peptide from the undesirable proteolytic degradation. This protection from proteolysis may add up with that conferred by the amino acid substitutions/deletions described herein. In such embodiments, the first amino acid sequence may serve as a solubility tag, i.e., an inclusion body (IB) tag, that induces IB formation. In various such embodiments, the first amino acid sequence may comprise at least one GG repeat sequence, as defined above. Calcium ion (or earth alkaline metal ion) binding to the GG repeat(s) may later catalyze the folding of the fusion polypeptide into the native, active conformation with the calcium ions acting as a folding helper/chaperone. It has been described above, that the inventor has found a variety of variants of SEQ ID NO:1, including C-terminal truncations, deletions and substituted variants, that increase renaturation efficiency in such methods compared to HlyA1 (SEQ ID NO:1).

The terms "inclusion body" or "IB", as interchangeably used herein, relate to nuclear or cytoplasmic aggregates of substances, for instance proteins. IBs are undissolved and have a non-unit lipid membrane. In the method, the IBs mainly consist of the fusion protein comprising at least one peptide/protein of interest and the amino acid sequence derived from SEQ ID NO:1, as defined herein.

In various embodiments, in particular where expression of the polypeptide in form of IBs is desired, the expression of the endogenous ABC transporter gene, the endogenous MFP gene and/or the endogenous OMP gene of the T1 SS or the activity of the corresponding gene products in the host cell is inhibited. In various embodiments, the host cell does not express endogenous ABC transporter, endogenous MFP and/or endogenous OMP of the T1 SS. This may include embodiments where any one or all of TolC, HlyB, and HlyD are not expressed by the host cell. The host cell may be engineered accordingly.

Methods to inhibit the expression of genes such as their deletion or insertion of nucleotide sequences destroying the integrity of the promoter sequence or the gene itself are known in the art. A preferred gene expression activity after deletion or disruption may be less than 35%, 30%, 25%, 20%, 15%, 10% or 5% of the activity measured in untreated cells. In other various embodiments, the endogenous ABC transporter, the endogenous MFP and/or the endogenous OMP of the type 1 secretion system are inhibited by antibodies or small molecule inhibitors. In preferred embodiments, the ABC transporter activity is inhibited by ortho-vanadate or an ATP homologous inhibitor such as 8-azido-ATP. Such ATP mimetics are known in the art. The preferred protein activity after inhibitor treatment may be less than 35%, 30%, 25%, 20%, 15%, 10% or 5% of the activity measured in untreated cells. In other embodiments, the transport is inhibited or blocked by the polypeptide itself, for example by over-expressing it.

In various embodiments of the afore-mentioned methods, the polypeptide is recovered from the host cells in form of insoluble inclusion bodies, for example by any of the purification methods disclosed herein.

Renaturation may then be effected by exposing the isolated/purified polypeptide to renaturation conditions, typically buffer conditions wherein the so-called refolding buffer comprises at least 0.01, more preferably 0.01-40 mM of alkaline earth metal ions, in particular $Ca^{2+}$. By virtue of the presence of GG repeats in the first amino acid sequence, such treatment may trigger refolding of the polypeptide into its functional (native) conformation. Interestingly, the refolding of the first amino acid sequence in many instances also induces proper folding of the peptide/polypeptide of interest fused thereto.

The advantages of such a strategy for expression of a fusion protein in form of inclusion bodies are set forth in greater detail in WO 2014/170430 A1, which is herewith included by reference in its entirety.

In various embodiments, the method also encompasses the purification the recombinant polypeptide, wherein the recombinant polypeptide is purified using a method selected from affinity chromatography, ion exchange chromatography, reverse phase chromatography, size exclusion chromatography, and combinations thereof.

In several embodiments, the method may comprise the treatment of the recombinant polypeptide with a protease suitable for cleavage of a protease cleavage site within the recombinant polypeptide. In some embodiments, the recombinant polypeptide is purified prior to proteolytic cleavage using one or more methods disclosed above. Also after cleavage of the recombinant peptide or protein, the method may comprise a further purification step as defined above. Thus, in some embodiments the recombinant polypeptide is purified, subjected to proteolytic cleavage and the peptide or protein of interest is further purified. In other embodiments, the protease may be co-expressed or added to the cultivation medium or expressed by co-cultivated microorganisms, such that cleavage occurs before purification.

In a further aspect, a vector or nucleic acid molecule as disclosed herein may be used for the expression of a recombinant polypeptide. In some embodiments, the vector is used for the expression and optionally secretion of a recombinant polypeptide. The expression or expression and secretion may be achieved using the method described herein.

A method for expression of a recombinant peptide or protein using the above-described nucleic acid molecules may comprise the steps of:

(a) introducing a nucleic acid molecule or a vector as described above into a suitable host cell, wherein the nucleic acid molecule or vector encodes the recombinant polypeptide; and (b) cultivating the host cell in a culture medium under conditions that allow expression of the recombinant polypeptide and optionally secretion of the recombinant polypeptide into the culture medium.

If secretion is not desired, the expression of the recombinant polypeptide in step (b) may be in form of inclusion bodies.

The method can further be defined as the other methods described above. Specifically, the method may further comprise recovering the expressed peptide or protein from the host cell and/or the culture medium. In addition, the host cell may be a prokaryotic cell; and/or the host cell may express HlyB and HlyD; and/or the expression may be performed in minimal culture medium; and/or the culture medium may comprise 1-40 mM of earth alkaline metal ions, such as $Ca^{2+}$; and/or the recombinant polypeptide may be purified using a method selected from affinity chromatography, ion exchange chromatography, reverse phase chromatography, size exclusion chromatography, and combinations thereof; and/or the method may comprises treatment of the recombinant polypeptide with a protease suitable for cleavage of a protease cleavage site within the recombinant polypeptide; and/or the method may comprise a cleavage step followed by purification of the recombinant polypeptide.

In various embodiments, the polypeptide is recovered in form of inclusion bodies and, after purification, exposed to a refolding buffer, wherein the refolding buffer comprises at least 0.01, more preferably 0.01-40 mM of earth alkaline metal ions, such as Ca2+.

EXAMPLES

Materials and Methods

Expression host: *Escherichia coli* BL21 (DE3) (Novagen)
All oligonucleotides were purchased from Microsynth Seqlab GmbH.

Codon optimized nucleotide sequences encoding peptides were purchased from Thermo Fisher Scientific. All enzymes were purchased from NEB, Clontech, Invitrogen or Fermentas.

Expression Protocol

1. Transformation of chemically competent cells with an expression vector encoding for a truncated variant of SEQ ID NO:1 and, optionally, the peptide of interest (as a fusion protein) and plating of the transformed cells on LB agar plates comprising suitable antibiotic(s) for selection of the transformed cells.
2. Incubation of the agar plates over night at 37° C.
3. Inoculation of 2YT medium comprising antibiotics with a single colony from the agar plate for an overnight culture.
4. Incubation at 37° C. and shaking of the culture over night.
5. Inoculation of the main culture comprising 2×YT medium (16 g tryptone/peptone from casein (Roth, #8952.2), 10 g yeast extract (Roth, #2363.2), 5 g NaCl (Roth, #3957.1), ad 1 L demineralized water with the overnight culture resulting in an OD600 of 0.01-0.2 (flasks with baffles)
6. Incubation of the culture at 37° C. at different rpm
7. Induction of the expression the peptide or protein of interest with 1 mM IPTG at an OD600 of 0.4-1.0.
8. Incubation of the cultures for 3 hrs.
9. Culture samples were taken at 0 hrs and 3 hrs post induction and centrifuged for 10 min., 13,000×g, RT.
10. Cell samples were resuspended in water to adjust an OD of 5.0, mixed 4:1 with 5×SDS loading dye and heated (95° C., 10 min).
11. 20 μL samples were loaded on 15% SDS-PAGE gels and SDS-PAGE analysis was performed at 160 V for about 45 min.

Expression and Secretion Protocol

1. Transformation of chemically competent cells with an expression vector encoding for a point mutation variant of SEQ ID NO:1 and plating of the transformed cells on LB agar plates comprising suitable antibiotic(s) for selection of the transformed cells, e.g., ampicillin and kanamycin.
2. Incubation over night at 37° C.
3. Inoculation of 2YT medium comprising antibiotics with a single colony for an overnight culture.
4. Incubation at 37° C. and shaking of the culture overnight.
5. Inoculation of the main culture with 5 mM $CaCl_2$) with the overnight culture resulting in an OD600 of 0.01-0.2 (flasks without baffles)
6. Incubation of the culture at 37° C. at 180 rpm.
7. Induction of the expression of the HlyA1 variant and of the transport complex—consisting of HlyB and HlyD, encoded by pSJ37 or pK184 HlyB, D (TolC, the third protein of this transport complex is consecutively endogenously expressed in *E. coli*) with 1 mM IPTG at an OD600 of 0.4-1-0-
8. Incubation of the cultures for 26 hrs.
9. Culture samples were taken at 6 hrs and 26 hrs post induction and centrifuged for 10 min., 13,000×g, RT.
10. Supernatant samples were mixed 4:1 with 5×SDS loading dye (heat on 95° C., 10 min). Cell samples were resuspended in water to adjust an OD of 5.0 and mixed 4:1 with 5×SDS loading dye (heat on 95° C., 10 min).
11. 20 μL samples were loaded on 15% SDS-PAGE gels and SDS-PAGE analysis was performed at 160 V for about 45 min.

Example 1: Cloning of HlyA1 Fragments and Variants

The cloning of the various plasmids with HlyA1 trunca-tions/variations is based on the parental plasmid pSU-HlyA1 (SEQ ID NO:29). Each of the 60 C-terminal amino acids of HlyA1 (SEQ ID NO:1) was mutated in all 20 naturally occurring proteinogenic amino acids by use of nnn codons.

DNA fragments were amplified by Q5 High-Fidelity DNA Polymerase (according to the NEB protocol), digested with DpnI (according to the NEB protocol) and purified with SpeedBeads (DeAngelis M., Wang D. and Hawkins, T. 1995. Solid-phase reversible immobilization for the isola-tion of PCR products. Nucleic Acids Res. 23: 4742-4743). Plasmids were Created Using Two Cloning Strategies:

Cloning strategy 1: The amplification of a DNA fragment and linearization by phosphorylation and ligation (protocol according to NEB). Example: Primer 1 (SEQ ID NO:33) and Primer 2 (SEQ ID NO:34) were used to generate construct 1.

Cloning strategy 2: The amplification of one or more DNA fragments with 15 bp complementary 5' elongations which are linearized via Gibson reactions (Gibson, D. et al., 2009. Enzymatic assembly of DNA molecules up to several hundred kilobases. Nature Methods, 6: 343-5). Example: Primer 3 (SEQ ID NO:35) and Primer 4 (SEQ ID NO:36) were used to amplify the plasmid backbone for construct 2. Primer 5 (SEQ ID NO:37) and primer 6 (SEQ ID NO:38) were used to amplify the DNA insert for construct 2.

Example 2: Expression and Secretion of HlyA1 Variants

The expression and secretion of the generated HlyA1 fragments/variants per se was quantified by SDS-PAGE. During fermentation, the amount of secreted protein was determined by Bradford Candidates were sequenced and solubility and proteolytic degradation were assessed by SDS-PAGE. The solubility of the variants was determined by comparing the bands of precipitated protein in the cell extract. The proteolytic degradation was determined by comparing the proteolytic degradation bands in the super-natant.

The following single mutations were found to have increased solubility (substitutions/deletions indicated rela-tive to SEQ ID NO:1):
Y161T, G162E, G162C, S163D, G165M, I171D, K176C, S179D, S179C, A180D, A181C, V186D, K187C, K187P, del187, E188H, R190Q, R190A, del190, T191D, A193E, A193C, A193P, A193L, S194T, S194V, S194I, L196G, Q197G, L198E, L198P, S199D, S199P, G200S, N201E, N201P, N201A, F205S, F205C, S206E, S206C, S206P, S206L, R209T, R209G, del209, N210P, I212D, A218H and A218C.

The following single mutations were found to have decreased solubility: A193M, A193W, and T215N.

The following single mutations were found to have increased resistance to proteolytic degradation: G162C, G165M, I171D, S179D, E188H, R190Q, del190, T191D, A193E, A193P, S194I, L198E, L198P, S199D, F205C, R209T, R209G, I212D, A218H and A218C.

The following single mutations were found to have decreased resistance to proteolytic degradation: S163N, K176L, G200S, and S203R.

It Is understood that all other single mutations not listed above as having increased or decreased solubility or increased or decreased resistance to proteolytic degradation were essentially similar to the non-mutated reference sequence of SEQ ID NO:1 with regard to these properties.

For further analysis, double and triple mutations were produced starting from single mutation L198P. All tested mutants: T191D+L198P, A193P+L198P, T191H+A193H+ L198P, deli 91+A192P+L198P, T191G+L195S+L198P, A218D+L198P showed increased protein stability compared to HlyA1 (SEQ ID NO:1) and the single mutant L198P in stability assays conducted via SDS-PAGE analysis. T191D+ L198P, T191P+T198P, T191H+A193D+L198P, and T191G+L195S+L198P showed particular high stability at protein concentrations of 15-35 g/L and over time periods of up to 26 hours (FIG. 1).

Example 3: Optimized HlyA1 Variants/Fragments for Renaturation

Figure 2:
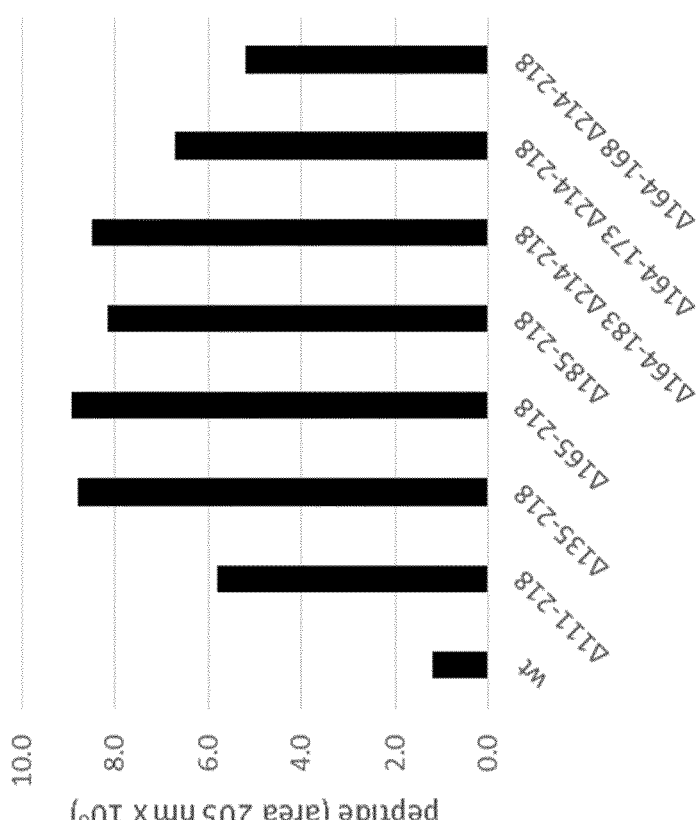
FIG. 2 shows renaturation efficiency (A) and amount of peptide formed (B). The renaturation efficiency (A) was determined from the set and the determined protein concentration after renaturation using the absorption at 280 nm and the corresponding extinction coefficient (Nanodrop). The integrated areas from HPLC/MS measurements at 205 nm reflect the amount of peptide formed after TEV-cleavage (B). Error bars indicate the deviation for n=2 or 3. On the X axis the different fragments are shown by indication of the deleted amino acids relative to SEQ ID NO:1.
Figure 2:
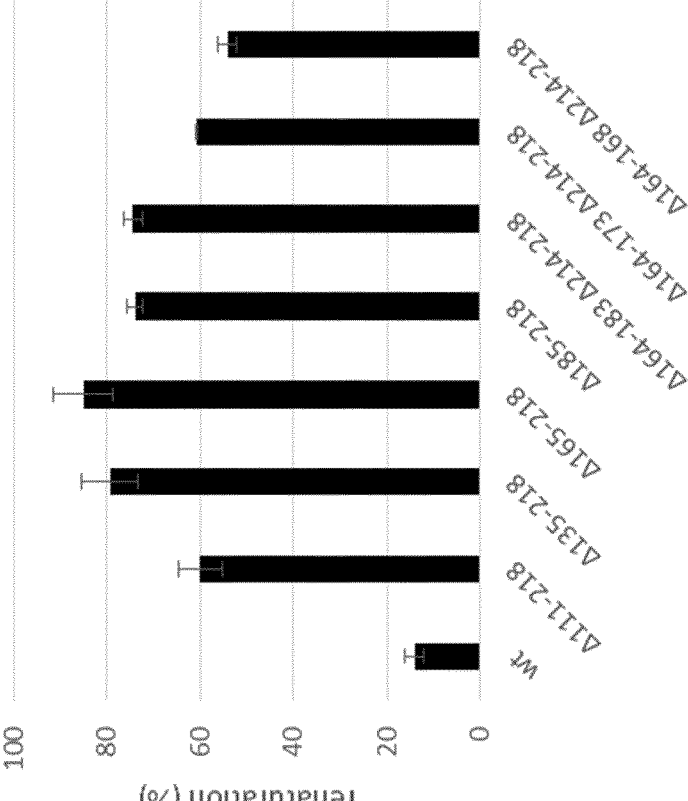

Fusion constructs of HlyA1 wt (SEQ ID NO:1) and deletion variants thereof (SEQ ID Nos. 22-28) with a peptide of interest (SEQ ID NO:39) C-terminally fused thereto were designed. Fusion constructs were expressed as inclusion bodies (IBs) in *E. coli* BL21 (DE3), IBs were prepared via BugBuster Kit and the IBs dissolved in 6 M GuHCl (1:4 w/v). After solubilization overnight, 1 mM stock solution of each construct was set in 6 M GuHCl. Renaturation was performed at room temperature for 20 min setting a final concentration of 0.05 mM in a total volume of 500 µL renaturation buffer. The renaturation efficiency was deter-mined in the cleared supernatant by UV/Vis spectroscopy (FIG. 2A). TEV-cleavage-reactions were performed of 3 h at 30° C. using the renatured protein sample and purified TEV-protease (1:25 molar ratio). The amount and identity of produced peptide was determined via HPLC/MS (FIG. 2B).

All truncated variants del111-218 (SEQ ID NO:22), del135-218 (SEQ ID NO:23), del165-218 (SEQ ID NO:24), del185-218 (SEQ ID NO:25), del164-183+del 214-218 (SEQ ID NO:26), del164-173+del 214-218 (SEQ ID NO:27), del164-168+del214-218 (SEQ ID NO:28), with the indicated SEQ ID Nos referring to the first amino acid sequence, show an increased renaturation efficiency com-pared to the HlyA1 wt (first amino acid: SEQ ID NO:1) construct (FIG. 2A). Almost quantitative TEV-cleavage occurred in all cases under the chosen reaction conditions. Therefore, the amount of peptide obtained (FIG. 2B) strictly depends on the renaturation efficiency (FIG. 2A).

The highest renaturation efficiency over all variants was observed for the variants Δ165-218 (first amino acid sequence: SEQ ID NO:24). The variants Δ135-218 (first amino acid sequence: SEQ ID NO:23), Δ185-218 (first amino acid sequence: SEQ ID NO:25) and Δ164-183 Δ214-218 (first amino acid sequence: SEQ ID NO:26) and EPP (first amino acid sequence: SEQ ID NO:20) also show very high renaturation efficiencies. In all variants increased pep-tide yields due to better renaturation was observed.

All documents cited herein, are hereby incorporated by reference in their entirety. The embodiments illustratively described herein may suitably be practiced in the absence of any element or elements, limitation or limitations, not spe-cifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A polypeptide variant comprising a first amino acid sequence, wherein the first amino acid sequence has at least 80% sequence identity over its entire length with the amino acid sequence set forth in SEQ ID NO:1 (HlyA1) and comprises at least one amino acid substitution or deletion at the position corresponding to position 198 of SEQ ID NO:1, and wherein the first amino acid sequence is at least 100 amino acids in length.

2. The polypeptide variant of claim 1, wherein the first amino acid sequence comprises any one or more of the amino acid substitution(s) selected from the group consisting of: 198E and 198P.

3. The polypeptide variant of claim 1, wherein the first amino acid sequence further comprises any one or more of the amino acid deletions: Δ187, Δ190, Δ191, Δ192, and Δ209.

4. The polypeptide variant of claim 1, wherein the first amino acid sequence further comprises any two or more of the amino acid substitution(s): 161T, 162E, 162C, 163N, 165M, 171D, 176C, 179D, 179C, 180D, 181C, 186D, 187C, 187P, 188H, 190Q, 190A, 191E, 191D, 191H, 191P, 193E, 193C, 193P, 193L, 193H, 194P, 194T, 194V, 194I, I196G, 197G, 198E, 198P, 199D, 199P, 201E, 201P, 201A, 205S, 205C, 205P, 206E, 206C, 206P, 206L, 209T, 209G, 210P, 212D, 218D, 218H, and 218C.

5. The polypeptide variant of claim 1, wherein the first amino acid sequence comprises any one of the following sets of substitutions and/or deletions: 191D+198P, 191P+198P, 193P+198P, 191H+193H+198P, 191H+193D+198P, 191G+195S+198P, 191E+194P+198P, del191+192P+198P, 191G+L195S+198P, and 218D+198P.

6. The polypeptide variant of claim 1, wherein the first amino acid sequence comprises amino acid substitutions/deletions in the following positions using the numbering of SEQ ID NO:1:

162 and 198;
165 and 198;
171 and 198;
179 and 198;
188 and 198;
190 and 198;
191 and 198;
193 and 198;
194 and 198;
198 and 199;
198 and 201;
198 and 205;
198 and 209;
198 and 212;
198 and 218;

162, 165 and 198;
162, 171 and 198;
162, 179 and 198;
162, 188 and 198;
162, 190 and 198;
162, 191 and 198;
162, 193 and 198;
162, 194 and 198;
162, 198 and any one of 199, 201, 205, 209, 212 and 218;
165, 171 and 198;
165, 179 and 198;
165, 188 and 198;
165, 190 and 198;
165, 191 and 198;
165, 193 and 198;
165, 194 and 198;
165, 198 and any one of 199, 201, 205, 209, 212 and 218;
171, 179 and 198;
171, 188 and 198;
171, 190 and 198;
171, 191 and 198;
171, 193 and 198;
171, 194 and 198;
171, 198 and any one of 199, 201, 205, 209, 212 and 218;
179, 188 and 198;
179, 190 and 198;
179, 191 and 198;
179, 193 and 198;
179, 194 and 198;
179, 198 and any one of 199, 201, 205, 209, 212 and 218;
188, 190 and 198;
188, 191 and 198;
188, 193 and 198;
188, 194 and 198;
188, 198 and any one of 199, 201, 205, 209, 212 and 218;
190, 191 and 198;
190, 193 and 198;
190, 194 and 198;
190, 198 and any one of 199, 201, 205, 209, 212 and 218;
191, 193 and 198;
191, 194 and 198;
191, 198 and any one of 199, 201, 205, 209, 212 and 218;
193, 194 and 198;
193, 198 and any one of 199, 201, 205, 209, 212 and 218;
194, 198 and any one of 199, 201, 205, 209, 212 and 218;
198, 199 and any one of 201, 205, 209, 212 and 218;
198, 201 and any one of 205, 209, 212 and 218;
198, 205 and any one of 209, 212 and 218;
198, 209 and any one of 212 and 218; or
198, 212 and 218.

7. The polypeptide variant of claim 1, wherein the first amino acid sequence comprises amino acid substitutions/deletions in the following positions using the numbering of SEQ ID NO:1:

162C and 198E/P;
165M and 198E/P;
171D and 198E/P;
179D and 198E/P;
188H and 198E/P;
190Q and 198E/P;
191D/E and 198E/P;
193E/P and 198E/P;
194P/I and 198E/P;
198E/P and 199D;
198E/P and 201P;
198E/P and 205C/S;
198E/P and 209T/G;

198E/P and 212D;
198E/P and 218D/H/C;
162C, 165M and 198E/P;
162C, 171D and 198E/P;
162C, 179D and 198E/P;
162C, 188H and 198E/P;
162C, 190Q and 198E/P;
162C, 191D/E and 198E/P;
162C, 193E/P and 198E/P;
162C, 194P/I and 198E/P;
162C, 198E/P and any one of 199D, 201P, 205C/S, 209T/G, 212D and 218D/H/C;
165M, 171D and 198E/P;
165M, 179D and 198E/P;
165M, 188H and 198E/P;
165M, 190Q and 198E/P;
165M, 191D/E and 198E/P;
165M, 193E/P and 198E/P;
165M, 194P/I and 198E/P;
165M, 198E/P and any one of 199D, 201P, 205C/S, 209T/G, 212D and 218D/H/C;
171D, 179D and 198E/P;
171D, 188H and 198E/P;
171D, 190Q and 198E/P;
171D, 191D/E and 198E/P;
171D, 193E/P and 198E/P;
171D, 194P/I and 198E/P;
171D, 198E/P and any one of 199D, 201P, 205C/S, 209T/G, 212D and 218D/H/C;
179D, 188H and 198E/P;
179D, 190Q and 198E/P;
179D, 191D/E and 198E/P;
179D, 193E/P and 198E/P;
179D, 194P/I and 198E/P;
179D, 198E/P and any one of 199D, 201P, 205C/S, 209T/G, 212D and 218D/H/C;
188H, 190Q and 198E/P;
188H, 191D/E and 198E/P;
188H, 193E/P and 198E/P;
188H, 194P/I and 198E/P;
188H, 198E/P and any one of 199D, 201P, 205C/S, 209T/G, 212D and 218D/H/C;
190Q, 191D/E and 198E/P;
190Q, 193E/P and 198E/P;
190Q, 194P/I and 198E/P;
190Q, 198E/P and any one of 199D, 201P, 205C/S, 209T/G, 212D and 218D/H/C;
191D/E, 193E/P and 198E/P;
191D/E, 194P/I and 198E/P;
191D/E, 198E/P and any one of 199D, 201P, 205C/S, 209T/G, 212D and 218D/H/C;
193E/P, 194P/I and 198E/P;
193E/P, 198E/P and any one of 199D, 201P, 205C/S, 209T/G, 212D and 218D/H/C;
194P/I, 198E/P and any one of 199D, 201P, 205C/S, 209T/G, 212D and 218D/H/C;
198E/P, 199D and any one of 201P, 205C/S, 209T/G, 212D and 218D/H/C;
198E/P, 201P and any one of 205C/S, 209T/G, 212D and 218D/H/C;
198E/P, 205C/S and any one of 209T/G, 212D and 218D/H/C;
198E/P, 209T/G and any one of 212D and 218D/H/C; or
198E/P, 212D and 218D/H/C.

8. The polypeptide variant of claim 1, wherein the polypeptide variant comprises a second amino acid sequence N-terminal or C-terminal to the first amino acid sequence, wherein the second amino acid sequence encodes for at least one peptide or polypeptide of interest.

9. The polypeptide variant of claim 8, wherein the second amino acid sequence is linked directly or via a linker sequence to the N- or C-terminal end of the first amino acid sequence, the linker sequence optionally being 1 to 30 amino acids in length.

10. A nucleic acid molecule encoding the polypeptide variant of claim 1.

11. A vector comprising the nucleic acid molecule according to claim 10.

12. A host cell comprising the nucleic acid molecule according to claim 10, wherein the host cell is a prokaryotic host cell.

13. A method for the production of a polypeptide variant of claim 1, wherein the method comprises:

cultivating a host cell comprising a nucleic acid molecule that encodes the polypeptide variant under conditions that allow the expression of the polypeptide variant; and isolating the expressed polypeptide variant from the host cell.

14. The polypeptide variant of claim 1, wherein the first amino acid sequence further comprises one or more amino acid substitution(s) or deletion(s) in any one of the positions corresponding to positions 161, 162, 163, 165, 171, 176, 179, 180, 181, 186, 187, 188, 190, 191, 192, 193, 194, 195, 196, 197, 199, 200, 201, 205, 206, 209, 210, 212, and 218 of SEQ ID NO: 1.

15. The polypeptide variant of claim 14, wherein the first amino acid sequence comprises: any one or more of the amino acid substitution(s) selected from the group consisting of: 161T, 162E, 162C, 163D, 165M, 171D, 176C, 179D, 179C, 180D, 181C, 186D, 187C, 187P, 188H, 190Q, 190A, 191D, 191E, 191G, 191H, 191P, 192P, 193D, 193E, 193C, 193P, 193L, 193H, 194T, 194V, 194I, 194P, 195S, 196G, 197G, 199D, 199P, 200S, 201E, 201P, 201A, 205S, 205C, 205P, 206E, 206C, 206P, 206L, 209T, 209G, 210P, 212D, 218D, 218H, and 218C.

\* \* \* \* \*